US012653836B2

(12) United States Patent
Rabinowitz et al.

(10) Patent No.: US 12,653,836 B2
(45) Date of Patent: Jun. 16, 2026

(54) KETOGENIC DIET AND KETONE SUPPLEMENTATION FOR CANCER THERAPY

(71) Applicant: The Trustees of Princeton University, Princeton, NJ (US)

(72) Inventors: Joshua D. Rabinowitz, Princeton, NJ (US); Lifeng Yang, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 822 days.

(21) Appl. No.: 18/003,753

(22) PCT Filed: Jul. 15, 2021

(86) PCT No.: PCT/US2021/041783
§ 371 (c)(1),
(2) Date: Dec. 29, 2022

(87) PCT Pub. No.: WO2022/015951
PCT Pub. Date: Jan. 20, 2022

(65) Prior Publication Data
US 2023/0255997 A1     Aug. 17, 2023

Related U.S. Application Data

(60) Provisional application No. 63/052,027, filed on Jul. 15, 2020.

(51) Int. Cl.
A61K 31/7068     (2006.01)
A23L 33/00     (2016.01)
(Continued)

(52) U.S. Cl.
CPC .......... A61K 31/7068 (2013.01); A23L 33/30 (2016.08); A61K 31/337 (2013.01);
(Continued)

(58) Field of Classification Search
CPC .............. A61K 31/7068; A61K 31/337; A61K 31/519; A61K 33/243; A61K 45/06;
(Continued)

(56) References Cited

U.S. PATENT DOCUMENTS 6,214,875 B1     4/2001   Yang
7,569,350 B2     8/2009   Gocke et al.
(Continued)

FOREIGN PATENT DOCUMENTS

CA          2140866 C      5/2003
CA          2688293 A1     12/2008
(Continued)

OTHER PUBLICATIONS

Jameson et al. (JAMA Oncology, 2020, vol. 6, pp. 125-132) (Year: 2020).*
(Continued)

*Primary Examiner* — Scarlett Y Goon
*Assistant Examiner* — Sarah Grace Hibshman
(74) *Attorney, Agent, or Firm* — Hamilton, Brook, Smith & Reynolds, P.C.

(57)     ABSTRACT

Disclosed herein are methods for treating cancer, particularly gastrointestinal cancers, such as pancreatic cancer and colon cancer, with chemotherapeutic agent(s) in subjects on a ketogenic diet or a ketone supplement or both.

13 Claims, 60 Drawing Sheets

(51) Int. Cl.
| | |
|---|---|
| *A61K 31/337* | (2006.01) |
| *A61K 31/519* | (2006.01) |
| *A61K 33/243* | (2019.01) |
| *A61K 45/06* | (2006.01) |
| *A61P 1/00* | (2006.01) |
| *A61P 1/18* | (2006.01) |
| *A61P 35/00* | (2006.01) |
| *A61P 35/04* | (2006.01) |

(52) U.S. Cl.
CPC .......... *A61K 31/519* (2013.01); *A61K 33/243* (2019.01); *A61K 45/06* (2013.01); *A61P 1/00* (2018.01); *A61P 1/18* (2018.01); *A61P 35/00* (2018.01); *A61P 35/04* (2018.01)

(58) Field of Classification Search
CPC .... A23L 33/30; A61P 1/00; A61P 1/18; A61P 35/00; A61P 35/04
See application file for complete search history.

(56) References Cited

U.S. PATENT DOCUMENTS

| | | | |
|---|---|---|---|
| 10,130,600 | B2 | 11/2018 | Rabinowitz et al. |
| 10,772,862 | B2 | 9/2020 | Rabinowitz et al. |
| 2006/0217441 | A1 | 9/2006 | Akimoto et al. |
| 2010/0256235 | A1 | 10/2010 | Puder et al. |
| 2016/0120832 | A1 | 5/2016 | Rabinowitz et al. |

FOREIGN PATENT DOCUMENTS

| | | | |
|---|---|---|---|
| WO | 94/02108 | A1 | 2/1994 |
| WO | 2006/065735 | A1 | 6/2006 |
| WO | 2012/165345 | A1 | 12/2012 |
| WO | 2012/172411 | A1 | 12/2012 |
| WO | 2014/183047 | A1 | 11/2014 |

OTHER PUBLICATIONS

Shukla et al. (Cancer & Metabolism 2014, vol. 2, article 18) (Year: 2014).*
Funahashi, H. et al., Opposing effects of n-6 and n-3 polyunsaturated fatty acids on pancreatic cancer growth, Pancreas, 36(4): 353-62 (2008).
Nicolaou, K.C. et al., Calicheamicin 911: A rationally designed molecule with extremely potent and selective DNA cleaving properties and apoptosis inducing activity, Angew Chem Intl Ed Engl, 33:183-186 (1994).
Weikang, Z. et al., "Modulatory Effects of EPA and DHA on Proliferation and Apoptosis of Pancreatic Cancer Cells", Journal of Huazhong University of Science and Technology, Medical Science, vol. 27, No. 5, pp. 547-550 (2007).
Aminzadeh-Gohari, S., et al., "A ketogenic diet supplemented with medium-chain triglycerides enhances the anti-tumor and anti-angiogenic efficacy of chemotherapy on neuroblastoma xenografts in a CD1-nu mouse model", 2017, Oncotarget 8, 64728-64744.
Anonymous Author: "NCT04631445: Study Evaluating the Ketogenic Diet in Patients With Metastatic Pancreatic Cancer", Nov. 10, 2020 (Nov. 10, 2020), 5 pages.
Antoch, G., et al., "Accuracy of whole-body dual-modality fluorine-18-2-fluoro-2-deoxy-D-glucose positron emission tomography and computed tomography (FDG-PET/CT) for tumor staging in solid tumors: comparison with CT and PET", 2004, J. Clin. Oncol. Off. J. Am. Soc. Clin. Oncol. 22, 4357-4368.
Barborka, C.J. "Ketogenic Diet Treatment of Epilepsy in Adults", 1928, J. Am. Med. Assoc. 91, 73.
Bates, M. "Kinetics of ketone body metabolism in fasted and diabetic rats", 1971, Am. J. Physiol.-Leg. Content 221, 984-991.
Birsoy, K., et al., "An Essential Role of the Mitochondrial Electron Transport Chain in Cell Proliferation Is to Enable Aspartate Synthesis", Cell 162, 540-551, 2015.

Blodgett, T.M., et al., "PET/CT: form and function", Radiology 242, 360-385, 2007.
Brooks, G.A. "The Science and Translation of Lactate Shuttle Theory", Cell Metab. 27, 757-785, 2018.
Caffa, I., et al., "Fasting-mimicking diet and hormone therapy induce breast cancer regression", 2020, Nature 583, 620-624.
De Groot, S., et al., "Fasting mimicking diet as an adjunct to neoadjuvant chemotherapy for breast cancer in the multicentre randomized phase 2 DIRECT trial", Nat. Commun. 11, 3083, 2020.
Dobin, A., et al., "STAR: ultrafast universal RNA-seq aligner", Bioinformatics 29, 15-21, 2013.
Draoui, N., et al., "Lactate shuttles at a glance: from physiological paradigms to anti-cancer treatments", Dis. Model. Mech. 4, 727-732, 2011.
Erkan, M., et al., "The role of stroma in pancreatic cancer: diagnostic and therapeutic implications", Nat. Rev. Gastroenterol. Hepatol. 9, 454-467, 2012.
Faubert, B., et al., "Lactate Metabolism in Human Lung Tumors", Cell 171, 358-371.e9, 2017.
Favaro, E., et al. "Glucose Utilization via Glycogen Phosphorylase Sustains Proliferation and Prevents Premature Senescence in Cancer Cells", Cell Metab. 16, 751-764, 2012.
Furukawa K et al: "Investigating the effect of chemotherapy combined with ketogenic diet on stage IV colon cancer", Journal of Clinical Oncology; 2019 Annual Meeting of the American Society of Clinical Oncology, ASCO 2019; May 31, 2019 to Jun. 4, 2019; Chicago, IL, USA, Lippincott Williams & Wilkins, USA, vol. 37, No. Supplement 15, May 1, 2019 (May 1, 2019).
Gao, X., et al., "Dietary methionine influences therapy in mouse cancer models and alters human metabolism", Nature, Aug. 2019; 572 (7769): 397-401.
García-Cañaveras, J.C., et al., "The Tumor Metabolic Microenvironment: Lessons from Lactate", Cancer Res. 79, 3155-3162, 2019.
Goodman, R.P., et al., "Hepatic NADH reductive stress underlies common variation in metabolic traits", Nature 1-5, 2020.
Hagihara, K., et al., "Promising Effect of a New Ketogenic Diet Regimen in Patients with Advanced Cancer", Nutrients, 2020, 12(5) 1473, 12 pages.
Hingorani, S.R., et al., "Trp53R172H and KrasG12D cooperate to promote chromosomal instability and widely metastatic pancreatic ductal adenocarcinoma in mice", Cancer Cell 7, 469-483, 2005.
Hompland, T., et al., "Combined MR Imaging of Oxygen Consumption and Supply Reveals Tumor Hypoxia and Aggressiveness in Prostate Cancer Patients", Cancer Res. 78, 4774-4785, 2018,.
Hopkins, B.D., et al., "Suppression of insulin feedback enhances the efficacy of PI3K inhibitors", Nature 560, 499-503, 2018.
Hui, S., et al., "Glucose feeds the TCA cycle via circulating lactate", Nature 551, 115-118, 2017.
Hui, S., et al., "Quantitative Fluxomics of Circulating Metabolites", Cell Metabolism, 32, 676-688, Oct. 6, 2020.
Iyikesici, M., "Long-Term Survival Outcomes of Metabilocally Supported Chemotherapy with Gemcitabine-Based or FOLFIRINOX Regimen Combined with Ketogenic Diet, Hyperthermia, and Hyperbaric Oxygen Therapy in Metastatic Pancreatic Cancer", Complementary Medicine Research, 27(1): 31-39, Feb. 1, 2020.
Jameson, G.S., et al. "A phase Ib/II pilot trial with nab-paclitaxel plus gemcitabine plus cisplatin in patients (pts) with stage IV pancreatic cancer", J. Clin. Oncol. 35, 341-341, 2017.
Jameson, G.S., et al., "Response Rate Following Albumin-Bound Paclitaxel Plus Gemcitabine Plus Cisplatin Treatment Among Patients With Advanced Pancreatic Cancer: A Phase 1b/2 Pilot Clinical Trial", JAMA Oncol. 6, 125, 2020.
Juweid, M.E., and Cheson, B.D. (2009). "Positron-Emission Tomography and Assessment of Cancer Therapy" (Massachusetts Medical Society).
Kamphorst, J.J., "Hypoxic and Ras-transformed cells support growth by scavenging unsaturated fatty acids from lysophospholipids", 2013, Proc. Natl. Acad. Sci. 110, 8882-8887.
Kanarek, N., et al., "Dietary modifications for enhanced cancer therapy", Nature 579, 507-517, 2020.
Koong, A.C., et al., "Pancreatic tumors show high levels of hypoxia", Int. J. Radiat. Oncol. 48, 919-922, 2020.

(56)    References Cited

OTHER PUBLICATIONS

Korge, P., et al., "Increased reactive oxygen species production during reductive stress: The roles of mitochondrial glutathione and thioredoxin reductases", Biochim. Biophys. Acta BBA—Bioenerg. 1847, 514-525, 2015.

Lardinois, D., et al., "Staging of non-small-cell lung cancer with integrated positron-emission tomography and computed tomography", N. Engl. J. Med. 348, 2500-2507, 2003.

Li, B., et al., "RSEM: accurate transcript quantification from RNA-Seq data with or without a reference genome", BMC Bioinformatics 12, 323, 16 pages, 2011.

Love, M.I., et al., "Moderated estimation of fold change and dispersion for RNA-seq data with DESeq2", Genome Biol. 15, 550, 2014.

Lunt, S.Y., et al., "Aerobic Glycolysis: Meeting the Metabolic Requirements of Cell Proliferation", Annu. Rev. Cell Dev. Biol. vol. 27 27, 441-464, 2011.

Maddocks, O.D.K., et al., "Modulating the therapeutic response of tumours to dietary serine and glycine starvation", Nature 544, 372-376, 2017.

McGarry, J.D., et al., "Ketone Body Metabolism in the Ketosis of Starvation and Alloxan Diabetes", J. Biol. Chem. 245, 4382-4390, 1970.

Morscher, R.J., et al., "Inhibition of Neuroblastoma Tumor Growth by Ketogenic Diet and/or Calorie Restriction in a CD1-Nu Mouse Model", PLOS One 10, e0129802, 2015.

Notification of Transmittal of the International Search Report and the Written Opinion of the International Searching Authority for International Application No. PCT/US2021/041783, "Ketogenic Diet and Ketone Supplementation for Cancer Therapy", date of mailing: Dec. 23, 2021.

Olive, K.P., et al., "Inhibition of Hedgehog signaling enhances delivery of chemotherapy in a mouse model of pancreatic cancer", Science 324, 1457-1461, 2009.

Patgiri, A., et al., "An engineered enzyme that targets circulating lactate to alleviate intracellular NADH:NAD+ imbalance", Nat. Biotechnol. 38, 309-313, 2020.

Pérez-Escuredo, J., et al., "Monocarboxylate transporters in the brain and in cancer. Biochim. Biophys", Acta BBA—Mol. Cell Res. 1863, 2481-2497, 2016.

Poff, A., et al., "Ketone supplementation decreases tumor cell viability and prolongs survival of mice with metastatic cancer", Int. J. Cancer J. Int. Cancer 135, 1711-1720, 2014.

Puchalska, P., et al., "Multi-dimensional Roles of Ketone Bodies in Fuel Metabolism, Signaling, and Therapeutics", Cell Metab. 25, 262-284, 2017.

Rabinowitz, J.D., et al., "Lactate: the ugly duckling of energy metabolism", Nat. Metab. 2, 566-571, 2020.

Roberts, M.N., et al., "A Ketogenic Diet Extends Longevity and Healthspan in Adult Mice", Cell Metab. 26, 539-546.e5, 2017.

Shimazu, T., et al., "Suppression of oxidative stress by β-hydroxybutyrate, an endogenous histone deacetylase inhibitor", Science 339, 211-214, 2013.

Shukla, S.K., et al., "Metabolic reprogramming induced by ketone bodies diminishes pancreatic cancer cachexia", Cancer Metab. 2, 18, 2014.

Sullivan, L.B., et al., "Supporting Aspartate Biosynthesis Is an Essential Function of Respiration in Proliferating Cells", Cell 162, 552-563, 2015.

Sullivan, M.R., et al., "Quantification of microenvironmental metabolites in murine cancers reveals determinants of tumor nutrient availability", ELife 8, e44235, 2019.

Tanner, L.B., et al., "Four Key Steps Control Glycolytic Flux in Mammalian Cells", Cell Syst. 7, 49-62.e8, 2018.

TeSlaa, T., et al., "The Source of Glycolytic Intermediates in Mammalian Tissues", Cell Metab. S1550413120307282, 2021.

Titov, D.V., et al., "Complementation of mitochondrial electron transport chain by manipulation of the NAD+/NADH ratio", Science 352, 231-235, 2016.

Von Hoff, D.D., et al. "Increased Survival in Pancreatic Cancer with nab-Paclitaxel plus Gemcitabine", N. Engl. J. Med. 369, 1691-1703, 2013.

Weber, D.D., Aminazdeh-Gohari, S., and Kofler, B. (2018). Ketogenic diet in cancer therapy. Aging 10, 164-165.

Weber, D.D., et al., "Ketogenic diet in the treatment of cancer—Where do we stand?", 2020, Mol. Metab. 33, 102-121.

Wu, G.Y., et al., "The effect of ketone bodies on alanine and glutamine metabolism in isolated skeletal muscle from the fasted chick", 1988, Biochem. J. 255, 139-144.

Yang, L., et al., "Serine Catabolismeeds NADH when Respiration Is Impaired", 2020, Cell Metab. 31, 809-821.e6.

Zahra, A., et al., "Consuming a Ketogenic Diet while Receiving Radiation and Chemotherapy for Locally Advanced Lung Cancer and Pancreatic Cancer: The University of Iowa Experience of Two Phase 1 Clinical Trials", 2017, Radiat. Res. 187, 743-754.

Bar-Sagi, D. and Feramisco, J.R., Induction of membrane ruffling and fluid-phase pinocytosis in quiescent fibroblasts by Ras proteins, Science, vol. 233; No. 4768; 1061-1068 (1986).

Bradley, M.C. et al., "Non-steroidal anti-inflammatory drugs and pancreatic cancer risk: a nested case-control study," British Journal of Cancer, vol. 102; 1415-1421 (2010).

Chun, S.Y. et al., "Oncogenic KRAS modulates mitochondrial metabolism in human colon cancer cells by inducing HIF-1a and HIF-2a target genes," Mol. Cancer, vol. 9; No. 293; 1-11 (2010).

Commisso, C. et al., "Macropinocytosis of protein is an amino acid supply route in Ras-transformed cells," Nature, vol. 497; No. 7451; 633-637 (2013).

Deberardinis, R.J. et al, Brick by brick: metabolism and tumor cell growth, Curr. Opin. Genet. Dev., 18(1):54-61 (2008).

Degenhardt, K. & White, E., A mouse model system to genetically dissect the molecular mechanisms regulating tumorigenesis, Clin. Cancer Res., 12(18):5298-5304 (2006).

Degenhardt, K. et al, BAX and BAK mediate p53-independent suppression of tumorigenesis, Cancer Cell, (2):193-203 (2002).

Gaglio, D. et al., Oncogenic K-Ras decouples glucose and glutamine metabolism to support cancer cell growth, Molecular Systems Biology, 7(523): 1-15 (2011).

Gingras, A-C. et al, Regulation of translation initiation by FRAP/mTOR, Genes & Development 15:807-826 (2001).

Green, C.D. and Olson, L.K., Modulation of palmitate-induced endoplasmic reticulum stress and apoptosis in pancreatic ß-cells by stearoyl-CoA desaturase and Elovi6, Am. J. Physiol Endocrinol Metab., 300: E640-E649 (2011).

Guillou, H. et al, The key roles of elongases and desaturases in mammalian fatty acid metabolism: insights from transgenic mice, Prog Lipid Res, 49(2):186-199 (2010).

Guo, J.Y., et al, Activated Ras requires autophagy to maintain oxidative metabolism and tumorigenesis, Genes & Development, 25:460-470 (2011).

Hardy, S. et al, Oleate Activates Phosphatidylinositol 3-Kinase and Promotes Proliferation and Reduces Apoptosis of MDA-MB-231 Breast Cancer Cells, Whereas Palmitate Has Opposite Effects, Cancer Research, 60: 6353-6358 (2000).

Hess, D. et al, Inhibition of StearoylCoA Desaturase Activity Blocks Cell Cycle Progression and Induces Programmed Cell Death in Luna Cancer Cells, PLOS One 5(6):e11394 (2010).

Hu, Y. et al, K-rasG12V transformation leads to mitochondrial dysfunction and a metabolic switch from oxidative phosphorylation to glycolysis, Cell Research, 22(2):399-412 (2012).

Igal, A.R., Roles of StearoylCoA Desaturase-1 in the Regulation of Cancer Cell Growth, Survival and Tumorigenesis, Cancers, 3: 2462-2477 (2011).

Joyce, T. et al., A molecular signature for epithelial to mesenchymal transition in a human colon cancer cell system is revealed by large-scale microarray analysis, Clin Exp Metastasis, 26(6):569-587 (2009).

Kalaany, N.Y. and Sabatini, D.M., Tumours with PI3K activation are resistant to dietary restriction, Nature 458(7239): 725-732 (2009).

Kamphorst et al., "Liquid Chromatography High Resolution Mass Spectrometry Analysis of Fatty Acid Metabolism," Anal. Chem, vol. 83; 9114-9122 (2011).

(56) References Cited

OTHER PUBLICATIONS

Kamphorst et al., "Ras-driven cancer cells can scavenge exogenous lipids to support their proliferation," BMC Proceedings, vol. 6; 1-2 (2012).

Kannan, R. et al., Dietary Control of Lipogenesis in vivo in Host Tissues and Tumors of Mice Bearing Ehrlich Ascites Carcinoma, Cancer Research, 40:4606-4611 (1980).

Khwaja, A. et al, Matrix adhesion and Ras transformation both activate a phosphoinositide 3-OH kinase and protein kinase B/Akt cellular survival pathway, The EMBO Journal, 16(10): 2783-2793 (1997).

Kim, J-W. et al, HIF-1-mediated expression of pyruvate dehydrogenase kinase: A metabolic switch required for cellular adaptation to hypoxia, Cell Metabolism,(3):177-185 (2006).

Krypuy, M. et al, High resolution melting analysis for the rapid and sensitive detection of mutations in clinical samples: KRAS codon 12 and 13 mutations in non-small cell lung cancer, BMC Cancer, 6:295-307 (2006).

Li, C. et al, Prevention of carcinogenesis and inhibition of breast cancer tumor burden by dietary stearate, Carcinogenesis, 32(8): 1251-8 (2011).

Li, H. et al, High-throughput screening for fatty acid uptake inhibitors in humanized yeast identifies atypical antipsychotic drugs that cause dyslipidemias, J. Lipid Res., 49(1): 230-44 (2008).

Lu, W. et al, Metabolomic analysis via reversed-phase ion-pairing liquid chromatography coupled to a stand alone orbitrap mass spectrometer, Anal. Chem., 82(8): 3212-3221 (2010).

Luyimbazi, D. et al, Rapamycin regulates Stearoyl CoA Desaturase 1 Expression in Breast Cancer, Mol. Cancer Ther., 9(10):2770-2784 (2010).

Mason, P. et al, SCD1 Inhibition Causes Cancer Cell Death by Depleting Mono-Unsaturated Fatty Acids, PLOS One, 7(3):e33823 (2012).

Menendez, J.A. and Lupu, R., Fatty acid synthase and the lipogenic phenotype in cancer pathogenesis, Nat Rev Cancer, 7(10):763-777 (2007).

Metallo, C.M. et al, Reductive glutamine metabolism by IDH1 mediates lipogenesis under hypoxia, Nature, 481(7381):380-384 (2011).

Miyazaki, M. et al, Stearoyl-CoA desaturase-1 deficiency attenuates obesity and insulin resistance in leptin-resistant obese mice, Biochem Biophys Res. Commun., 380(4): 818-822 (2009).

Mullen, A.R. et al, Reductive carboxylation supports growth in tumour cells with defective mitochondria, Nature 481(7381):385-388 (2011).

Nomura, D.K. et al., Monoacylglycerol lipase regulates a fatty acid network that promotes cancer pathogenesis, Cell, 140(1): 49-61 (2010).

Papandreou, I. et al, HIF-1 mediates adaptation to hypoxia by actively downregulating mitochondrial oxygen consumption, Cell Metabolism, 3:187-197 (2006).

Roongta et al., "Cancer cell dependence on unsaturated fatty acids implicates stearoyl-CoA desaturase as a target for cancer therapy," Mol. Cancer Res., vol. 9; 1551-1561 (2011).

Santos, C. R. and Schulze, A., Lipid metabolism in cancer, the FEBS Journal minireview, 279: 2610-2623 (2012).

Sasagawa, T. et al., Abnormal serum lysophospholipids in multiple myeloma patients, Lipids, 34(1):17-21 (1998).

Schulze, A. and Harris, A.L., How cancer metabolism is tuned for proliferation and vulnerable to disruption, Nature, 491:364-373 (2012).

Shaw, R.J. and Cantley, L.C., Ras, PI(3)K and mTOR signaling controls tumour cell growth, Nature, 441:424-430 (2006).

Sheta, E.A. et al, Cell density mediated pericellular hypoxia leads to induction of HIF-1alpha via nitric oxide and Ras/MAP kinase mediated signaling pathways, Oncogene, 20:7624-7634 (2001).

Therasse, P. et al., New guidelines to evaluate the response to treatment in solid tumors, European Organization for Research and Treatment of Cancer, National Cancer Institute of the United States, National Cancer Institute of Canada, J. Natl. Cancer Inst., 92(3):205-216 (2000).

Vander Heiden, M.G. et al, Understanding the Warburg Effect: The Metabolic Requirements of Cell Proliferation, Science, 324(5930):1029-1033 (2009).

White, E., "Exploiting the bad eating habits of Ras-driven Cancers," Genes and Dev., vol. 27; 2065-2071 (2013).

Wise, D.R. et al, Hypoxia promotes isocitrate dehydrogenase-dependent carboxylation of a-ketoglutarate to citrate to support cell growth and viability, Proc. Natl. Acad. Sci., 108(49):19611-19616 (2011).

Yang, S. et al, Pancreatic cancers require autophagy for tumor growth, Genes & Development, 25:717-729 (2011).

Ying, H. et al, Oncogenic Kras Maintains Pancreatic Tumors through Regulation of Anabolic Glucose Metabolism, Cell, 149(3): 656-670 (2012).

Hagihara, K., et al., "Promising Effect of a New Ketogenic Diet Regimen in Patients with Advanced Cancer", Nutrients, 2020, 12(5) 1473, with accompanying Supplementary Materials (25 pages).

* cited by examiner

[U-$^{13}$C]-Lactate or [2-$^2$H]-Lactate

Measuring lactate-pyruvate exchange

[U-$^{13}$C]-3-HB or [3,4,4,4-$^2$H]-3-HB

Measuring 3HB-AcAc exchange

| Formulation | PicoLab (5053) | BioServ KD (S3666) |
|---|---|---|
| Carbohydrate | 62.1% | 1.8% |
| Protein | 24.7% | 4.7% |
| Fat | 13.2% | 93.5% |

KETOGENIC DIET AND KETONE SUPPLEMENTATION FOR CANCER THERAPY

RELATED APPLICATION

This application is the U.S. National Stage of International Application No. PCT/US2021/041783, filed on Jul. 15, 2021, which designates the U.S., published in English, and claims the benefit of U.S. Provisional Application No. 63/052,027, filed on Jul. 15, 2020. The entire teachings of the above applications are incorporated herein by reference.

BACKGROUND

Effective treatments for cancer are currently lacking. For example, the standard-of-care chemotherapy for metastatic pancreatic cancer, the most common type at diagnosis, affords patients a median survival of only 8.5 months.

Accordingly, there is a need for more effective strategies for treating cancer, such as pancreatic cancer.

SUMMARY

Provided herein is a method for treating a gastrointestinal cancer (e.g., pancreatic cancer, such as pancreatic ductal adenocarcinoma (PDAC)) in a subject in need thereof, comprising administering to the subject an effective amount of a chemotherapeutic regimen comprising: gemcitabine, or a pharmaceutically acceptable salt thereof; and paclitaxel, or a pharmaceutically acceptable salt thereof, wherein the subject is on a ketogenic diet (e.g., a ketogenic diet having a weight ratio of saturated fatty acids to unsaturated fatty acids of greater than 1) or a ketone supplement or both.

A method for treating a gastrointestinal cancer (e.g., pancreatic cancer) in a subject in need thereof, comprising administering to the subject an effective amount of a chemotherapeutic regimen comprising one or more of the following chemotherapeutic agents:

folinic acid, or a pharmaceutically acceptable salt thereof;

an anti-metabolite, or a pharmaceutically acceptable salt thereof;

a topoisomerase inhibitor, or a pharmaceutically acceptable salt thereof;

a taxoid, or a pharmaceutically acceptable salt thereof; and a platinum analog, or a pharmaceutically acceptable salt thereof, wherein the subject is on a ketogenic diet or a ketone supplement or both.

Also provided herein is a method of treating a cancer (e.g., a metastatic cancer, such as metastatic pancreatic cancer) in a subject in need thereof, comprising administering to the subject an effective amount of a chemotherapeutic regimen comprising one or more chemotherapeutic agents, wherein the subject is on a ketogenic diet having a weight ratio of saturated fatty acids to unsaturated fatty acids of greater than 1, or a ketone supplement, or both.

Also provided herein are chemotherapeutic regimens for use in combination with a ketogenic diet, a ketone supplement, or both for the treatment of cancer (e.g., PDAC, pancreatic cancer, a metastatic cancer, such as metastatic pancreatic cancer). Also provided herein is use of a chemotherapeutic regimen for the manufacture of a medicament for the treatment of cancer (e.g., PDAC, pancreatic cancer, a metastatic cancer, such as metastatic pancreatic cancer), wherein the chemotherapeutic regimen is designed to be used in combination with a ketogenic diet, a ketone supplement, or both. Chemotherapeutic regimens are described herein.

BRIEF DESCRIPTION OF THE DRAWINGS

The foregoing will be apparent from the following more particular description of example embodiments.

In FIGS. 2A-2H, *p<0.05, p<0.01, *p<0.001 by two-tailed Student's t test; FIGS. 2A-2G, allograft; FIG. 2H, primary.

In FIGS. 3A-3H, *p<0.05, p<0.01, *p<0.001, ****p<0.0001; FIG. 3B, Two-Way ANOVA; FIGS. 3C and 3E, Log-rank test; FIGS. 3F and 3H, One-Way ANOVA with Turkey Tests; FIG. 3G, Pearson correlation.

In FIGS. 3I-3P, *p<0.05; FIG. 3L, Two-Way ANOVA; FIGS. 3O and 3P, two-tailed Student's t test.

In FIGS. 4A-4F, ***p<0.001. FIG. 4D, Two-Way ANOVA; FIG. 4E, Log-rank test; FIG. 4F, two-tailed Student's t test.

In FIGS. 4G-4K, *p<0.05, ***p<0.001; FIG. 4I, Two-Way ANOVA; FIGS. 4H and 4J, two-tailed Student's t test.

In FIGS. 6A-6G, *p<0.05, p<0.01, *p<0.001; FIG. 6A, Two-Way ANOVA; FIGS. 6B-6G, two-tailed Student's t test.

In FIGS. 7A-7E, *p<0.05, p<0.01, *p<0.001; FIG. 7D, Two-Way ANOVA; FIGS. 7A-7C and 7E, two-tailed Student's t test.

DETAILED DESCRIPTION

Figure 1A:
FIG. 1A is a schematic illustrating exchange between circulatory lactate with tissue pyruvate and circulatory 3-hydroxybutyrate with tissue acetoacetate. $^2$H-tracers report on the exchange flux shown in the lactate schematic (and not in the 3HB schematic, because such exchange does not occur). Experimentally, whole-body exchange flux is the difference between $^2$H-tracer turnover flux and $^{13}$C-tracer turnover flux. Red, $^2$H (deuterium); blue, $^{13}$C.
Figure 1A:
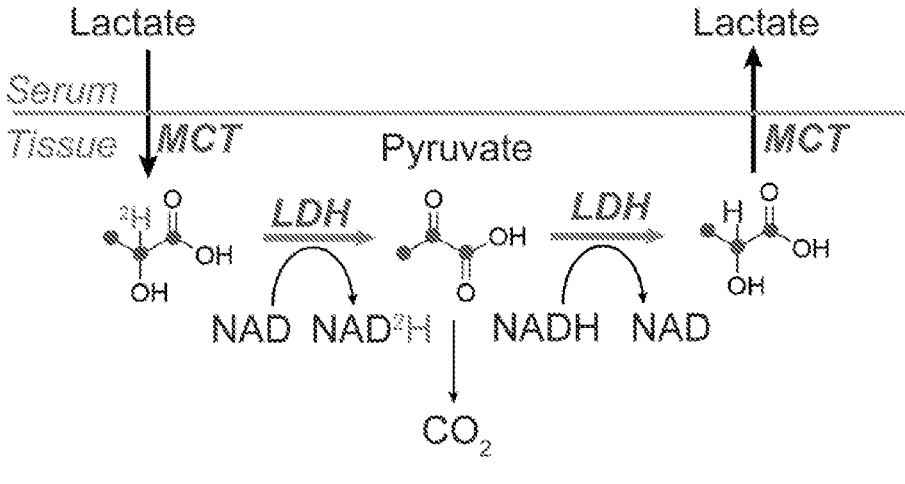
Figure 1A:
Figure 1A:
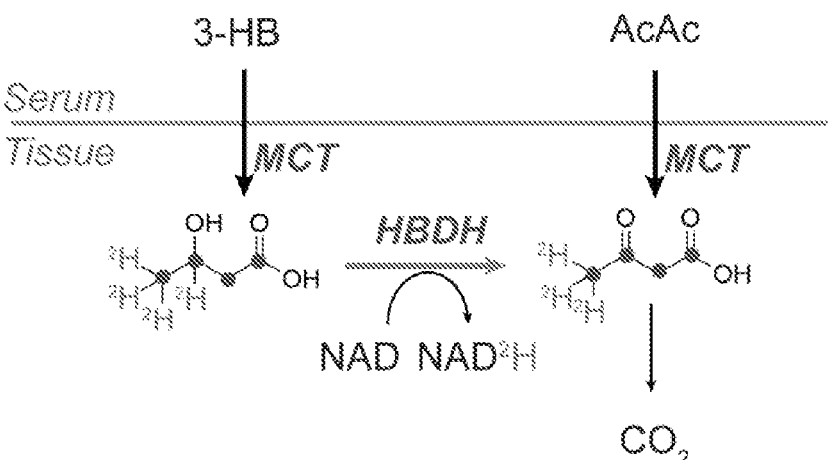
Figure 1B:
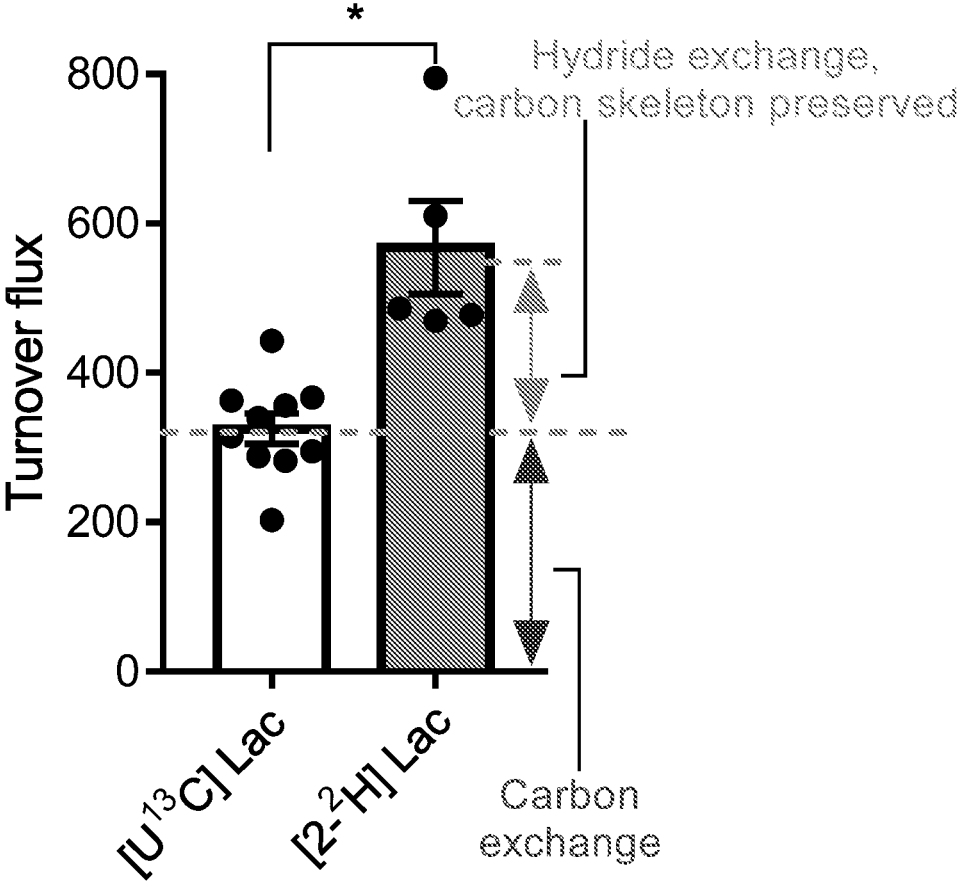
FIG. 1B shows circulatory turnover flux (units of nmole/min/gram body weight) for $^2$H versus $^{13}$C-lactate. Greater $^2$H than $^{13}$C flux indicates reversible hydride exchange. Mean±sem, n=5 for $^2$H, n=10 for $^{13}$C-lactate. *p<0.05 by two-tailed Student's t test.

A description of example embodiments follows.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

The term "about," when referring to a measurable value, such as an amount, refers to variations of ±20%, e.g., in some embodiments, ±10%, ±5%, ±1% or ±0.1% from the specified value.

Provided herein are methods for treating cancer (e.g., pancreatic ductal adenocarcinoma (PDAC), pancreatic cancer, a metastatic cancer, such as metastatic pancreatic cancer) in a subject in need thereof, wherein the subject is on a ketogenic diet (e.g. a ketogenic diet having a weight ratio of saturated fatty acids to unsaturated fatty acids of greater than 1), a ketone supplement, or both. In some embodiments, the subject is on a ketogenic diet but not a ketone supplement. In some embodiments, the subject is on a ketone supplement but not a ketogenic diet. In some embodiments, the subject is on a ketogenic diet and a ketone supplement.

A ketogenic diet is a diet that is high in fat, and contains adequate or moderate protein and low or no carbohydrates. Traditional ketogenic diets have a fat(s) to protein(s) and carbohydrate(s) ratio of 4:1 (by weight), and consist of about 90% fat(s), about 8% protein(s) and about 2% carbohydrate(s) (based on total calories). Clinically used ketogenic diets typically have a fat(s) to protein(s) and carbohydrate(s) ratio of at least 2:1 (e.g., about 3:1) (by weight), meaning at least 80% of total calories come from fat(s). Some ketogenic diets consist of 65-85% (e.g., 75%) fat(s), 10-20% (e.g., 20%) protein(s), and 5% carbohydrate(s) (based on total calories). Therapeutic ketosis, the goal of at least therapeutic ketogenic diets, is achieved at plasma ketone body levels in the range of from about 0.5 mM to about 7 mM (e.g., from about 1 mM to about 7 mM).

In some embodiments, a ketogenic diet comprises fat, protein and, optionally, carbohydrate, and the weight ratio of fat to the sum of protein and carbohydrate is at least or about 2, e.g., at least or about: 3, 4, 5, 6, 7, 8, 9 or 10. In some embodiments, a ketogenic diet contains less than 10% or 8% or 5% (e.g., less than 4%, less than 3%, less than 2.5%, less than 2% or less than 1%) by weight carbohydrate(s).

In some embodiments, a ketogenic diet contains from about 55% to about 95%, from about 65% to about 90%, from about 65% to about 85%, from about 75% to about 85%, from about 85% to about 95%, from about 90% to about 95% or about: 55%, 60%, 65%, 70% 75%, 80%, 85%, 90%, 91%, 92%, 93%, 94% or 95% fat(s) based on total calories. In some embodiments, a ketogenic diet contains less than or about: 20%, 15%, 10%, 5%, 4%, 3%, 2% or 1% carbohydrate(s) based on total calories. In some embodiments, a ketogenic diet contains from about 2.5% to about 35%, from about 2.5% to about 10%, from about 4% to about 10%, from about 5% to about 10%, from about 10% to about 20% or from about 20% to about 35% protein(s) based on total calories. In some embodiments, a ketogenic diet contains from about 85% to about 95% (e.g., about 93%) fat(s) based on total calories, from about 2.5% to about 10% (e.g., about 5%) protein(s) based on total calories and less than about 5% (e.g., less than 5%, such as about 2%) carbohydrate(s) based on total calories. In some embodiments, a ketogenic diet contains greater than about 80% (e.g., about 80% to about 95%, or about 90%) fat(s) based on total calories, from about 2.5% to about 10% (e.g., about 8%) protein(s) based on total calories and less than about 5% (e.g., less than 5%, such as about 2%) carbohydrate(s) based on total calories.

It has been found that the nature of the fat(s) being consumed in a ketogenic diet is a relevant attribute of the diet. Dietary fat(s) is largely in the form of triglycerides, with some fat(s) also in the form of other lipids. The fatty acid tails of triglycerides and other lipids can vary in length and/or saturation. In some embodiments, the ratio by weight or by molarity or by calorie (e.g., by weight) of saturated fatty acids to unsaturated fatty acids is greater than or about 1, 2, 3, 4, 5, 8, 10, 15, 20, 25, 30, 35, 40, 45, or 50. For example, in some embodiments, the weight ratio of saturated fatty acids to unsaturated fatty acids is greater than 1. In some embodiments, the fatty acids are substantially saturated, with the ratio by weight or by molarity or by calorie (e.g., by weight) of saturated to unsaturated fatty acids greater than about: 0.5, 0.6, 0.75, 1, 1.2, 1.5, 1.75, 2, 2.5, 3, 4, 5 or more. In some embodiments, the diet contains, e.g., less than about: 40%, 30%, 20%, 15%, 10%, or 5% by weight or by calorie or by molarity (e.g., by weight) polyunsaturated and/or monounsaturated fatty acids. In some embodiments, the fatty acids are substantially saturated, e.g., at least 10%, 20%, 30%, 40%, 50%, 60%, 70%, 80%, or 90% of dietary fat(s) by calorie, by weight, or by molarity (e.g., by weight) are in the form of saturated fatty acids, and have a length in the range of C8 to C18, C8 to C16, C8 to C14, C8 to C12, C10 to C12, C10 to C16, C12 to C16, C12 to C14, or C12. In some embodiments, the fatty acids are substantially saturated, e.g., at least 10%, 20%, 30%, 40%, 50%, 60%, 70%, 80%, or 90% of dietary fat(s) by calorie, by weight, or by molarity (e.g., by weight) is in the form of saturated fatty acids, and have a length in the range of C16 to C30, C16 to C22, C18 to C30, C20 to C30, C16 to C20, C16 to C18, or C16. In some embodiments, the ratio of C16:0 (where the number after the colon refers to the degree of desaturation) to C16:1 is in the range of from 2 to 4 or from 3 to 6. In some embodiments, the ratio of (C16:0+C18:0) to (C16:1+C18:1) is in the range of from 1 to 4 or from 2 to 4. In some embodiments, the most prevalent fatty acid tail in the diet is C10:0, C12:0, C14:0, C16:0, and/or C18:0. In some embodiments, the fraction of fatty acid tails that are C18:1, or are C18:2, or are either C18:1 or C18:2 is less than about: 40%, 30%, 20%, 15%, 10%, 5%, or 2.5%.

A ketone supplement is an exogenous source of ketone bodies, such as acetone, acetoacetic acid, D-beta hydroxybutyric acid, beta-ketopentanoic acid and beta-hydroxypentanoic acid, or an ester or covalent multimer of any of the foregoing, or a salt (e.g., pharmaceutically acceptable salt) of any of the foregoing. A ketone supplement is typically in the form of a nutritional supplement or food substitute. The ketone supplement may, but need not, contain a ketone body, or a pharmaceutically acceptable salt thereof, so long as the material in the supplement can be converted into ketone bodies (e.g., by metabolism, such as ketogenesis in the liver). In some embodiments, a ketone supplement is a ketone ester or an acid anhydride of a ketone body, such as acetoacetic acid, D-beta hydroxybutyric acid, beta-ketopentanoic acid or beta-hydroxypentanoic acid. Specific examples of ketone supplements include, R(3)-hydroxybutyryl-R(3)-hydroxybutyrate, digestible ketone body polymers (including dimers), such as poly-beta-hydroxybutyrate, 1,3-butanediol monoester of beta-hydroxybutyrate and 1,3-butanediol acetoacetate ester, or a pharmaceutically acceptable salt thereof.

Suitable dosages of ketone supplements (e.g., digestible ketone body polymers or esters of beta-hydroxybutyrate) for humans include from about 50 g/day to about 200 g/day, e.g., from about 100 g/day to about 150 g/day (or from about 1 g/kg/day to about 2 g/kg/day), from about 50 g/day to about 150 g/day or from about 100 g/day to about 200 g/day, taken, for example, in one, two, three, four, five or more (e.g., three) doses. Suitable dosages of ketone supplements for other mammals, such as mice, include from about 1.5 Kcal/day to about 4 Kcal/day (e.g., about 1.7 Kcal/day or about 17% of total calories).

In some embodiments, the method comprises maintaining the subject on the ketogenic diet, the ketone supplement, or both (e.g., administering to the subject the ketogenic diet, the ketone supplement, or both, e.g., an effective amount of the ketogenic diet, the ketone supplement, or both). In alternative or further embodiments, the method comprises instructing the subject to the consume the ketogenic diet, the ketone supplement, or both (e.g., an effective amount of the ketogenic diet, the ketone supplement, or both).

In some embodiments, the method comprises administering to the subject an effective amount of a chemotherapeutic regimen comprising one or more chemotherapeutic agents. In some embodiments, the method further comprises maintaining the subject on the ketogenic diet, the ketone supplement, or both (e.g., administering to the subject the ketogenic diet, the ketone supplement, or both, e.g., an effective amount of the ketogenic diet, the ketone supplement, or both). In some embodiments, the method further comprises instructing the subject to the consume the ketogenic diet, the ketone supplement, or both (e.g., an effective amount of the ketogenic diet, the ketone supplement, or both).

In some embodiments, the subject starts on the ketogenic diet or ketone ester supplement or both prior to commencement of the chemotherapeutic regimen and/or the subject continues on the ketogenic diet or ketone ester supplement or both after termination of the chemotherapeutic regimen.

In some embodiments, the subject starts on the ketogenic diet or ketone supplement or both and the chemotherapeutic regimen at approximately the same time. In some embodiments, the subject starts on the ketogenic diet or ketone supplement or both after commencement of the chemotherapeutic regimen.

In some embodiments, the subject continues on the ketogenic diet or ketone supplement or both after termination of the chemotherapeutic regimen. In some embodiments, the subject continues on the ketogenic diet or ketone supplement or both until termination of the chemotherapeutic regimen. In some embodiments, the subject discontinues the ketogenic diet or ketone supplement or both and the chemotherapeutic regimen at approximately the same time. In some embodiments, the subject discontinues the ketogenic diet or ketone supplement or both prior to termination of the chemotherapeutic regimen.

In some embodiments, the subject is on the ketogenic diet, the ketone ester supplement or both for a time period of at least 2 weeks, e.g., at least 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed.

Examples of chemotherapeutic agents for use individually or in combination (e.g., with one another or another chemotherapeutic agent disclosed herein) in the chemotherapeutic regimens described herein include alkylating agents, such as thiotepa and cyclophosphamide (CYTOXAN™), and temozolomide; alkyl sulfonates, such as busulfan, improsulfan and piposulfan; aziridines, such as benzodopa, carboquone, meturedopa, and uredopa; ethylenimines and methylamelamines, such as altretamine, triethylenemelamine, trietylenephosphoramide, triethylenethiophosphaoramide and trimethylolomelamine; acetogenins, such as bullatacin and bullatacinone; camptothecins, including the synthetic analogue topotecan; bryostatin; callystatin; CC-1065, including its adozelesin, carzelesin and bizelesin analogues; cryptophycins, such as cryptophycin 1 and cryptophycin 8; dolastatin; duocarmycin, including the synthetic analogues, KW-2189 and CBI-TMI; eleutherobin; pancratistatin; sarcodictyins; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosoureas, such as carmustine, chlorozotocin, fotemustine, lomustine, nimustine, and ranimustine; antibiotics, such as the enediyne antibiotics (e.g., calicheamicin, especially calicheamicin gamma 1 and calicheamicin theta I, see, e.g., *Angew Chem. Intl. Ed. Engl.* 33:183-186 (1994); dynemicin, such as dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, methotrexate, pemetrexed, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, floxuridine, and 5-FU; androgens, such as calusterone, dromostanolone propionate, epitiostanol, mepitiostane, and testolactone; anti-adrenals, such as aminoglutethimide, mitotane, and trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilones; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2', 2"-trichlorotriethylamine; trichothecenes, such as T-2 toxin, verracurin A, roridin A and anguidine; urethan; vindesine; dacarbazine; mannomustine; mitobronitol; mitolactol; pipobroman; gacytosine; arabinoside ("Ara-C"); cyclophosphamide; thiotepa; taxoids, such as paclitaxel (e.g., TAXOL™, Bristol-Myers Squibb Oncology, Princeton, N.J.; nab-paclitaxel, such as the nanoparticle albumin-bound form of paclitaxel sold as ABRAXANE®) and doxetaxel (TAXOTERE®, Rhone-Poulenc Rorer, Antony, France); chlorambucil; gemcitabine; 6-thioguanine; mercaptopurine; methotrexate; folinic acid; platinum analogs such as cisplatin, oxaliplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitors, such as irinotecan and RFS 2000; difluoromethylomithine (DFMO); retinoic acid; and capecitabine; or a pharmaceutically acceptable salt, acid or derivative of any of the above. Further examples of chemotherapeutic agents for use individually or in combination (e.g., with one another or another chemotherapeutic agent disclosed herein) in the chemotherapeutic regimens described herein include anti-hormonal agents that act to regulate or inhibit hormone action on tumors, such as anti-estrogens including, for example, tamoxifen, raloxifene, aromatase inhibiting 4(5)-imidazoles, 4-hydroxytamoxifen, trioxifene, keoxifene, LY117018, onapristone, and toremifene (Fareston); anti-androgens, such as flutamide, nilutamide, bicalutamide, leuprolide, and goserelin; and siRNA, or a pharmaceutically acceptable salt, acid or derivative of any of the above.

Examples of chemotherapeutic agents particularly useful for the treatment of gastrointestinal cancer (e.g., pancreatic cancer) include oxaliplatin, carboplatin, irinotecan, 5-fluorouracil, folinic acid, gemcitabine, cisplatin, paclitaxel (e.g., nab-paclitaxel), capecitabine, erlotinib, docetaxel, fluoropyrimidine, olaparib, entrectinib and larotrectinib. In some embodiments, a chemotherapeutic regimen comprises, consists essentially of or consists of one or more (e.g., 1, 2, 3, 4 or 5) of the following chemotherapeutic agents: oxaliplatin, carboplatin, irinotecan, 5-fluorouracil, folinic acid, gemcitabine, cisplatin, paclitaxel (e.g., nab-paclitaxel), capecitabine, erlotinib, docetaxel, fluoropyrimidine, olaparib, entrectinib and larotrectinib, or a pharmaceutically acceptable salt of the foregoing.

In some embodiments, the chemotherapeutic regimen is the standard of care for a particular cancer (e.g., PDAC, pancreatic cancer, a metastatic cancer, such as metastatic pancreatic cancer). For example, FOLFIRINOX, a chemotherapeutic regimen consisting of a 2-hour intravenous infusion (IVF) of oxaliplatin, 85 mg/m$^2$, followed by a 90-minute IVF of irinotecan, 180 mg/m$^2$, followed by a 2-hour IVF of folinic acid, 400 mg/m$^2$, followed by a bolus of 5-fluorouracil 400 mg/m$^2$ and a 46-hour IVF of 5-fluorouracil, 2400 mg/m$^2$, and the combination of gemcitabine and nab-paclitaxel are widely considered the first-line, standard of care for pancreatic cancer. Modified FOLFIRINOX, a chemotherapeutic regimen consisting of intravenous infusion of oxaliplatin, 65 mg/m$^2$; irinotecan, 150 mg/m$^2$; folinic acid, 200 mg/m$^2$; and 5-fluorouracil, 2400 mg/m$^2$, repeated every 2 weeks, is also sometimes employed as a standard of care for pancreatic cancer.

In some embodiments, a chemotherapeutic regimen (e.g., for the treatment of pancreatic cancer, such as pancreatic ductal adenocarcinoma) comprises, consists essentially of or consists of an antimetabolite (e.g., gemcitabine, or a pharmaceutically acceptable salt thereof), and a taxoid (e.g., paclitaxel, such as nab-paclitaxel, or a pharmaceutically acceptable salt thereof). In some embodiments, a chemotherapeutic regimen (e.g., for the treatment of pancreatic cancer, such as pancreatic ductal adenocarcinoma) comprises, consists essentially of or consists of the following chemotherapeutic agents: an antimetabolite (e.g., gemcitabine, or a pharmaceutically acceptable salt thereof), and a taxoid (e.g., paclitaxel, such as nab-paclitaxel, or a pharmaceutically acceptable salt thereof). In some embodiments, a chemotherapeutic regimen (e.g., for the treatment of pancreatic cancer, such as pancreatic ductal adenocarcinoma) comprises, consists essentially of or consists of two of the following three chemotherapeutic agents: an antimetabolite (e.g., gemcitabine, or a pharmaceutically acceptable salt thereof), a taxoid (e.g., paclitaxel, such as nab-paclitaxel, or a pharmaceutically acceptable salt thereof), and a platinum analog (e.g., cisplatin, or a pharmaceutically acceptable salt thereof). In some embodiments, a chemotherapeutic regimen (e.g., for the treatment of pancreatic cancer, such as pancreatic ductal adenocarcinoma) comprises, consists essentially of or consists of an antimetabolite (e.g., gemcitabine, or a pharmaceutically acceptable salt thereof), a taxoid (e.g., paclitaxel, such as nab-paclitaxel, or a pharmaceutically acceptable salt thereof), and a platinum analog (e.g., cisplatin, or a pharmaceutically acceptable salt thereof).

Examples of anti-metabolites include 5-fluorouracil, 6-mercaptopurine, capecitabine, cytarabine, floxuridine, fludarabine, gemcitabine, hydroxycarbamide, methotrexate and pemetrexed, or a pharmaceutically acceptable salt of the foregoing. Examples of taxoids include paclitaxel, docetaxel and cabazitaxel, or a pharmaceutically acceptable salt of the foregoing. Examples of platinum analogs include carboplatin, cisplatin and oxaliplatin, or a pharmaceutically acceptable salt of the foregoing.

In some embodiments, a chemotherapeutic regimen (e.g., for the treatment of pancreatic cancer, such as advanced pancreatic cancer) comprises, consists essentially of or consists of one or more (e.g., two, three, four) of the following chemotherapeutic agents: folinic acid, or a pharmaceutically acceptable salt thereof; an anti-metabolite (e.g., 5-fluorouracil, gemcitabine, or a pharmaceutically acceptable salt thereof); a topoisomerase inhibitor (e.g., a topoisomerase I inhibitor, such as irinotecan, or a pharmaceutically acceptable salt thereof); a taxoid (e.g., paclitaxel, such as nab-paclitaxel, or a pharmaceutically acceptable salt thereof); and a platinum analog (e.g., oxaliplatin, or a pharmaceutically acceptable salt thereof). In some embodiments, a chemotherapeutic regimen (e.g., for the treatment of pancreatic cancer, such as advanced pancreatic cancer) comprises, consists essentially of or consists of folinic acid, or a pharmaceutically acceptable salt thereof; an anti-metabolite (e.g., 5-fluorouracil, or a pharmaceutically acceptable salt thereof); a topoisomerase inhibitor (e.g., a topoisomerase I inhibitor, such as irinotecan, or a pharmaceutically acceptable salt thereof); and a platinum analog (e.g., oxaliplatin, or a pharmaceutically acceptable salt thereof). In some embodiments, the chemotherapeutic regimen is FOLFIRINOX. In some embodiments, the chemotherapeutic regimen is modified FOLFIRINOX.

Examples of topoisomerase inhibitors include topoisomerase I inhibitors, such as irinotecan and topotecan, or a pharmaceutically acceptable salt of the foregoing, and topoisomerase II inhibitors, such as etoposide and teniposide, or a pharmaceutically acceptable salt of the foregoing.

In some embodiments, a chemotherapeutic regimen (e.g., for the treatment of pancreatic cancer, such as advanced pancreatic cancer) comprises, consists essentially of or consists of an anthracycline (e.g., doxorubicin, or a pharmaceutically acceptable salt thereof). Examples of anthracyclines include daunorubicin, doxorubicin, epirubicin and idarubicin, or a pharmaceutically acceptable salt of the foregoing.

An agent, such as a ketone supplement or chemotherapeutic agent described herein, can be in the form of a free base or a salt (e.g., a pharmaceutically acceptable salt). As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts include salts include pharmaceutically acid addition salts and pharmaceutically acceptable base addition salts.

Pharmaceutically acceptable acid addition salts are salts derived from suitable inorganic and organic acids. Examples of salts derived from suitable acids include salts of an amino group formed with inorganic acids, such as hydrochloric acid, hydrobromic acid, phosphoric acid, sulfuric acid and perchloric acid, or with organic acids, such as acetic acid, oxalic acid, maleic acid, tartaric acid, citric acid, succinic acid or malonic acid, or by using other methods known in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Pharmaceutically acceptable base addition salts are salts derived from suitable inorganic and organic bases. Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine and picoline, or $N^+((C_1\text{-}C_4)alkyl)_4$ salts. Representative alkali or alkaline earth metal salts include sodium, lithium, potassium, calcium, magnesium, barium and the like. Further pharmaceutically acceptable base salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

An agent, such as a ketone supplement or a chemotherapeutic agent described herein, or a pharmaceutically acceptable salt thereof, can be provided in the form of a pharmaceutical composition, comprising one or more agents and a pharmaceutically acceptable carrier. The compositions can be used in the methods described herein, e.g., to supply an agent described herein.

"Pharmaceutically acceptable carrier" refers to a nontoxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

An agent, such as a ketone supplement or a chemotherapeutic agent described herein, or a pharmaceutically acceptable salt thereof, or a composition comprising the same can be administered via a variety of routes of administration, including, for example, via oral, dietary, nasal, buccal, vaginal, topical, transdermal, rectal, parenteral (e.g., intra-arterial, intravenous, intramuscular, subcutaneous, intradermal), intravenous and inhalation (e.g., intrabronchial, intranasal or oral inhalation, intranasal drops) routes of administration. The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Administration can be local or systemic as indicated. The preferred mode of administration can vary depending on the particular agent chosen. For example, ketone supplements are often administered orally due to the typically large doses at which they are administered. Thus, in some embodiments, a ketone supplement or a composition comprising a ketone supplement is administered orally.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

An agent can also be in micro-encapsulated form with one or more excipients, as noted above. In such solid dosage forms, the agent can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, an agent can be provided in an extended (or "delayed" or "sustained") release composition. This delayed-release composition comprises the agent in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered subcutaneously, intraperitoneally or intravenously. Compositions described herein for intravenous, subcutaneous, or intraperitoneal injection may contain an isotonic vehicle such as sodium chloride injection, Ringer's injection, dextrose injection, dextrose and sodium chloride injection, lactated Ringer's injection, or other vehicles known in the art.

Compositions described herein can also be administered in the form of suppositories for rectal administration. These can be prepared by mixing a compound described herein with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation, for example, for the treatment of asthma. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition, for example, consequences for red blood cells.

The amount of an agent that can be combined with the carrier materials to produce a composition in a single dosage form will vary depending, for example, upon the subject treated, the particular mode of administration and the activity of the agent employed. Preferably, compositions should be formulated so that a dosage of from about 0.01 mg/kg to about 100 mg/kg body weight/day of the agent can be administered to a subject receiving the composition.

The desired dose may conveniently be administered in a single dose or as multiple doses administered at appropriate intervals such that, for example, the agent can be administered 1, 2, 3, 4, 5, 6 or more times per day. The daily dose can be divided, especially when relatively large amounts are administered, or as deemed appropriate, into several, for example, 2, 3, 4, 5, 6 or more, administrations.

It should also be understood that a specific dosage and treatment regimen for any particular patient will depend upon a variety of factors, including, for example, the activity of the specific agent employed, the age, body weight, general health, sex, diet, time of administration, rate of excretion, drug combination, the judgment of the treating physician and the severity of the particular disease being treated. The amount of an agent in the composition will also depend upon the particular agent in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

The compositions described herein (e.g., compositions comprising one or more chemotherapeutic agents) can, for example, be administered by injection, intravenously, intraarterially, intraocularly, intravitreally, subdermally, orally, buccally, nasally, transmucosally, topically, in an ophthalmic preparation, or by inhalation, with a dosage ranging from about 0.5 mg/kg to about 5,000 mg/kg (e.g., 1 mg/kg to about 1,000 mg/kg, from about 100 mg/kg to about 1,000 mg/kg, from about 0.5 mg/kg to about 500 mg/kg) of body weight or, alternatively, in a dosage ranging from about 1 mg/dose to about 100 g/dose (e.g., from about 10 mg/dose to about 10 g dose, from about 1 g/dose to about 50 g/dose, from about 1 mg/dose to about 1,000 mg/dose), every 4 to 120 hours, or according to the requirements of the particular drug. Typically, the compositions will be administered from about 1 to about 6 (e.g., 1, 2, 3, 4, 5 or 6) times per day or, alternatively, as an infusion (e.g., a continuous infusion).

The amount of active ingredient that can be combined with a carrier material to produce a single dosage form will vary depending upon the host treated and the particular mode of administration. A typical preparation will contain from about 1% to about 95%, from about 2.5% to about 95% or from about 5% to about 95% active compound (w/w). Alternatively, a preparation can contain from about 20% to about 80% active compound (w/w).

"Treating," as used herein, refers to taking steps to deliver a therapy to a subject, such as a mammal, in need thereof (e.g., as by administering to a mammal one or more therapeutic agents). "Treating" includes inhibiting the disease or condition (e.g., as by slowing or stopping its progression or causing regression of the disease or condition), and relieving the symptoms resulting from the disease or condition.

As used herein, "subject" refers to a mammal (e.g., human, such as an aged human (e.g., a human aged 60 or greater, 65 or greater, or greater than 65), non-human primate, cow, sheep, goat, horse, dog, cat, rabbit, guinea pig, rat, mouse). In a particular embodiment, the subject is a human.

An "effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, an effective amount may be administered in one or more administrations. An effective amount may vary according to factors such as disease state, age, sex, and weight of a subject, mode of administration and the ability of a therapeutic agent, or combination of therapeutic agents, to elicit a desired response in a subject.

An effective amount of an agent to be administered can be determined by a clinician of ordinary skill using the guidance provided herein and other methods known in the art. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Doses lower or higher than those recited herein may be required. Specific dosage and treatment regimens for any particular subject will depend upon a variety of factors, for example, the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. Determining the dosage for a particular agent, subject and disease is well within the abilities of one of skill in the art. Preferably, the dosage does not cause or produces minimal adverse side effects.

Cancers treatable according to the methods described herein include solid tumor cancer and hematologic cancers (both adult and pediatric). Thus, in some embodiments, the cancer comprises a solid tumor. Examples of solid tumor cancers include lung cancer (e.g., non-small cell lung cancer), mesothelioma, breast cancer, colon cancer, liver cancer, colorectal cancer, stomach cancer, prostate cancer, pancreatic cancer, ovarian cancer, uterine cancer, solid tumors of the uterus or female genital tract (e.g., uterine cancer), bladder cancer, head and neck cancers, brain cancer (e.g., glioblastoma), and trophoblastic neoplasms. In some embodiments, the cancer is pancreatic cancer. In some embodiments, the cancer is colorectal cancer. In some embodiments, the cancer is colon cancer. In some embodiments, the cancer is glioblastoma multiforme.

In some embodiments, the cancer is a hematologic cancer. Examples of hematologic cancers include leukemia (e.g., acute lymphoblastic leukemia (ALL), acute myeloid leukemia (AML) such as FLT3 inhibitor-resistant AML or AML with high mTORC1 expression and/or activity, chronic lymphocytic leukemia (CLL), chronic myelogenous leukemia (CML), acute monocytic leukemia (AMoL)), lymphoma (e.g., non-Hodgkin's lymphoma or Hodgkin's lymphoma), and multiple myeloma. In certain embodiments, the cancer is a leukemia, preferably a T-cell leukemia, such as T-cell lymphoblastic leukemia. In certain embodiments, the cancer is a B-cell leukemia. In certain embodiments, the cancer is a lymphoma, preferably a T-cell lymphoma. In certain embodiments, the cancer is a B-cell lymphoma, for example, diffuse large B-cell lymphoma or a Burkitt lymphoma.

Specific examples of cancers treatable according to the methods described herein include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some embodiments, the cancer is a metastatic cancer.

In some embodiments, the cancer is previously untreated. In some embodiments, the cancer is previously treated.

In some embodiments, the cancer is a Ras-associated cancer. Examples of Ras-associated cancers include pancreatic cancer, non-small cell lung cancer, colorectal cancer, bladder cancer, kidney cancer, thyroid cancer, melanoma, hepatocellular carcinoma and a hematologic cancer. In some embodiments, the cancer is a Ras-associated cancer other than lung cancer.

In some embodiments, the cancer is a gastrointestinal cancer. Examples of gastrointestinal cancers include pancreatic cancer, colon cancer, gallbladder cancer, liver cancer, esophageal cancer, anal cancer, biliary tract cancer, small intestine cancer, gastrointestinal stromal tumors, ovarian cancer, rectal cancer, colorectal cancer, stomach cancer, throat cancer, thyroid cancer and parathyroid cancer. In some embodiments, the cancer is pancreatic cancer or colon cancer.

In some embodiments, the cancer is pancreatic cancer (e.g., advanced pancreatic cancer). In some embodiments, the cancer is pancreatic ductal adenocarcinoma (e.g., metastatic pancreatic ductal adenocarcinoma). In some embodiments, the pancreatic cancer is previously untreated. In some embodiments, the pancreatic cancer is previously treated.

One embodiment provides a method for treating a gastrointestinal cancer (e.g., pancreatic cancer; PDAC, such as metastatic PDAC) in a subject in need thereof, comprising administering to the subject an effective amount of a chemotherapeutic regimen comprising at least two of the following three chemotherapeutic agents: gemcitabine, or a pharmaceutically acceptable salt thereof; a taxoid, or a pharmaceutically acceptable salt thereof; and a platinum analog, or a pharmaceutically acceptable salt thereof, wherein the subject is on a ketogenic diet (e.g., a ketogenic diet having a weight ratio of saturated fatty acids to unsaturated fatty acids of greater than 1), or a ketone supplement, or both. In some embodiments, the chemotherapeutic regimen comprises, consists essentially of or consists of at least two of the following three chemotherapeutic agents: gemcitabine, or a pharmaceutically acceptable salt thereof; paclitaxel, or a pharmaceutically acceptable salt thereof; and cisplatin, or a pharmaceutically acceptable salt thereof. In some embodiments, the chemotherapeutic regimen comprises, consists essentially of or consists of gemcitabine, or a pharmaceutically acceptable salt thereof; and paclitaxel, or a pharmaceutically acceptable salt thereof (e.g., nab-paclitaxel). In some embodiments, the chemotherapeutic regimen comprises, consists essentially of or consists of gemcitabine, or a pharmaceutically acceptable salt thereof; and cisplatin, or a pharmaceutically acceptable salt thereof. In some embodiments, the chemotherapeutic regimen comprises, consists essentially of or consists of gemcitabine, or a pharmaceutically acceptable salt thereof; paclitaxel, or a pharmaceutically acceptable salt thereof (e.g., nab-paclitaxel); and cisplatin, or a pharmaceutically acceptable salt thereof.

In some embodiments of the chemotherapeutic regimens described herein, particularly those comprising gemcitabine, or a pharmaceutically acceptable salt thereof, and paclitaxel, or a pharmaceutically acceptable salt thereof (e.g., nab-paclitaxel), the chemotherapeutic regimen is administered once weekly. For example, in some embodiments, the chemotherapeutic regimen is administered once weekly for two consecutive weeks on a 21-day cycle (e.g., on days 1 and 8), and is not administered during the third week of the 21-day cycle. Alternatively, in some embodiments, the chemotherapeutic regimen is administered once weekly for three consecutive weeks on a 28-day cycle (e.g., on days 1, 8 and 15), and is not administered during the fourth week of the 28-day cycle.

In some embodiments of the chemotherapeutic regimens described herein comprising gemcitabine, or a pharmaceutically acceptable salt thereof, particularly those comprising gemcitabine, or a pharmaceutically acceptable salt thereof, paclitaxel, or a pharmaceutically acceptable salt thereof (e.g., nab-paclitaxel), and optionally a platinum analog (e.g., cisplatin), or a pharmaceutically acceptable salt thereof, about 1,000 mg/m$^2$ gemcitabine, or a pharmaceutically acceptable salt thereof, is administered to the subject per day.

In some embodiments of the chemotherapeutic regimens described herein comprising paclitaxel, or a pharmaceutically acceptable salt thereof (e.g., nab-paclitaxel), particularly those comprising gemcitabine, or a pharmaceutically acceptable salt thereof, paclitaxel, or a pharmaceutically acceptable salt thereof, and optionally a platinum analog (e.g., cisplatin), or a pharmaceutically acceptable salt thereof, about 125 mg/m$^2$ paclitaxel, or a pharmaceutically acceptable salt thereof (e.g., nab-paclitaxel), is administered to the subject per day.

In some embodiments of the chemotherapeutic regimens described herein comprising cisplatin, or a pharmaceutically acceptable salt thereof, particularly those comprising gemcitabine, or a pharmaceutically acceptable salt thereof, paclitaxel, or a pharmaceutically acceptable salt thereof (e.g., nab-paclitaxel), and cisplatin, or a pharmaceutically acceptable salt thereof, about 25 mg/m$^2$ cisplatin, or a pharmaceutically acceptable salt thereof, is administered to the subject per day.

Another embodiment provides a method for treating a gastrointestinal cancer (e.g., pancreatic cancer) in a subject in need thereof, comprising administering to the subject an effective amount of a chemotherapeutic regimen comprising at least one (e.g., at least two, two, three, four) of the following chemotherapeutic agents: folinic acid, or a pharmaceutically acceptable salt thereof; an anti-metabolite (e.g., 5-fluorouracil, gemcitabine, or a pharmaceutically acceptable salt thereof); a topoisomerase inhibitor (e.g., a topoisomerase I inhibitor, such as irinotecan, or a pharmaceutically acceptable salt thereof); a taxoid (e.g., paclitaxel, such as nab-paclitaxel, or a pharmaceutically acceptable salt thereof); and a platinum analog (e.g., oxaliplatin, or a pharmaceutically acceptable salt thereof), wherein the subject is on a ketogenic diet (e.g., a ketogenic diet having a weight ratio of saturated fatty acids to unsaturated fatty acids of greater than 1), a ketone supplement, or both. In some embodiments, the chemotherapeutic regimen comprises, consists essentially of or consists of at least two (e.g., two, three, four) of the following chemotherapeutic agents: folinic acid, or a pharmaceutically acceptable salt thereof; an anti-metabolite (e.g., 5-fluorouracil), or a pharmaceutically acceptable salt thereof; a topoisomerase inhibitor (e.g., irinotecan), or a pharmaceutically acceptable salt thereof; and a platinum analog (e.g., oxaliplatin), or a pharmaceutically acceptable salt thereof. In some embodiments, the chemotherapeutic regimen comprises, consists essentially of or consists of the following chemotherapeutic agents: folinic acid, or a pharmaceutically acceptable salt thereof; 5-fluorouracil, or a pharmaceutically acceptable salt thereof; irinotecan, or a pharmaceutically acceptable salt thereof; and oxaliplatin, or a pharmaceutically acceptable salt thereof.

Another embodiment provides a method for treating a gastrointestinal caner (e.g., pancreatic cancer) in a subject in need thereof, comprising administering to the subject an effective amount of a chemotherapeutic regimen comprising doxorubicin, or a pharmaceutically acceptable salt thereof, wherein the subject is on a ketogenic diet (e.g., a ketogenic diet having a weight ratio of saturated fatty acids to unsaturated fatty acids of greater than 1), a ketone supplement, or both.

The chemotherapeutic regimens and/or chemotherapeutic agents described herein can also be administered in combination with one or more other therapies (e.g., radiation therapy, immunotherapy). When administered in combination with one or more other therapies, the chemotherapeutic regimens and/or chemotherapeutic agents described herein can be administered before, after or concurrently with the other therapy.

The chemotherapeutic agents and/or regimens can also be administered in combination with radiation therapy. Thus, in some embodiments, a method further comprises administering to the subject radiation therapy (e.g., an effective amount of radiation therapy).

The chemotherapeutic agents and/or regimens can also be administered in combination with an immunotherapy. Thus, in some embodiments, a method further comprises administering to the subject an immunotherapy (e.g., an effective amount of an immunotherapy).

Examples of immunotherapies include immune checkpoint inhibitors, agonist CD-40 antibodies, T-cell transfer therapy (e.g., CAR T-cell therapy, tumor infiltrating lymphocytes (TIL) therapy), NK cell transfer therapy, monoclonal antibodies, cancer treatment vaccines and immune system modulators. Examples of immune checkpoint inhibitors include inhibitors of CTLA-4, such as ipilimumab; inhibitors of PD-1, such as pembrolizumab, nivolumab, and cemiplimab; and inhibitors of PD-L1, such as atezolizumab, avelumab, and durvalumab. Examples of T-cell transfer therapies include tisagenlecleucel (KYMRIAH™) and axicabtagene ciloleucel (YESCARTA™). Examples of monoclonal antibodies include rituximab and blinatumomab. Examples of cancer treatment vaccines include talimogene laherparepvec (T-VEC, or IMLYGIC®). Examples of immune system modulators include cytokines, such as interleukins (e.g., IL-2) and interferons (e.g., INF-alpha); hematopoietic growth factors, such as erythropoietin, IL-11, granulocyte-macrophage colony-stimulating factor, and granulocyte colony-stimulating factor; *Bacillus* Calmette-Guerin (BCG); and immunomodulatory agents, such as thalidomide, lenalidomide, pomalidomide, and imiquimod.

The chemotherapeutic agents and/or regimens can also be administered in combination with vitamin C, or a pharmaceutically acceptable salt thereof, and/or vitamin D, or a pharmaceutically acceptable salt thereof. Thus, in some embodiments, a method further comprises administering to subject vitamin C, or a pharmaceutically acceptable salt thereof, and/or vitamin D, or a pharmaceutically acceptable salt thereof (e.g., an effective amount of vitamin C, or a pharmaceutically acceptable salt thereof, and/or an effective amount of vitamin D, or a pharmaceutically acceptable salt thereof).

EXEMPLIFICATION

Example 1. Ketogenic Diet and Chemotherapy Combine to Disrupt Pancreatic Cancer Metabolism and Growth Summary Ketogenic diet is a potential means of augmenting cancer therapy. Here, ketone body metabolism and its interplay with classical chemotherapy is explored in pancreatic cancer. $^{13}$C-$^2$H isotope tracing studies revealed that the ketone body 3-hydroxybutyrate (3HB) is unidirectionally oxidized to make NADH, in contrast to carbohydrate derived lactate/pyruvate, which rapidly interconvert, buffering NADH/NAD. In murine pancreatic cancer (KPC tumors), ketogenic diet decreased glucose's concentration and TCA cycle contribution, enhanced 3HB's TCA contribution, and modestly elevated NADH, but did not impact tumor growth. In contrast, the combination of ketogenic diet and cytotoxic chemotherapy (gemcitabine, nab-paclitaxel, cisplatin) substantially raised tumor NADH and synergistically suppressed tumor growth, tripling the survival benefits of chemotherapy alone. Chemotherapy and ketogenic diet also synergized in immune-deficient mice, although long-term tumor control was only observed in mice with an intact immune system. Based on these data, a randomized clinical trial of chemotherapy with standard versus ketogenic diet was initiated for patients with metastatic pancreatic cancer (NCT04631445).

Introduction

Cells require chemical energy in the form of ATP to maintain their function. Metabolism generates ATP both anaerobically, through glycolysis, and aerobically, through the transfer of high-energy electrons first to NAD (which becomes NADH), then to the mitochondrial electron transport chain (ETC). The electron transport chain passes high-energy electrons to molecular oxygen to make water, coupled to the generation of the mitochondrial inner membrane proton gradient and, ultimately, ATP synthesis.

Cells have a finite respiratory capacity, determined by the number of healthy mitochondria and the availability of oxygen. In other words, there is a limit to how much NADH cells can handle. When this limit is approached, NADH and reduced respiratory chain complexes accumulate, leading to reactive oxygen species (ROS). This "reductive stress" can be catastrophic in patients with genetic mitochondrial disorders, and may also occur in cells where respiration is impaired for other reasons—for example, oxygen deprivation as often occurs in tumors.

Cells employ a variety of mechanisms to maintain a healthy NADH:NAD ratio. When respiratory capacity is low, cells generate ATP primarily through glycolysis, transferring the high energy electrons to pyruvate to make lactate. Such glycolytic metabolism requires an adequate supply of glucose, either from internal stores (glycogen) or the microenvironment, which is often glucose-depleted in tumors.

High NADH concentrations inhibit many of the enzymes that produce NADH in mitochondria, like pyruvate dehydrogenase, decreasing flux through the TCA cycle and thereby preventing further NADH accumulation. Cultured cells with impaired electron transport chain (ETC) function employ these strategies to survive but cannot proliferate in standard culture medium, in part because NADH buildup in mitochondria blocks the synthesis of aspartate. Growth can be restored by providing pyruvate, whose reduction to lactate clears extra NADH. Within the body, rapid exchange between circulating lactate/pyruvate and tissue NADH/NAD has been hypothesized to buffer local redox perturbations, and whole-body reductive stress can be mitigated by injection of an engineered enzyme LOXCAT that converts circulating lactate into pyruvate.

Pancreatic ductal adenocarcinoma (PDAC) tumors are characterized by stromal fibrosis that limits blood flow. They are hypoxic, nutrient-deprived, and have lower glucose and higher lactate levels than surrounding pancreatic tissue. Somehow, despite this harsh metabolic environment, PDAC tumors grow irrepressibly. Diagnosis typically occurs after metastasis with associated poor prognosis. Recently, augmentation of the most common chemotherapy regimen of gemcitabine and albumin-bound nanoparticle paclitaxel (nab-paclitaxel) with cisplatin led to median survival of 16 months, a step forward but still short. Accordingly, strategies to augment PDAC treatment are needed.

One possibility is dietary manipulation. Ketogenic diet—very low carbohydrate, low protein, and high fat—mimics several aspects of fasting without calorie restriction. Even in the fed state, glucose and insulin are low and ketone bodies (3HB, acetoacetate, and acetone) are high. Proposed mechanisms include suppression of pro-tumorigenic insulin signaling, depletion of glucose as a preferred tumor fuel, and antitumor effects of ketone bodies, which may potentially include reductive stress or histone deacetylation inhibition.

Although PI3 kinase (PI3K) inhibitors have not shown utility in pancreatic cancer, these inhibitors have been shown effective in pancreatic cancer mouse models when combined with ketogenic diet. In this context, the ketogenic diet prevents the PI3K inhibitor-induced hyperglycemia and associated hyperinsulinemia which otherwise tends to override the pharmacological PI3K inhibition, resulting in effective blockade of both PI3K signaling and tumor growth.

Here, it is shown that ketogenic diet, when combined with the current standard-of-care chemotherapy for PDAC, impairs tumor growth and significantly prolongs survival in murine pancreatic KPC tumors (LSL-Kras$^{G12D}$, p53$^{R172H}$, Pdx-Cre, spontaneous in pancreas or passaged as flank allograft). The tumor growth impairment is associated with glucose depletion, altered TCA substrate usage, and NADH elevation. It is further shown here that the combination of triple chemotherapy and a version of ketogenic diet high in saturated fat—a "butter diet"—suppresses tumor growth and enhances survival even more than the standard ketogenic diet.

Results

Redox buffering by lactate-pyruvate but not 3-hydroxybutyrate-acetoacetate. The metabolism of the classical ketone bodies, 3-hydroxybutyrate (3HB) and acetoacetate, were investigated in healthy animals. Like lactate and pyruvate, 3HB and acetoacetate chemically differ by one hydride: 3HB is a hydride donor, acetoacetate a hydride acceptor (FIG. 1A). The recognition that lactate is a major circulating fuel, with rapid exchange between pyruvate made via glycolysis into circulating lactate, gave rise to the idea that circulating lactate and pyruvate may collectively act as a "redox buffer"—that is, these metabolites flow back-and-forth between cells and the circulation, donating or accepting hydrides as needed such that local NADH:NAD ratios are maintained at healthy levels.

To confirm this idea, and to test whether the same might be true of circulating 3HB and acetoacetate, a set of isotope-tracer infusion experiments was devised. The circulatory turnover flux ($F_{circ}$) of a given metabolite refers to the rate at which tissues collectively take up the metabolite from arterial circulation; alternatively, $F_{circ}$ can be defined as the rate at which tissues collectively excrete the metabolite into the venous circulation, as these two rates are equal at steady state in minimally perturbative tracer infusions. Importantly, production and consumption that do not alter isotope labeling (for example, removal of an unlabeled hydride followed by addition of a different unlabeled hydride in its place) do not register as circulatory turnover flux. By comparing the $F_{circ}$s of $^{13}$C-labeled metabolites (for which oxidation and reduction reactions do not register as $F_{circ}$) and $^2$H-labeled metabolites (for which they do), the extent to which different circulating metabolites undergo rapid reversible redox reactions can be evaluated.

When uniformly $^{13}$C-labeled lactate was infused into fasted mice, the measured lactate turnover flux was 380 nmol/g/min, which is consistent with previous published measurements, and very fast (about 3 times faster than glucose $F_{circ}$ on a molar basis, or 1.5 times greater than glucose flux on a carbon atom basis). When $^2$H-labeled lactate (labeled only at the active hydride) was infused instead, the measured turnover flux increased to 550 nmol/g/min (FIGS. 1, 1F and 1G). This increase implied that lactate frequently enters tissues, delivers hydrides to NAD, and is then excreted as pyruvate or again reduced to lactate.

Figure 1C:
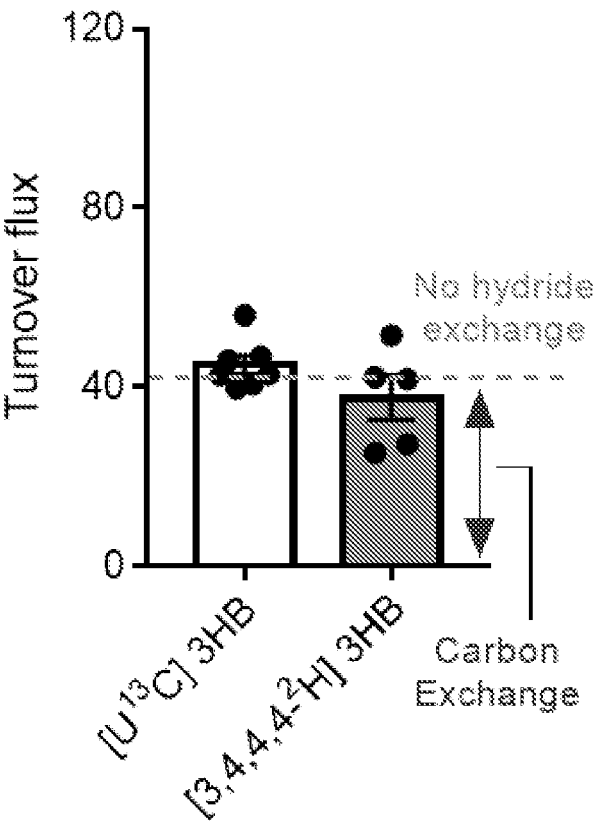
FIG. 1C shows circulatory turnover flux for $^2$H versus $^{13}$C-3HB. Equal turnover flux indicates unidirectional catabolism into acetoacetate. Mean±sem, n=5 for $^2$H, n=7 for $^{13}$C-3HB.
Figure 1D:
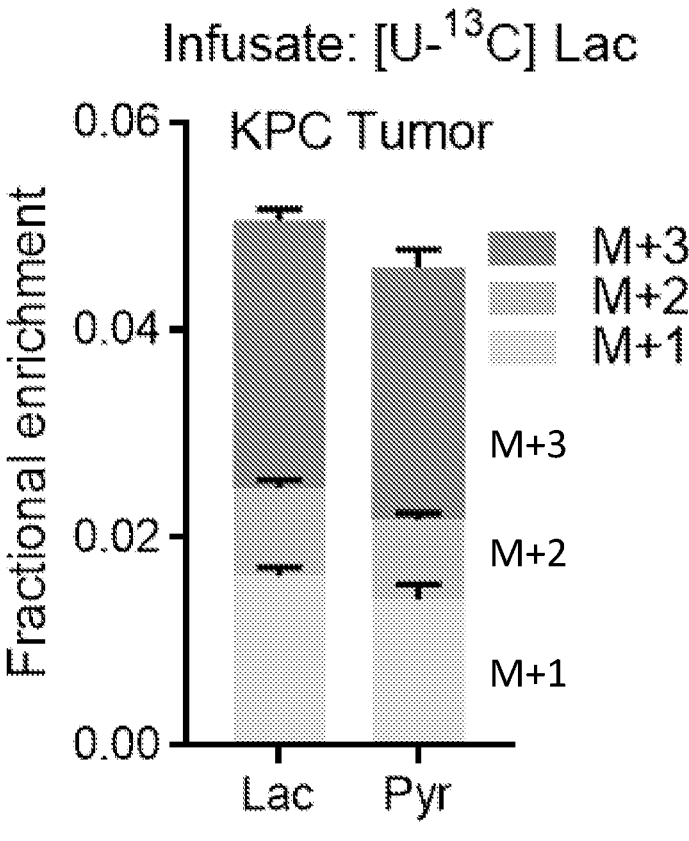
FIG. 1D shows mass isotope distribution of KPC allograft tumor lactate and pyruvate following [U-$^{13}$C]lactate infusion. Identical labeling patterns are consistent with rapid interconversion of these metabolites. Mean±sem, n=6.
Figure 1E:
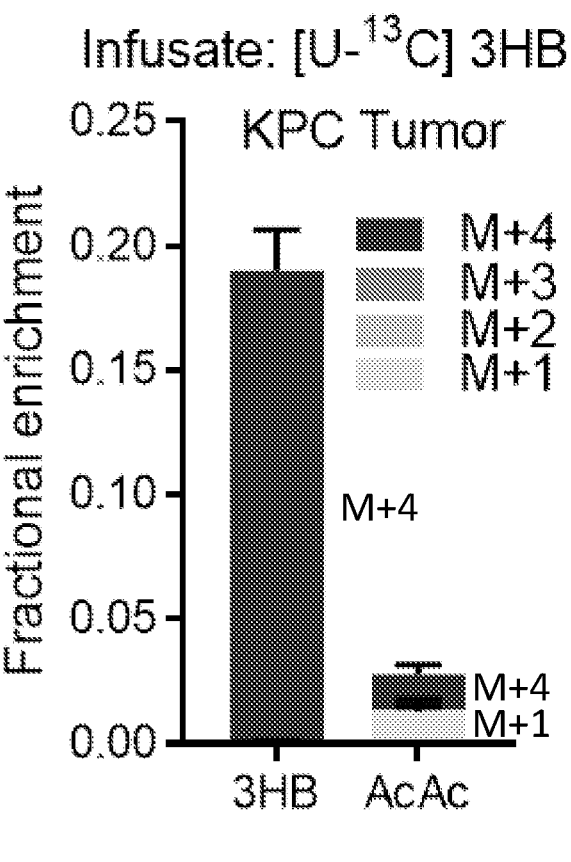
FIG. 1E shows mass isotope distribution of tumor 3HB and acetoacetate following [U-$^{13}$C]3HB infusion. Lack of acetoacetate labeling reflects its production from sources other than circulating 3HB. Mean±sem, n=6.
Figure 1F:
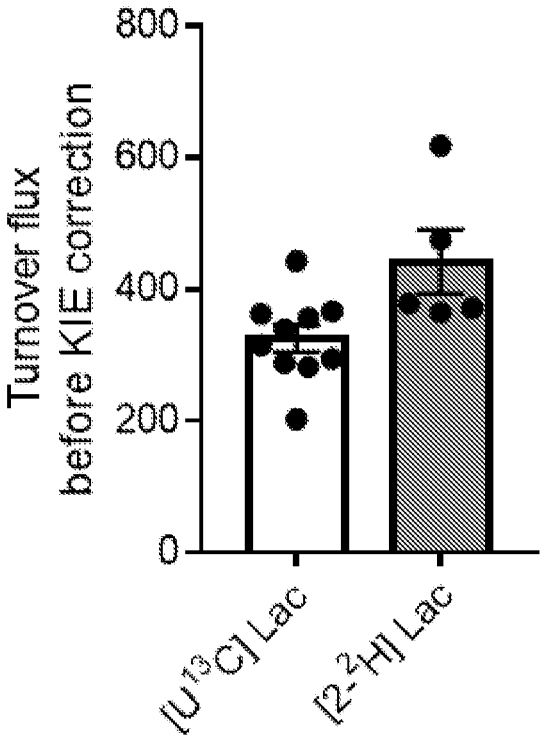
FIG. 1F shows circulatory turnover flux (units of nmole/min/gram body weight) of [2-$^2$H] and [U-$^{13}$C]lactate prior to kinetic isotope effect correction. Mean±sem, n=5 for $^2$H, n=10 for $^{13}$C lactate.
Figure 1G:
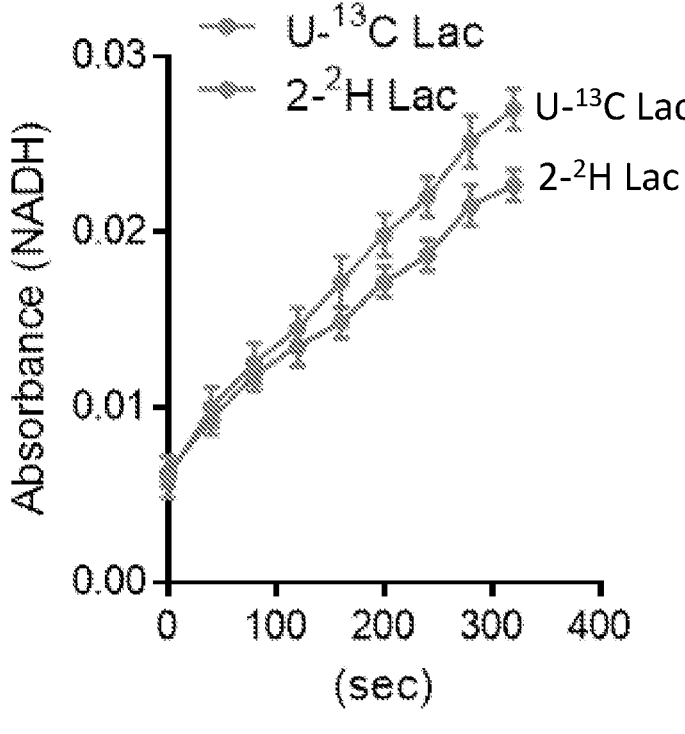
FIG. 1G shows absorbance of NADH generated by lactate dehydrogenase following addition of [U-$^{13}$C]lactate or [2-$^2$H]lactate.
Figure 1H:
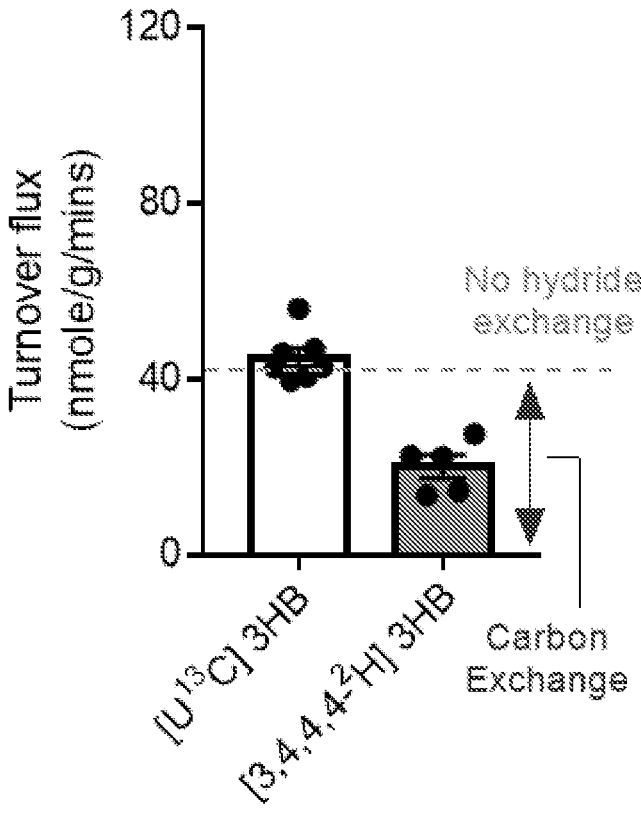
FIG. 1H shows circulatory turnover flux (units of nmole/min/gram body weight) of [3,4,4,4-$^2$H] and [U-$^{13}$C]3HB prior to kinetic isotope effect correction. Mean±sem, n=5 for $^2$H, n=7 for $^{13}$C 3HB.
Figure 1I:
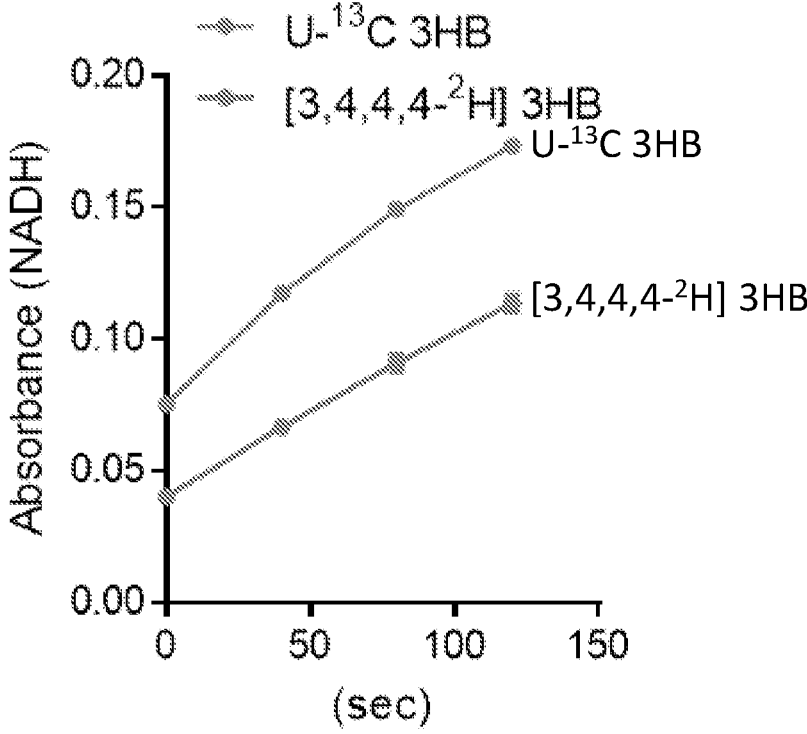
FIG. 1I shows absorbance of NADH generated by 3-hydroxybutyrate dehydrogenase following addition of [U-$^{13}$C]3HB or [3,4,4,4-$^2$H]3HB.
Figure 1J:
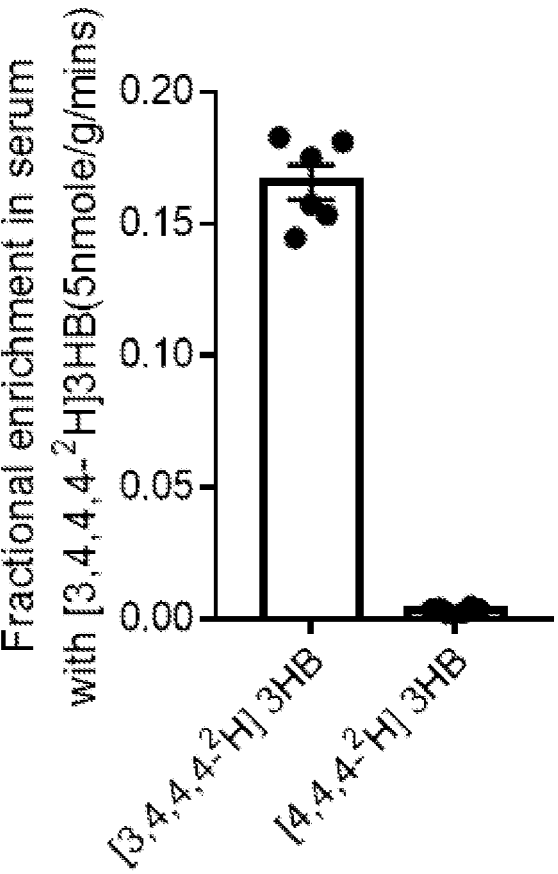
FIG. 1J shows fraction of M+3 and M+4 $^2$H-3HB in serum following [3,4,4,4-$^2$H]3HB infusion (5 nmole/min/g). Mean±sem, n=6.

In contrast, the 3HB turnover flux as measured with uniformly $^{13}$C-labeled 3HB versus $^2$H-labeled 3HB was indistinguishable (~40 nmol/g/min) (FIGS. 1C, 1H and 1I). Further, from infused [3,4,4,4-$^2$H]3HB (M+4), the product arising from oxidation to acetoacetate followed by re-reduction to 3HB ([4,4,4-$^2$H]3HB, M+3) was not observed (FIG. 1J). Thus, unlike lactate-pyruvate, the 3HB-acetoacetate pair does not participate in reversible cellular redox reactions, and instead is unidirectionally catabolized. Accordingly, while lactate-pyruvate acts as a redox buffer, 3HB is a unidirectional hydride donor.

To provide further evidence that 3HB-acetoacetate exchange is minimal in pancreatic tumors, [U-$^{13}$C]lactate and [U-$^{13}$C]3HB were infused, separately, into mice fed regular carbohydrate-rich diet, bearing KPC flank allograft tumors. After infusions reached steady state, tumors were extracted and metabolites analyzed by LC-MS. With $^{13}$C-lactate infusion, the tumor pyruvate and lactate isotope labeling patterns were indistinguishable, consistent with their rapid interconversion (FIG. 1D). In contrast, when $^{13}$C-3HB was infused, acetoacetate labeling remained minimal (7 times lower than 3HB), indicating that, on the control diet, tumor acetoacetate neither comes from nor exchanges with 3HB (FIG. 1E).

Figure 1K:
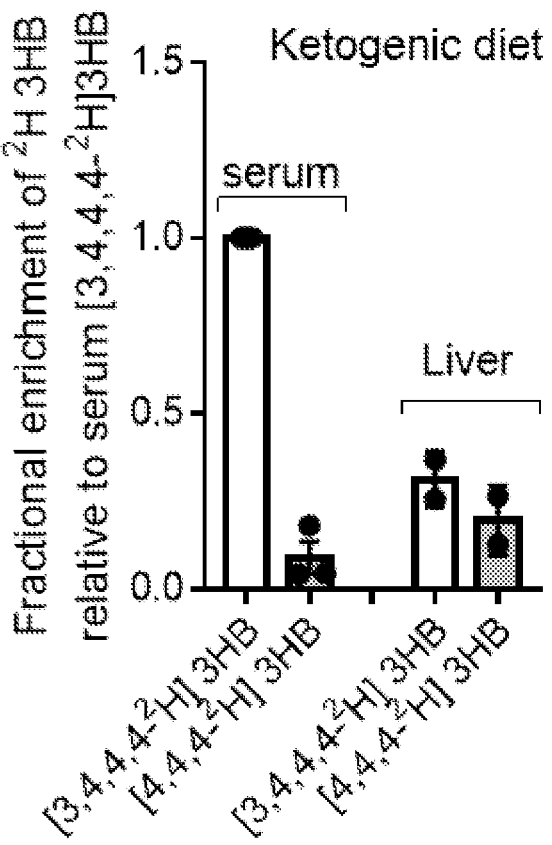
FIG. 1K shows fraction of M+3 and M+4 $^2$H-3HB in serum and liver following [3,4,4,4-$^2$H]3HB infusion into mice on ketogenic diet. Mean±sem, n≥2.

Ketogenic diet is a physiological means of dramatically increasing circulating 3HB and acetoacetate. To check whether ketogenic diet induces hydride exchange between these ketone bodies, [3,4,4,4-$^2$H]3HB was infused to mice (without tumors) fed ketogenic diet. In the ketogenic organ of liver, substantial [4,4,4-$^2$H]3HB (M+3) was observed, indicating that 3HB and acetoacetate exchange locally in liver. But, circulating [4,4,4-$^2$H]3HB was minimal, implying minimal reversible flux between the ketone bodies at the whole-body level (FIG. 1K). Thus, irrespective of dietary status, 3HB acts largely as a unidirectional hydride donor rather than a reversible redox exchanger like lactate.

Figure 2A:
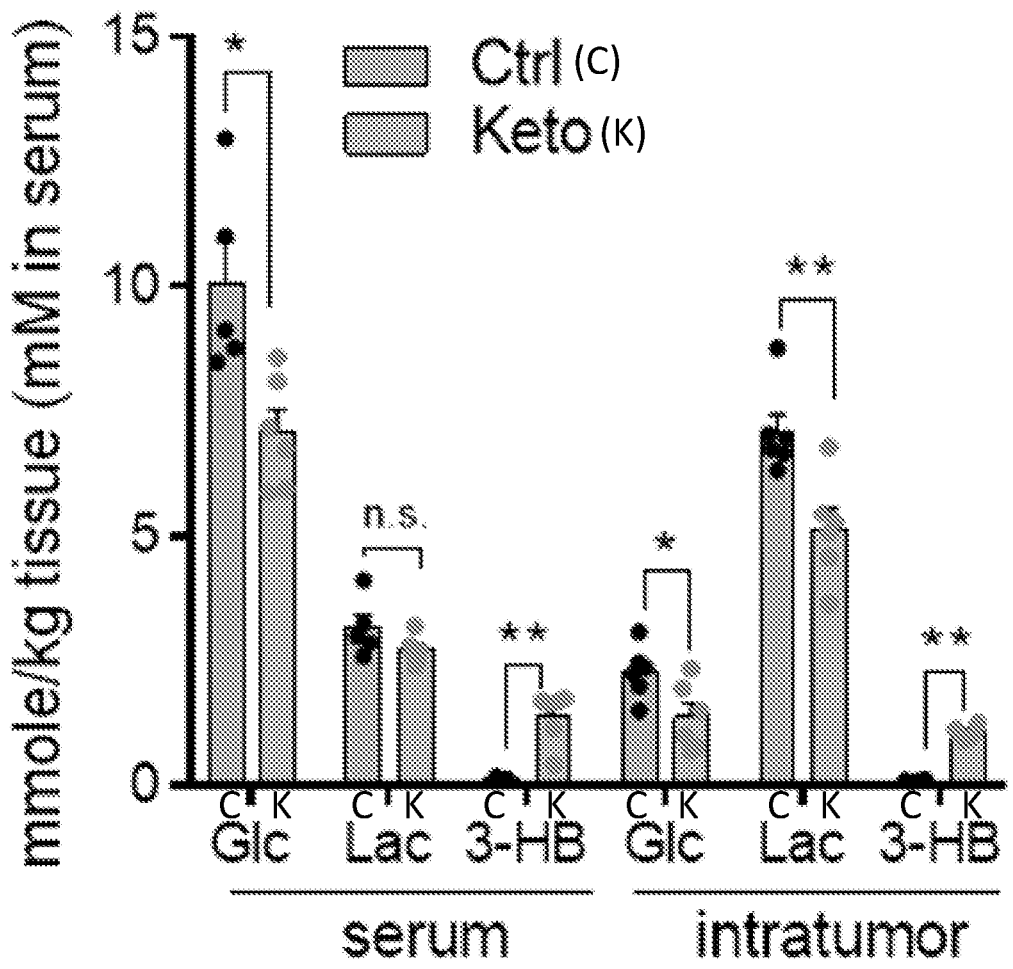
FIG. 2A shows metabolite concentrations in KPC tumors. Mean±sem, n≥5.
Figure 2B:
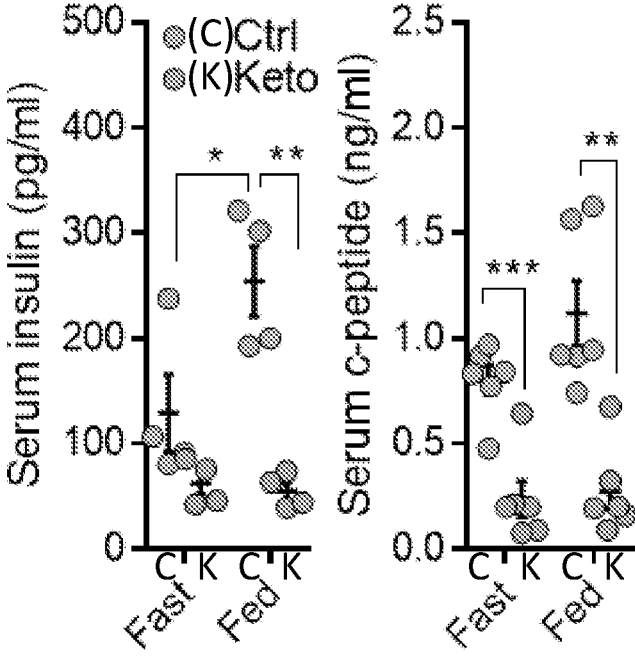
FIG. 2B shows serum insulin, c-peptide in KPC tumors. Mean±sem, n=4 for insulin, n=6 for c-peptide.
Figure 2C:
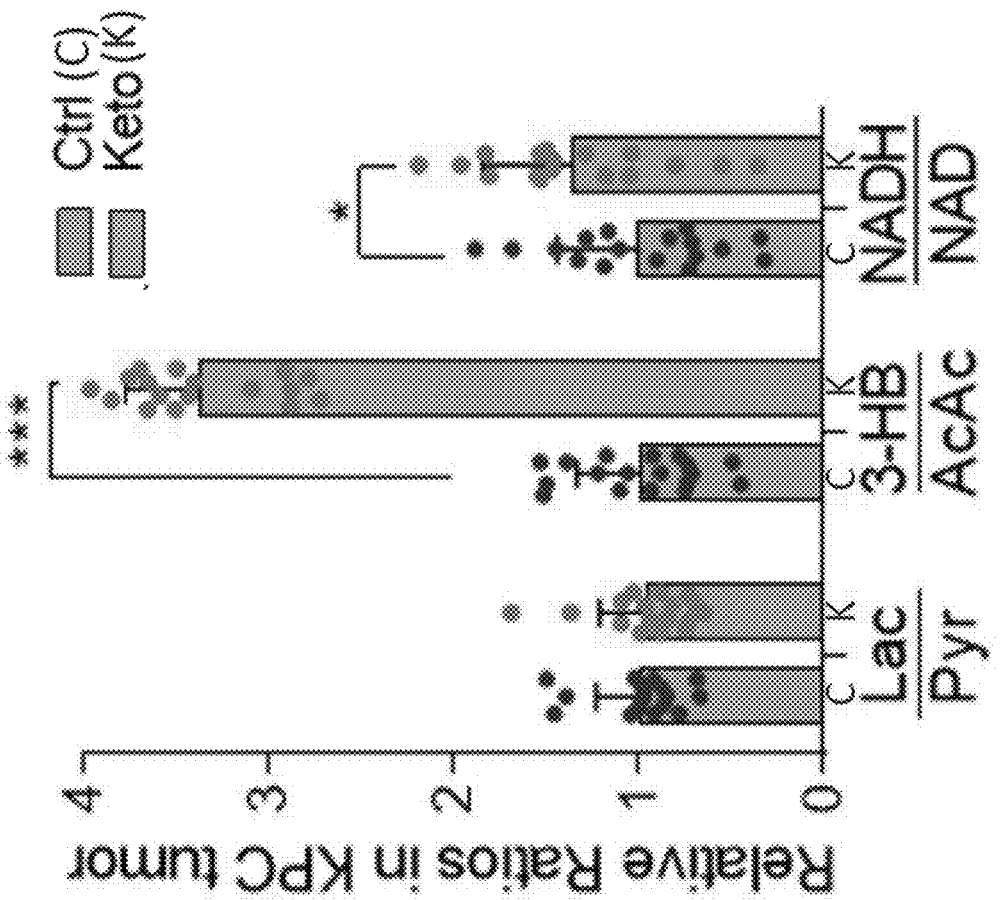
FIG. 2C shows intratumor redox pairs in KPC tumors. Mean±sem, n=17.
Figure 2D:
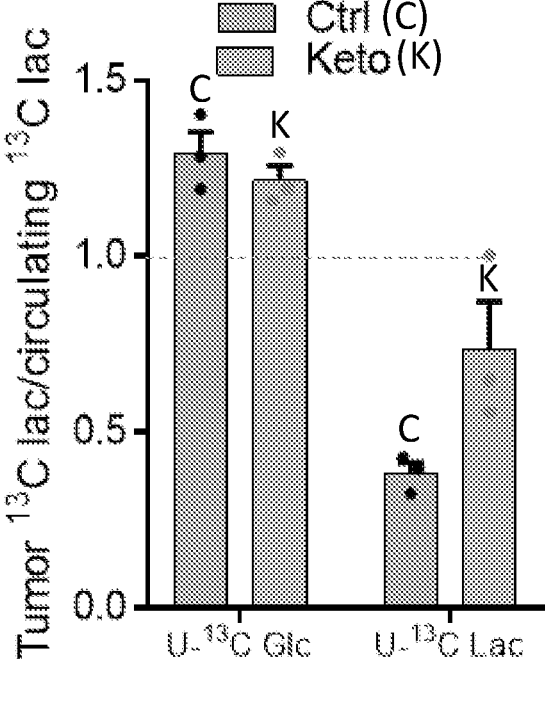
FIG. 2D shows tumor versus circulating lactate labeling from [U-$^{13}$C]glucose and [U-$^{13}$C]lactate infusion. In ketogenic diet, tumor lactate comes more from circulating lactate, as opposed to intratumoral glycolysis. Mean±sem, n=3.
Figure 2E:
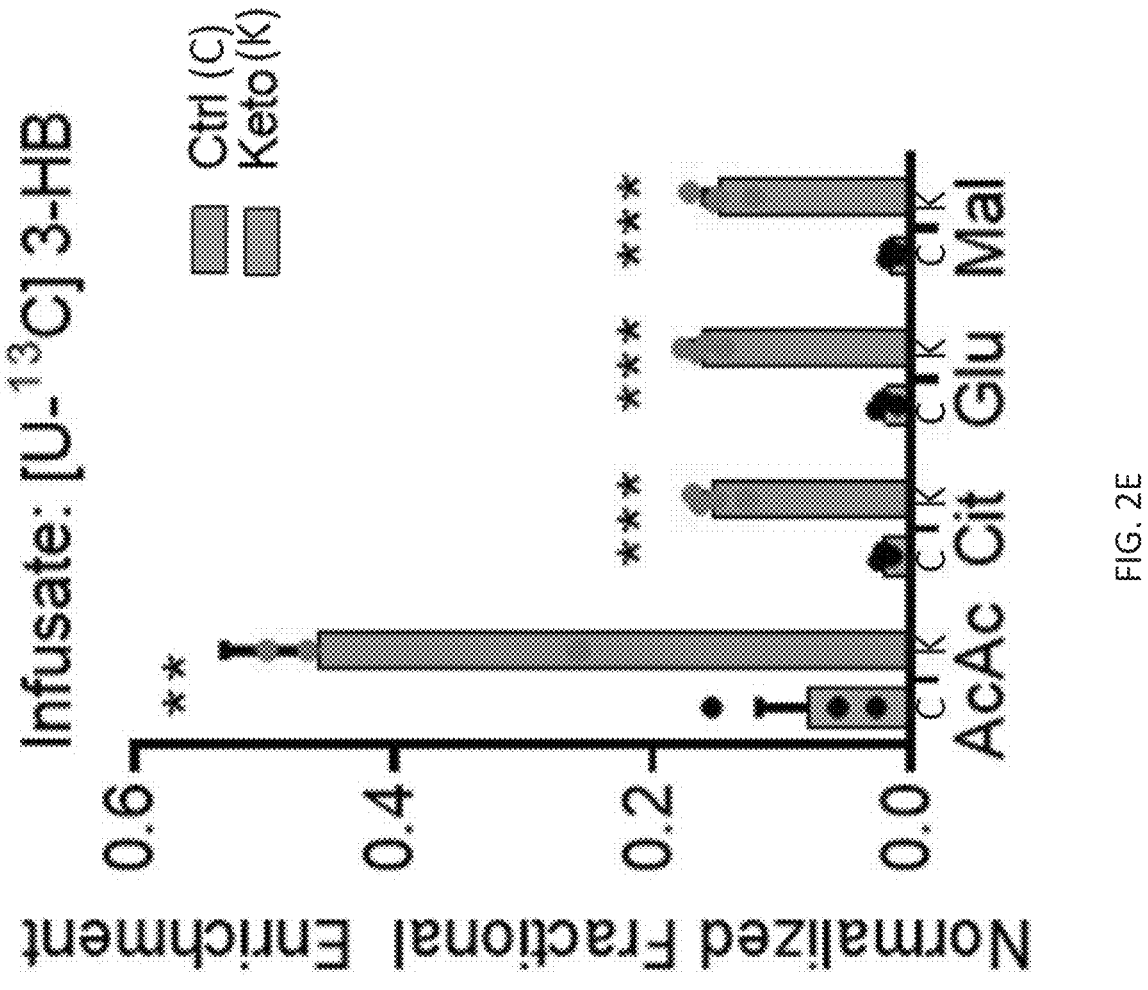
FIG. 2E shows tumor metabolite labeling from [U-$^{13}$C] 3HB. Mean±sem, n=3 for control diet, n=4 for ketogenic diet.
Figure 2F:
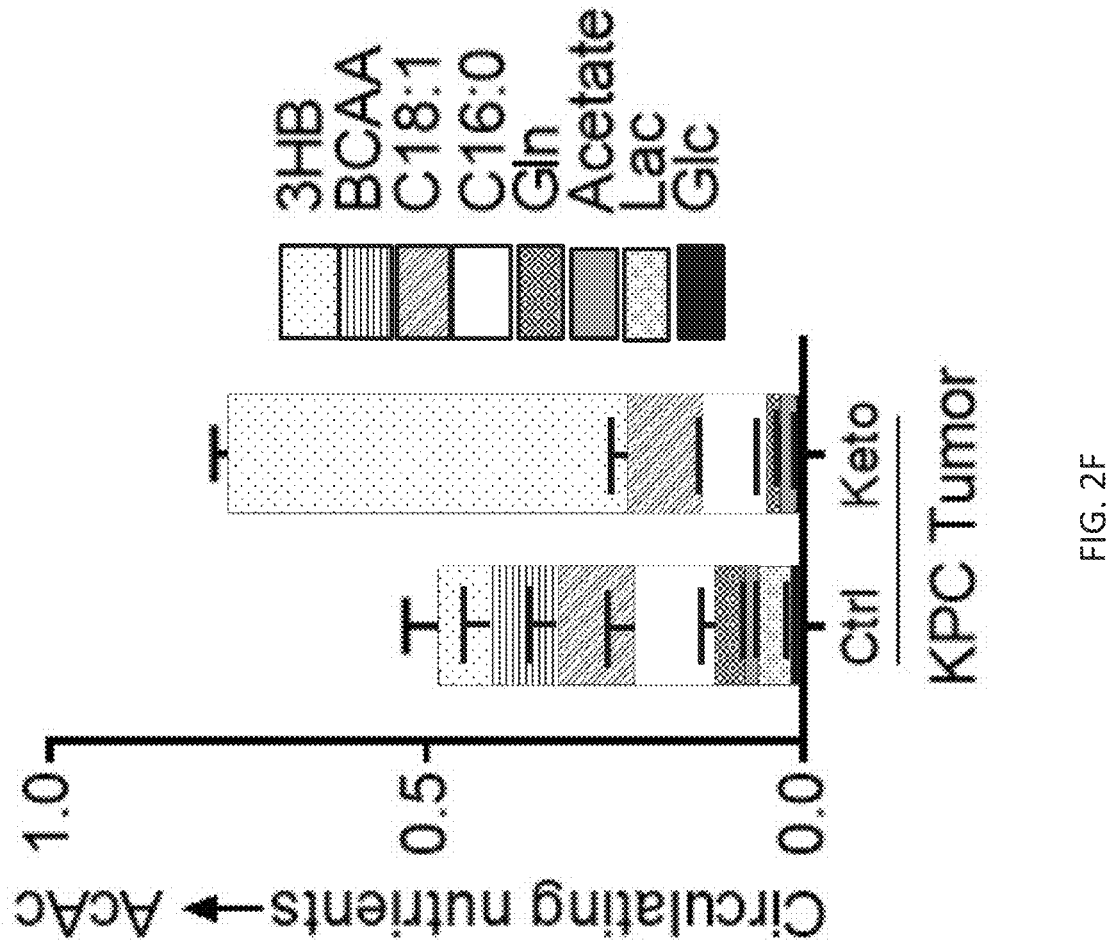
FIG. 2F shows direct contributions of circulating nutrients to tumor acetoacetate. Mean±SD.
Figure 2G:
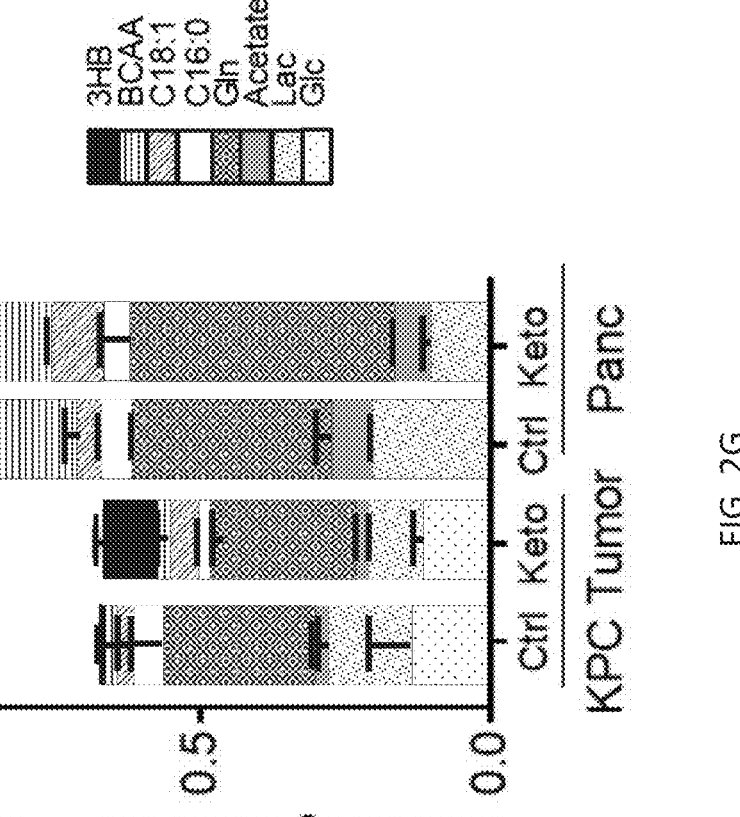
FIG. 2G shows Direct contributions of circulating nutrients to tumor TCA cycle (malate as representative metabolite). Mean±SD.
Figure 2H:
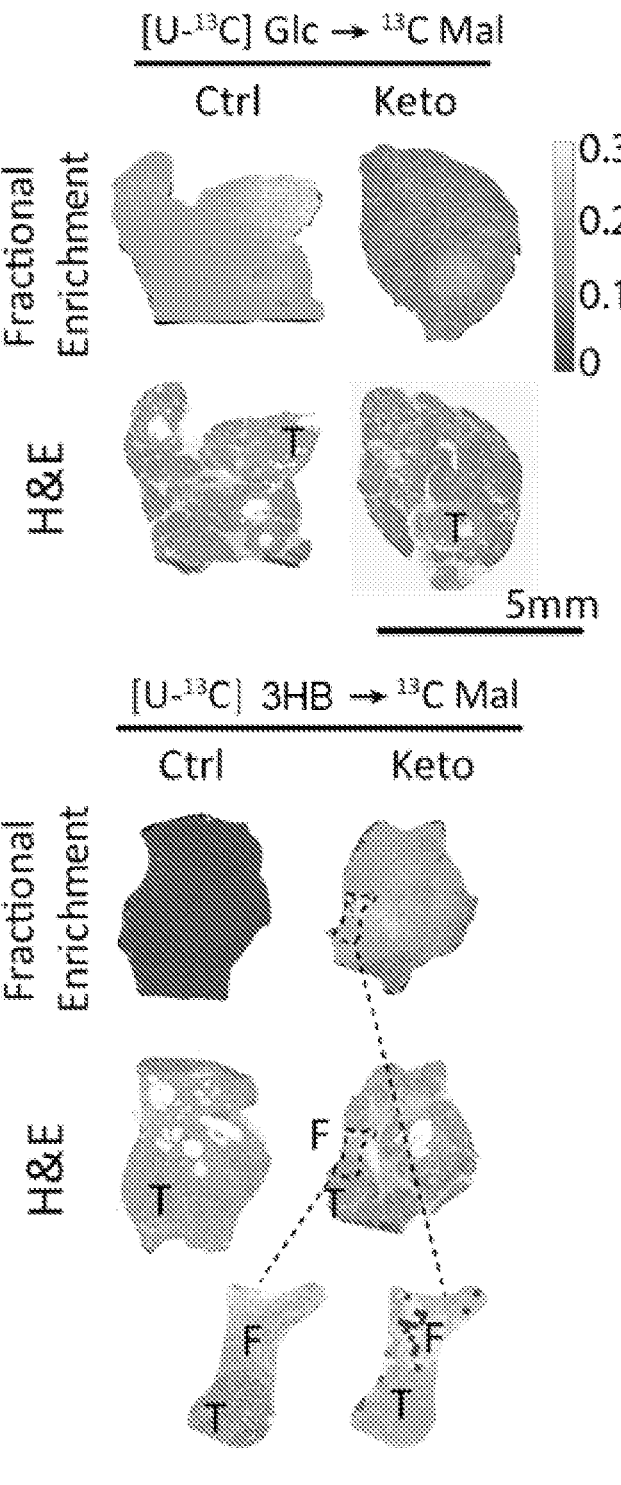
FIG. 2H shows MALDI-imaging mass spectrometry of malate labeling from $^{13}$C-glucose (top) and $^{13}$C-3HB (bottom) in pancreas from KPC mice. T, tumor; F, peritumoral fibrosis.
Figures 2I, 2J:
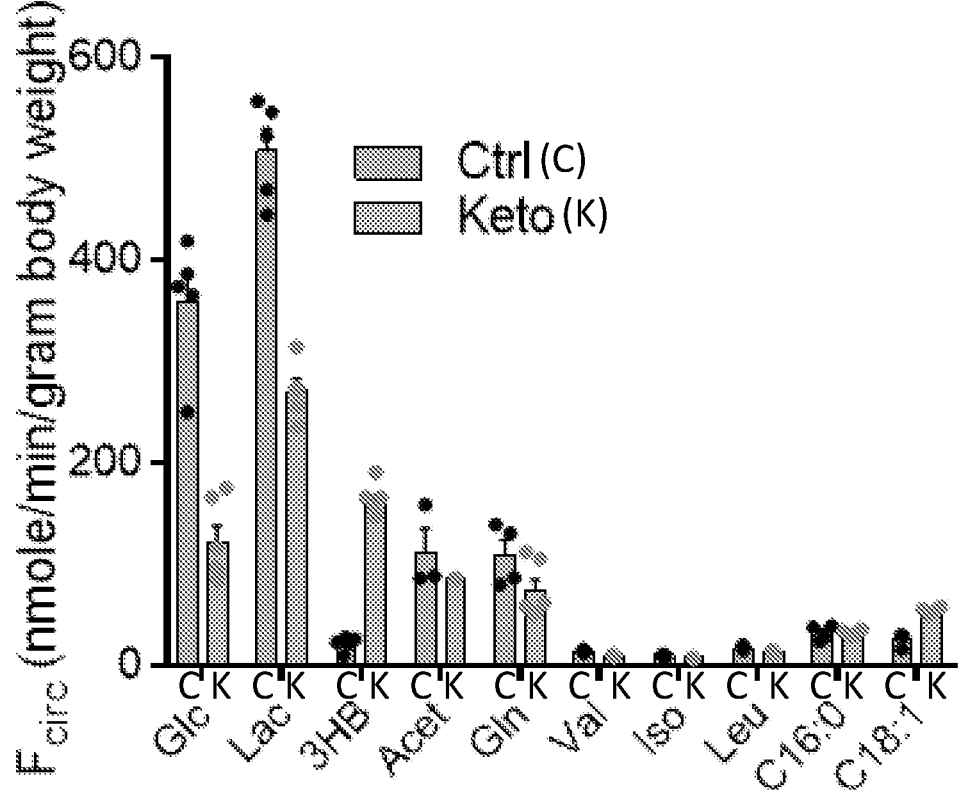
FIG. 2I shows nutrient composition of standard lab chow (Pico 5053) and ketogenic diet chow (Bio-serv, S3666).
FIG. 2J shows circulatory turnover fluxes of major nutrients based on [U-$^{13}$C] infusions. Mean±sem, n≥3.
Figure 2K:
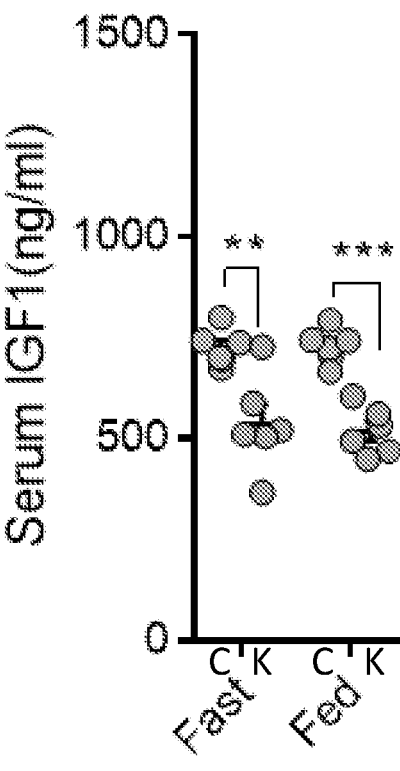
FIG. 2K shows serum IGF1. Mean±sem, n=6.

Ketogenic diet suppresses tumor glucose utilization and induces 3-hydroxybutyrate burning. To explore the metabolic effects of ketogenic diet in mice bearing tumors, after KPC allograft implantation, once tumors became palpable (roughly one week), mice were fasted overnight and then they were either maintained on a control diet or switched to a ketogenic diet. Ketogenic diet suppressed circulating glucose concentration, glucose and lactate $F_{circ}$, and glucose and lactate intratumoral concentrations (FIGS. 2A, 2I, 2J). Intratumoral glucose fell to 1.3 mM, sufficiently low to potentially impair tumor glycolysis (FIGS. 2A, 2I, 2J). Circulating insulin, c-peptide, and IGF1 were also suppressed, while 3HB levels and $F_{circ}$ were dramatically increased (FIGS. 2A, 2B, 2J, 2K).

How the ratios of metabolic redox pairs (metabolites which differ by a hydride) changed on the ketogenic diet was also monitored. While the intratumoral lactate:pyruvate ratio remained roughly the same in mice on the ketogenic diet, the 3HB:acetoacetate ratio increased more than three-fold, and the NADH:NAD ratio increased by ~40% (FIG. 2C).

Figure 2L:
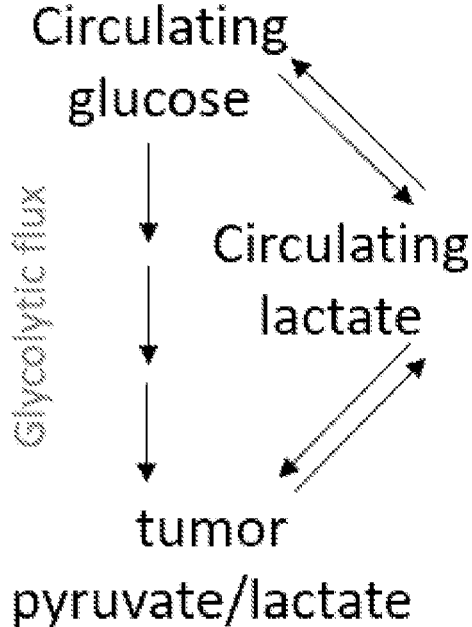
FIG. 2L is an illustration of tumor pyruvate/lactate sources.
Figure 2M:
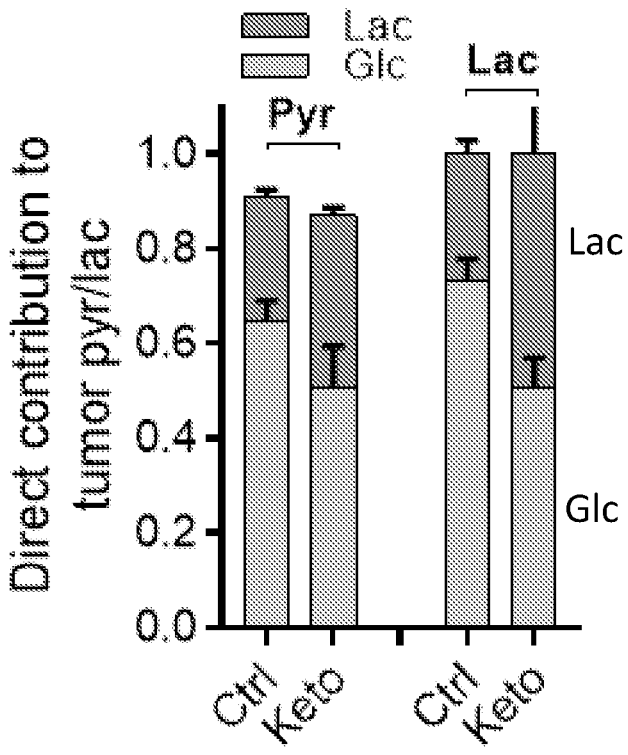
FIG. 2M shows direct contributions of circulating glucose and lactate to intratumoral pyruvate/lactate. Ketogenic diet suppresses the direct glucose contribution. Mean±SD, n=3.

To probe tumor glycolysis, [U-$^{13}$C]glucose was infused, and tumors were harvested at labeling pseudo-steady state (2.5 h). Tumor lactate was labeled by glucose, to a yet greater extent than was circulating lactate, indicating active tumor glycolysis at a rate sufficient to outpace lactate exchange with the circulation and drive tumor lactate accumulation. Faster glycolysis than lactate exchange is further proven by [U-$^{13}$C]lactate infusion, where more than 60% of intratumor lactate pool is diluted by other sources like glycolysis (FIGS. 2D, 2L, 2M). In addition to lowering intratumoral lactate, consistent with its suppressing tumor glycolysis, ketogenic diet decreased tumor lactate and pyruvate enrichment from infused glucose, correspondingly increasing the contribution from circulating lactate (FIGS. 2D, 2L, 2M).

To track the fate of circulating 3HB in tumors, [U-$^{13}$C]3HB was infused. Ketogenic diet dramatically enhanced the fraction of tumor acetoacetate labeled from circulating 3HB, indicating induction of intratumoral 3HB catabolism. Moreover, 3HB extensively labeled TCA intermediates and glutamate (which rapidly exchanges with α-ketoglutarate), selectively in mice on the ketogenic diet (FIG. 2E).

Figure 2N:
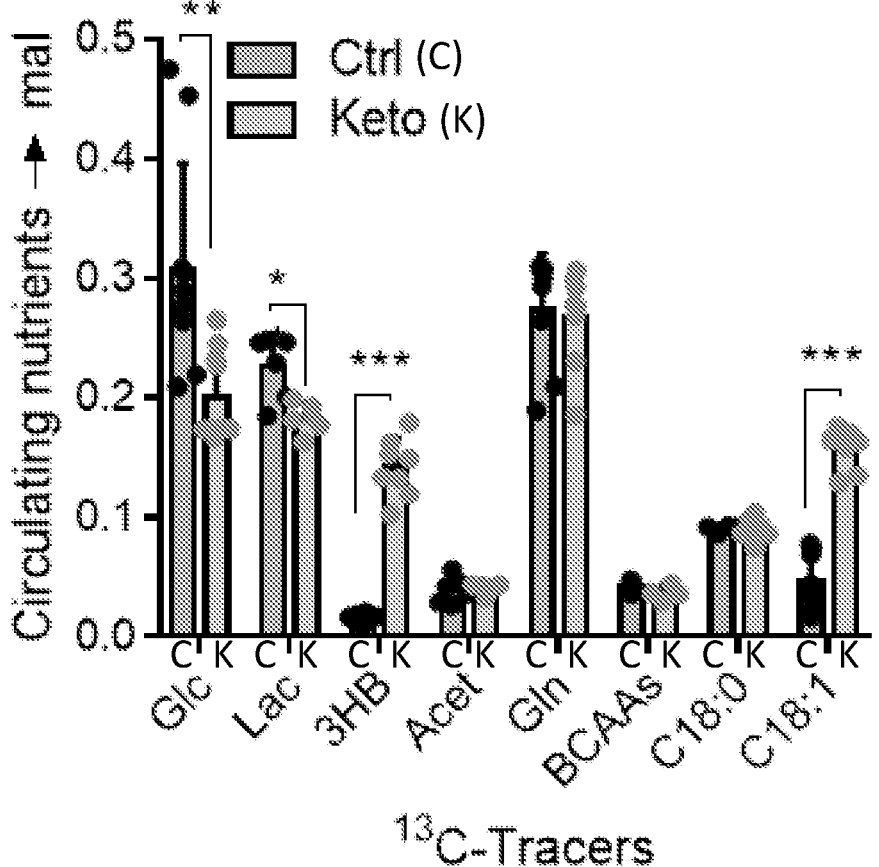
FIG. 2N shows normalized carbon labeling to tumor TCA cycle (malate as representative metabolite) from different [U-$^{13}$C]tracers. Mean±sem, n=3. p<0.01, *p<0.001 by two-tailed Student's t test.

To understand more comprehensively which nutrients are oxidized in pancreatic tumors, on both control and ketogenic diet, a series of $^{13}$C-tracer infusion experiments was performed in tumor-bearing mice with $^{13}$C-labeled glucose, lactate, oleate (C18:1, the most abundant monounsaturated fatty acid), palmitate (C16:0, the abundant saturated fatty acid), acetate, glutamine, and a mixture of branched chain amino acids. On control diet, tumor acetoacetate came more from fat and amino acids than 3HB. In contrast, on ketogenic diet, 3HB was the dominant tumor acetoacetate source (FIG. 2F). In TCA cycle intermediates, in both dietary conditions, glutamine was the largest tumor TCA carbon contributor. Both glucose and lactate contributed directly to the tumor TCA cycle and these contributions fell in ketogenic diet, being replaced by increased contributions from oleate and 3HB (FIGS. 2G, 2N). The 3HB contribution to the tumor TCA far exceeded that in normal pancreas (FIG. 2G).

Figure 2O:
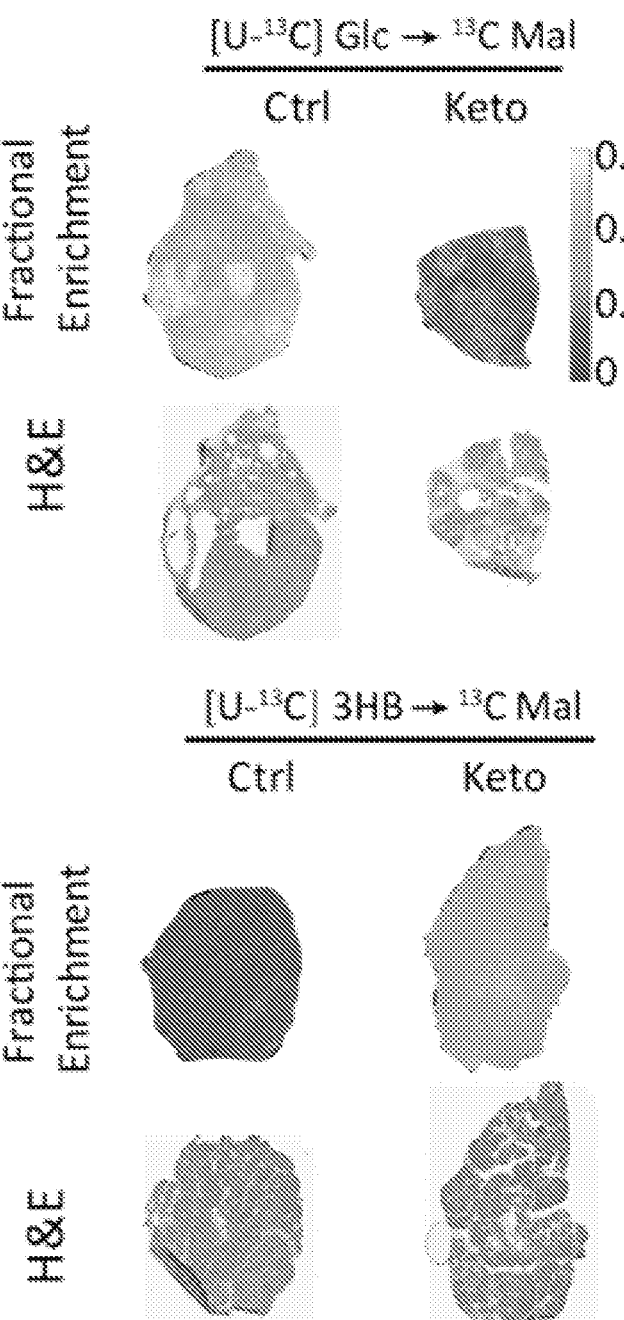
FIG. 2O shows MALDI-imaging mass spectrometry of malate labeling from [U-$^{13}$C]glucose (top) and [U-$^{13}$C]3HB (bottom) in pancreas from KPC mice. T, tumor.

Heterogeneity in tumor nutrient use probed by imaging mass spectrometry. To explore tumor heterogeneity with respect to nutrient oxidation, U-$^{13}$C glucose or 3HB was infused to KPC mice with spontaneous pancreatic tumors and the spatial distribution of downstream TCA cycle labeling was analyzed using MALDI-imaging mass spectrometry. Higher glucose contribution to the TCA cycle of tumors compared to the surrounding pancreas was observed, with greatest contribution in epithelial cancer cell rich regions. In ketogenic diet, although PDAC tumor continued to show greater glucose contribution to TCA relative to surrounding pancreas, the overall glucose TCA contribution was dramatically suppressed (FIGS. 2H, 2O).

Analogous MALDI-imaging tracing studies with 3HB confirmed minimal 3HB contribution to normal or tumor pancreatic TCA cycle in the standard diet condition. In mice fed ketogenic diet, however, tumors oxidized 3HB as a source of high energy electrons, with particularly intense TCA isotope labeling observed in the regions of peritumoral fibrosis (FIGS. 2H, 2O). Thus, ketogenic diet suppressed tumor glucose oxidation and induced tumor 3HB burning.

Figure 3A:
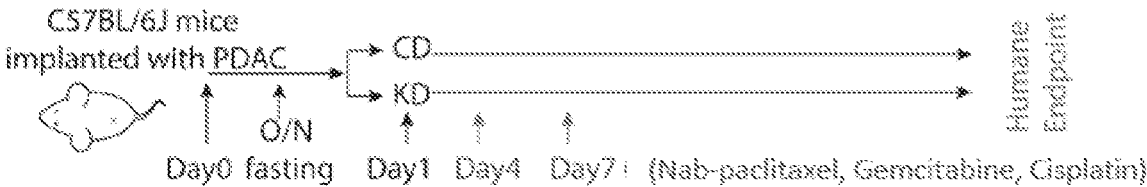
FIG. 3A shows chemotherapy regimen (triple chemotherapy: nab-paclitaxel, gemcitabine, cisplatin) with doses administered on day 4 and day 7 after diet switch in C57BL/6 mice with KPC allografts.
Figure 3B:
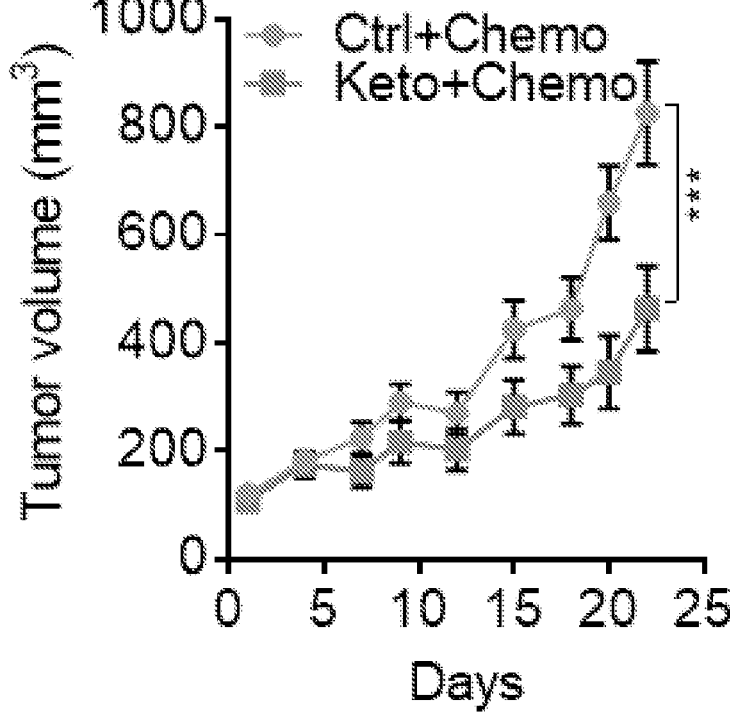
FIG. 3B shows allograft tumor volumes (batch #2, mean±sem, n=11 mice per group; for other batches, see FIG. 3K).
Figure 3C:
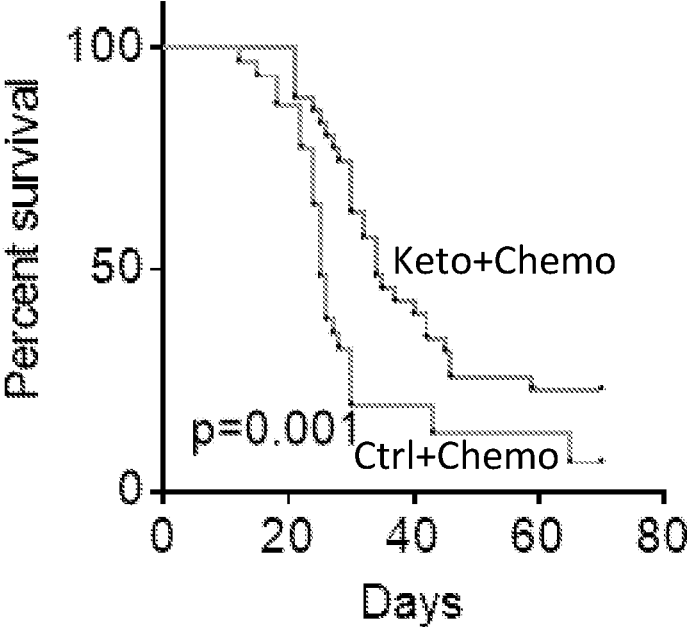
FIG. 3C shows a Kaplan-Meier curve (n=31 mice for Ctrl+Chemo and n=35 mice for Keto+Chemo).

Ketogenic diet synergizes with cytotoxic chemotherapy. Motivated by the ketogenic diet-induced changes in tumor nutrient use, downstream effects were looked for. No impact was observed on nucleotides, energy charge, tumor growth rate, or animal survival (FIGS. 3I-3K).

Given the lack of direct antitumor activity of the ketogenic diet, its impact in combination with cytotoxic chemotherapy (gemcitabine, nab-paclitaxel, cisplatin) was tested. Mice with palpable KPC allograft tumors were treated with the triple chemotherapy 4 and 7 days after switching permanently to ketogenic diet (compared to remaining on control diet) (FIG. 3A). This experiment was repeated four times, for a total of 66 mice randomized to either ketogenic or control diet over the course of two years. The combination of ketogenic diet and chemotherapy synergistically suppressed tumor growth and prolonged survival. The benefits were evident in each individual experiment (FIGS. 3L and 3M). Overall, the average survival gain due to chemotherapy alone was 5.8 days, and this increased to 16 days for mice on the ketogenic diet (FIGS. 3C and 3K).

Figure 3D:
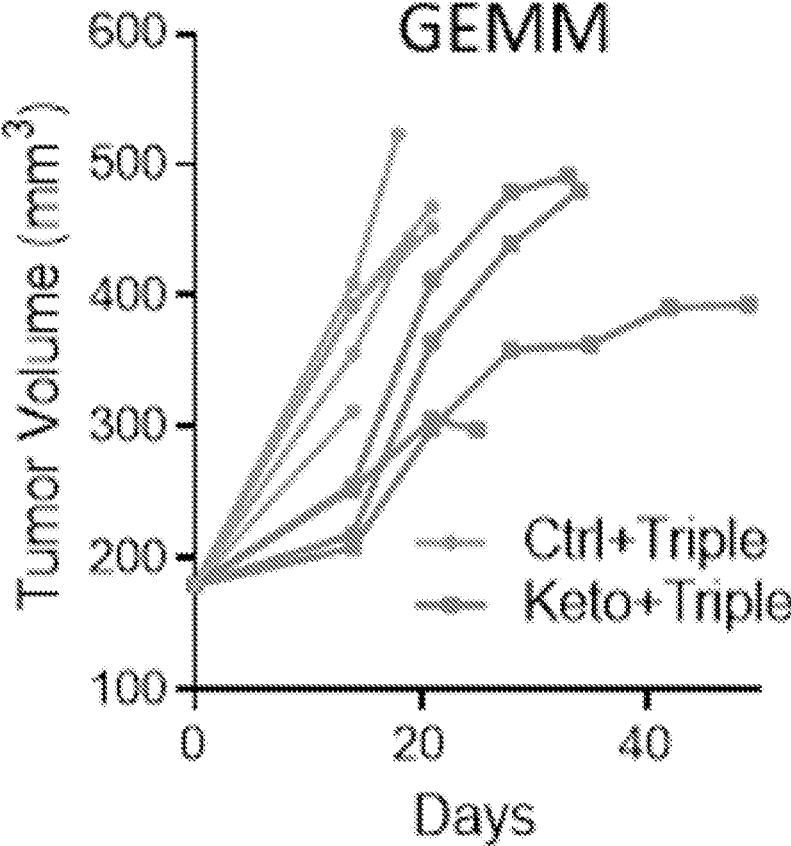
FIG. 3D shows primary tumor volumes in KPC genetically engineered mouse model (GEMM) (each line represents one mouse).
Figure 3E:
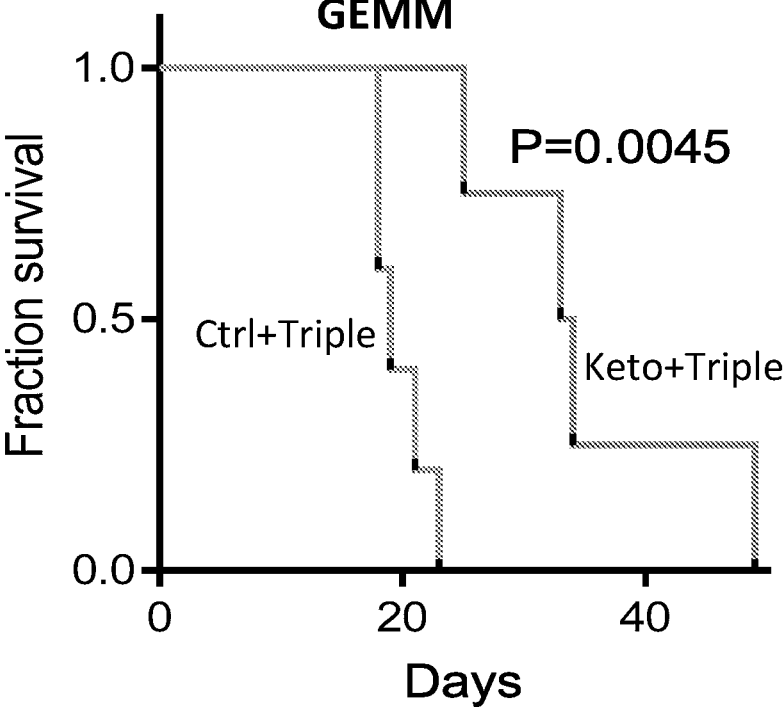
FIG. 3E shows a Kaplan-Meier curve (n=5 for Ctrl+Chemo group, n=4 for Keto+Chemo group).
Figure 3F:
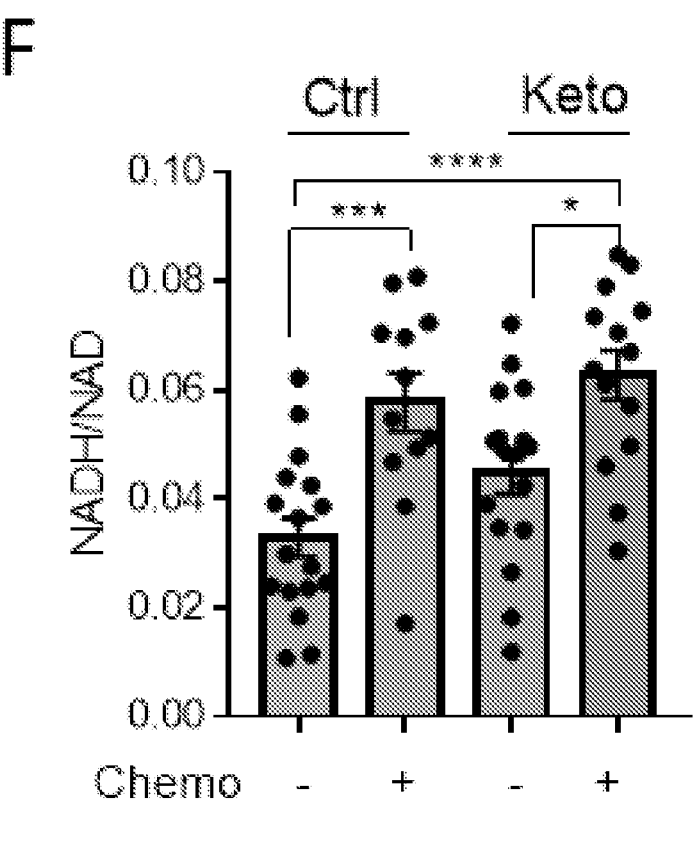
FIG. 3F shows NADH/NAD ratio in KPC allograft tumors (n=17 for Ctrl group, n=12 for Keto group, n=17 for Ctrl+Chemo group, n=14 for Keto+Chemo group).
Figure 3G:
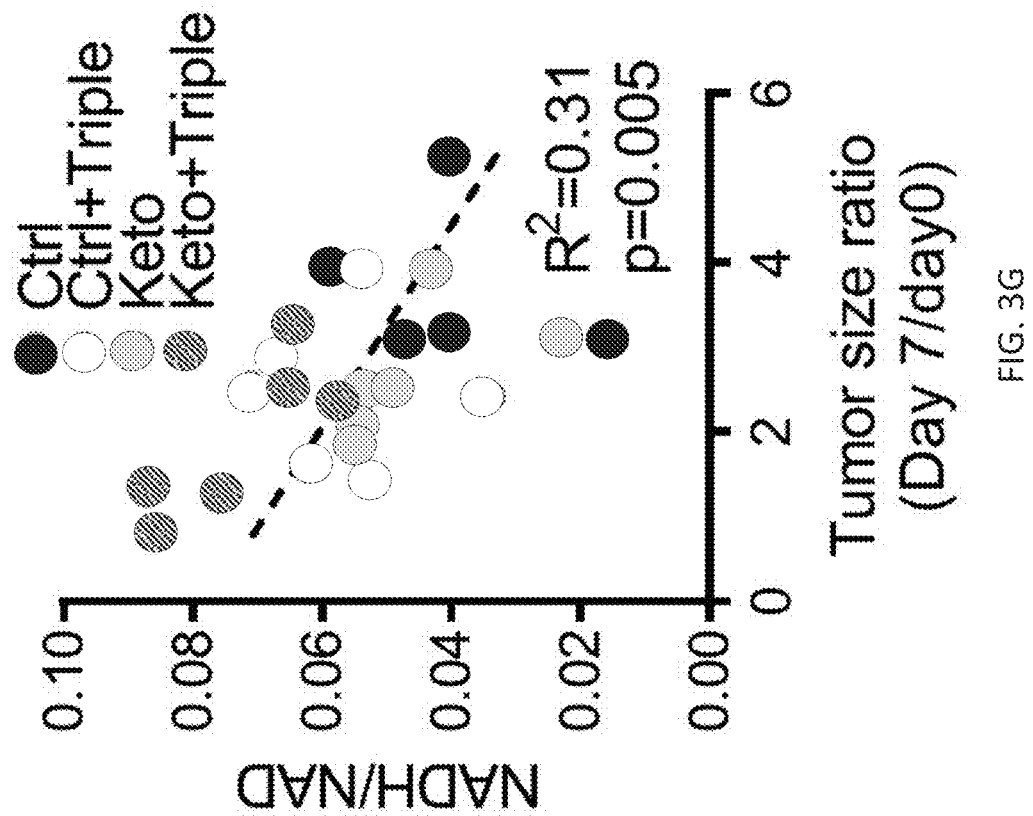
FIG. 3G shows correlation of intratumor NADH/NAD ratio with tumor growth suppression. Mice were sacrificed on Day 7 and NADH/NAD measured, and plotted versus tumor growth (or, for values <1, regression) over the preceding 7 days.
Figure 3H:
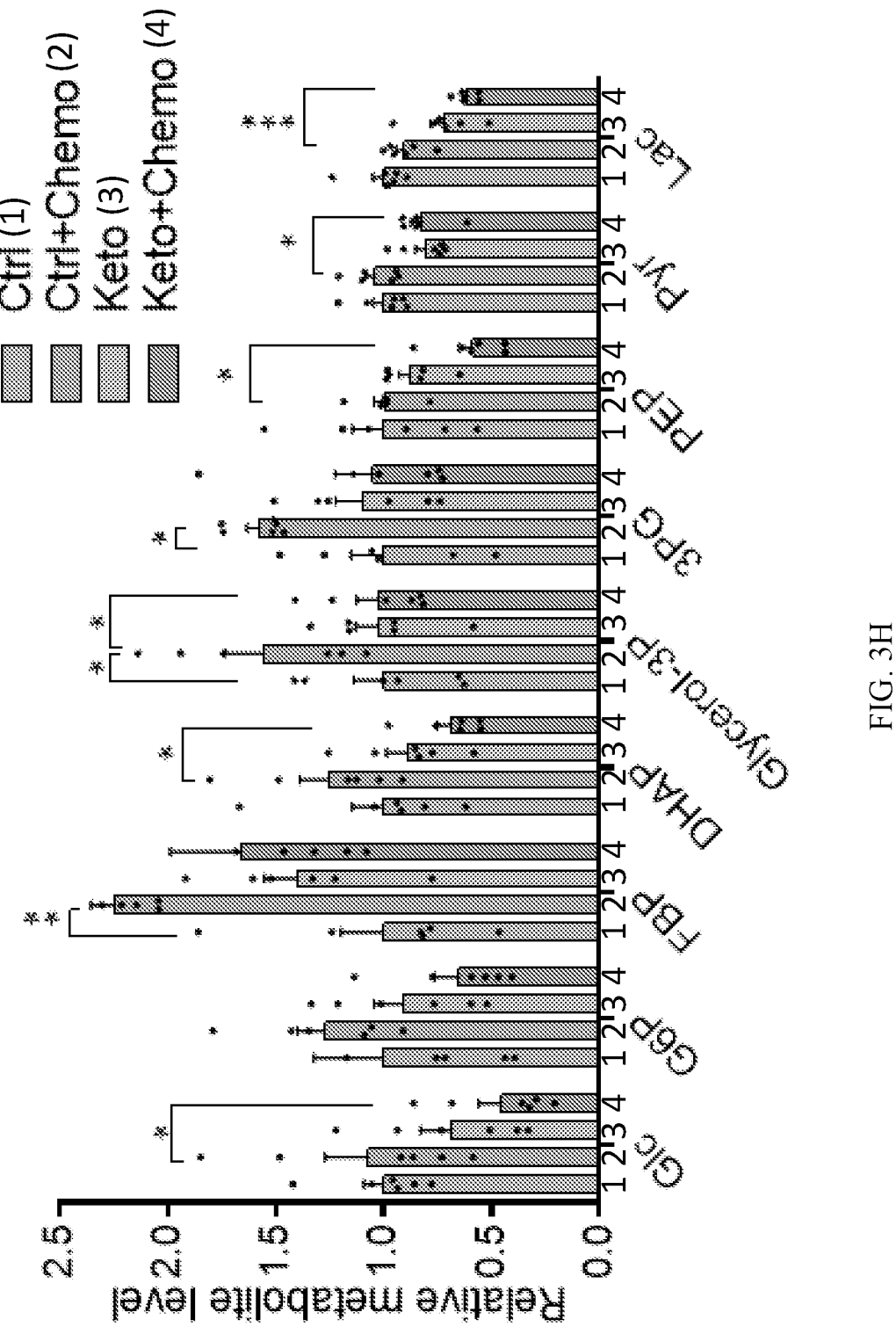
FIG. 3H shows intratumoral glycolytic metabolite levels (n≥4 mice per condition).
Figure 3I:
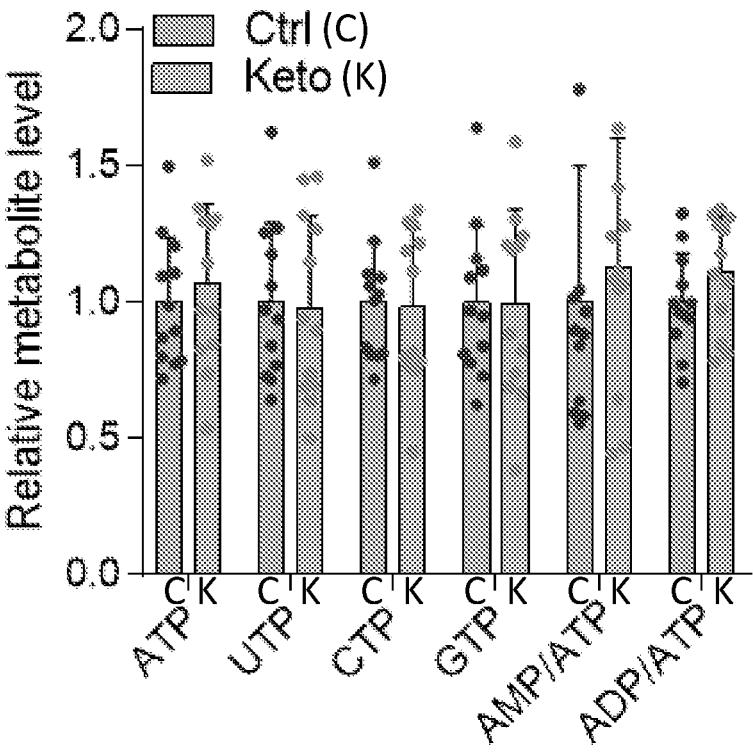
FIG. 3I shows that ketogenic diet maintains the levels of nucleotides. Mean±sem, n=12.
Figure 3J:
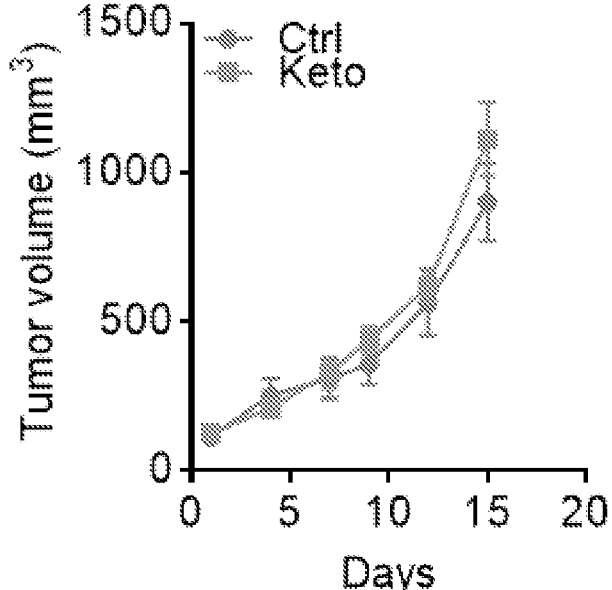
FIG. 3J shows allograft tumor volumes for diet only without chemotherapy (batch #2, mean±sem, n=8 mice per group).
Figure 3K:
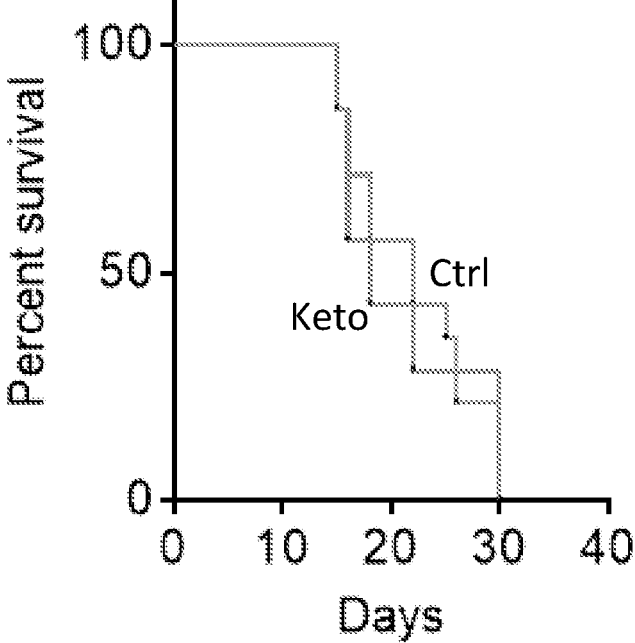
FIG. 3K shows a Kaplan-Meier curve for diet only without chemotherapy (n=14 mice per group).
Figure 3L:
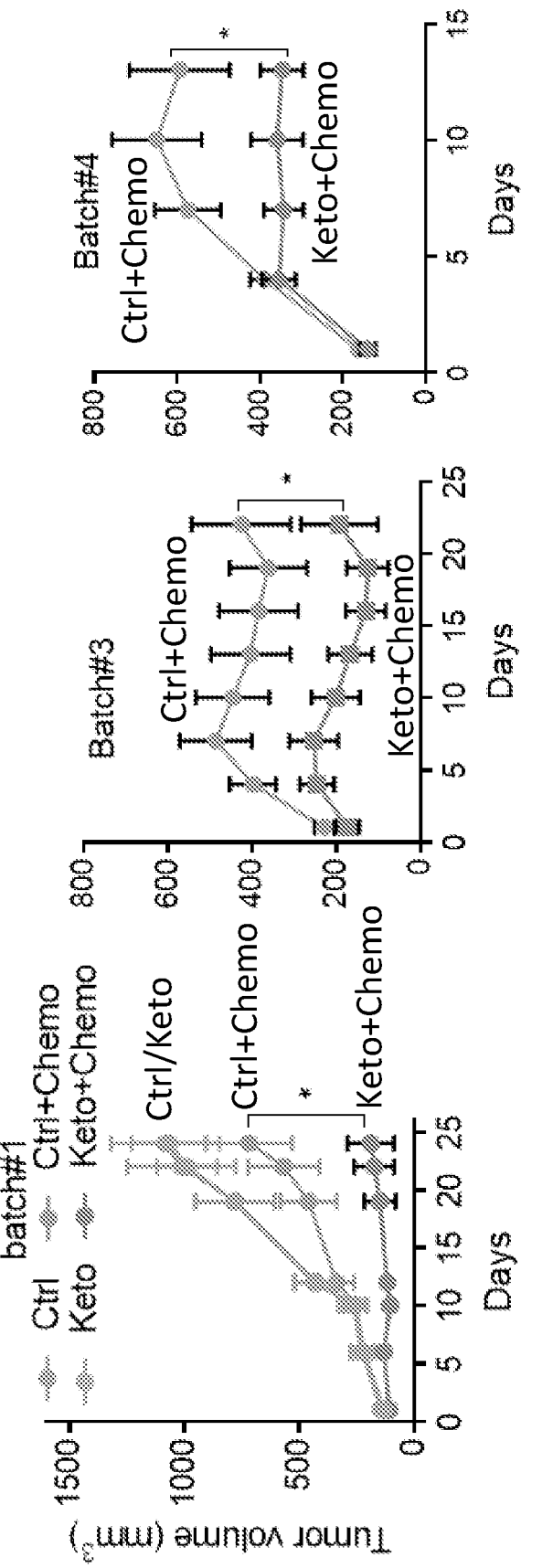
FIG. 3L shows allograft tumor volumes (batch #1, mean±sem, n=6, 6, 5, 8 for Ctrl, Keto, Ctrl+Chemo and Keto+Chemo group; batch #3, mean±sem, n=8 mice per group; batch #4, mean±sem, n=7, 8 for Ctrl+Triple and Keto+Chemo groups).
Figure 3M:
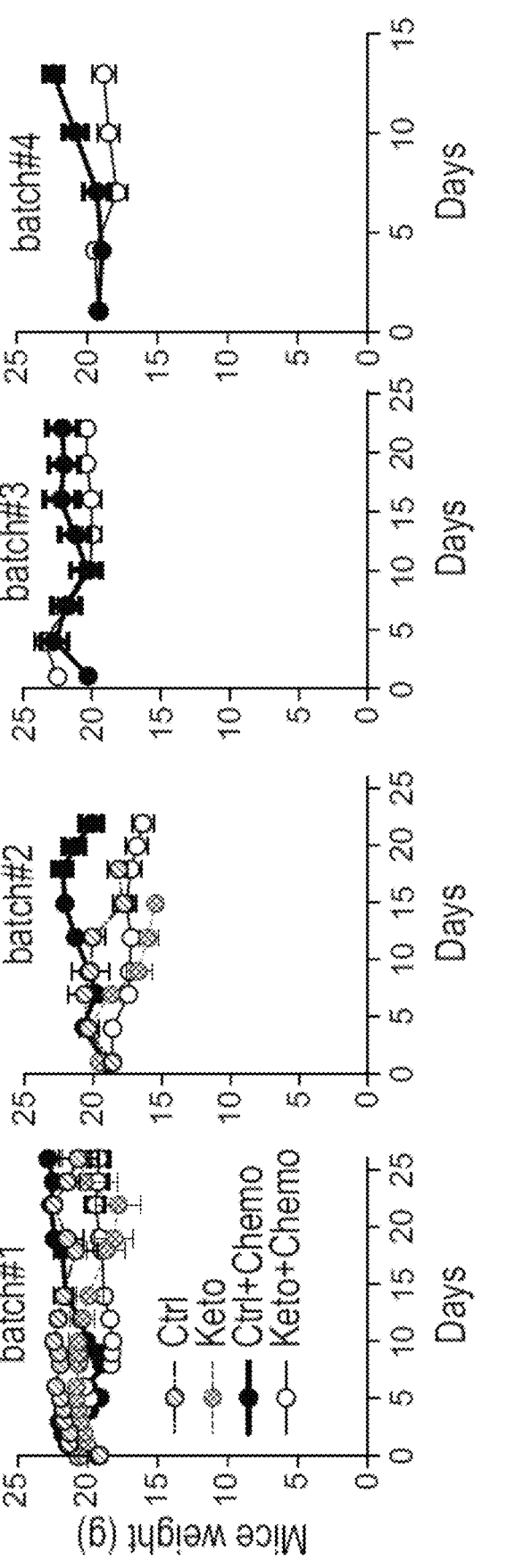
FIG. 3M shows body weight of allograft mice.
Figures 3N, 3O:
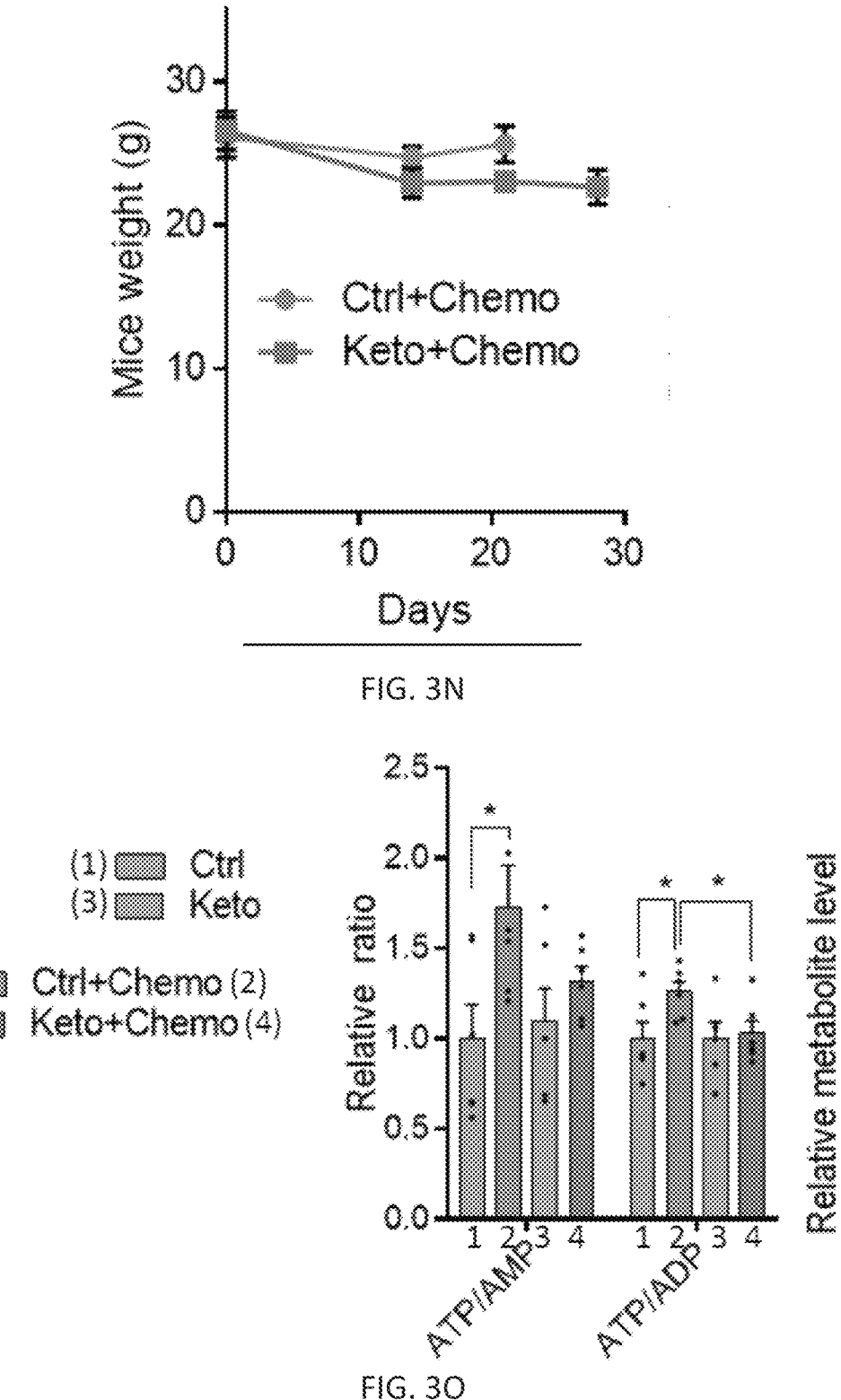
FIG. 3N shows body weight of GEMM KPC mice.
FIG. 3O shows relative intratumoral energy charge. Mean±sem, n≥4.

Similar studies were conducted in genetically engineered tumors arising spontaneously within the pancreas of KPC mice, and significant survival benefits for the triple chemotherapy-ketogenic diet combination was again observed (FIGS. 3D, 3E, 3N). Thus, ketogenic diet robustly augments the effectiveness of cytotoxic chemotherapy for KPC murine pancreatic cancer.

Ketogenic diet and classical chemotherapy elevate the NADH/NAD ratio. To investigate potential metabolic mechanisms underlying the effectiveness of the triple chemotherapy-ketogenic diet combination, tumors were harvested 24 h following the second day of chemotherapy and metabolomic analysis was carried out. Surprisingly, triple chemotherapy alone increased the tumor NADH:NAD ratio, perhaps indicating chemotherapy-induced damage to tumor oxygen supply or mitochondrial function (FIG. 3F). Ketogenic diet also increased NADH:NAD ratio in tumor (FIG. 3F). When tumors in all four treatment groups were analyzed together, a significant negative correlation between NADH:NAD ratio and tumor growth was observed (FIG. 3G): tumors with the highest NADH:NAD ratio tended to have regressed in the week prior to harvest, while those with low ratios had grown markedly.

Figure 3P:
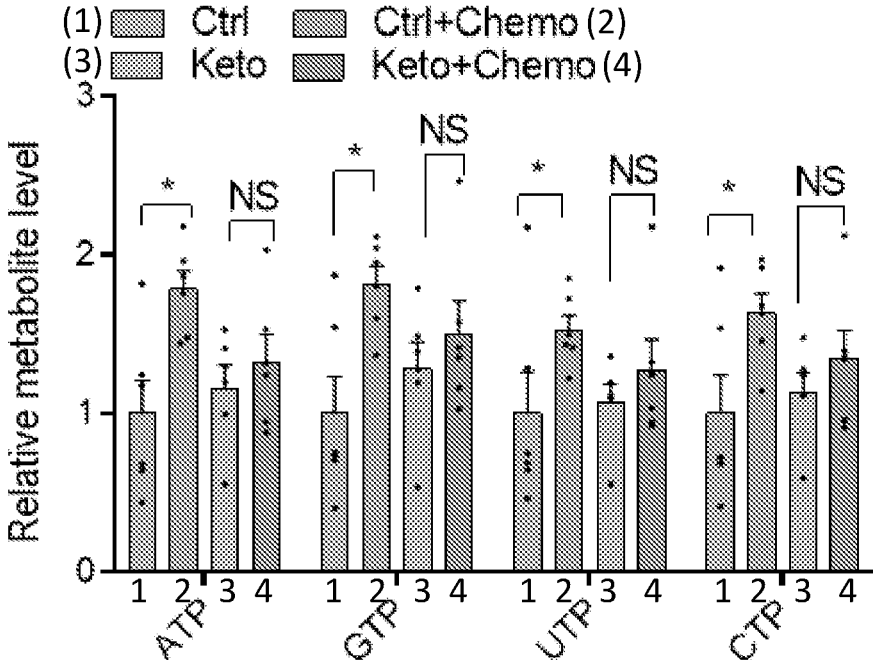
FIG. 3P shows relative nucleotide levels. Mean±sem, n≥4.

Cells with impaired respiration can maintain ATP production by inducing glycolysis. Consistent with the triple chemotherapy impairing respiration, on control diet, chemotherapy-treated tumors showed increased significant increases of glycolytic intermediates including fructose-bisphosphate and 3-phosphoglycerate (FIG. 3H). This apparent shift towards more glycolytic metabolism was associated with elevated energy charge and nucleotide levels (perhaps also reflecting decreased nucleotide consumption for nucleic acid synthesis in the chemotherapy-treated tumors) (FIGS. 3O and 3P). These adaptive metabolic responses to chemotherapy were ablated by ketogenic diet, with intratumoral glucose levels lowest in the triple chemotherapy plus ketogenic diet condition (FIG. 3H). Thus, ketogenic diet and chemotherapy induced glucose depletion and NADH accumulation (indicative of tumor reductive stress), and these metabolic changes correlated with better antitumor activity.

Figure 4A:
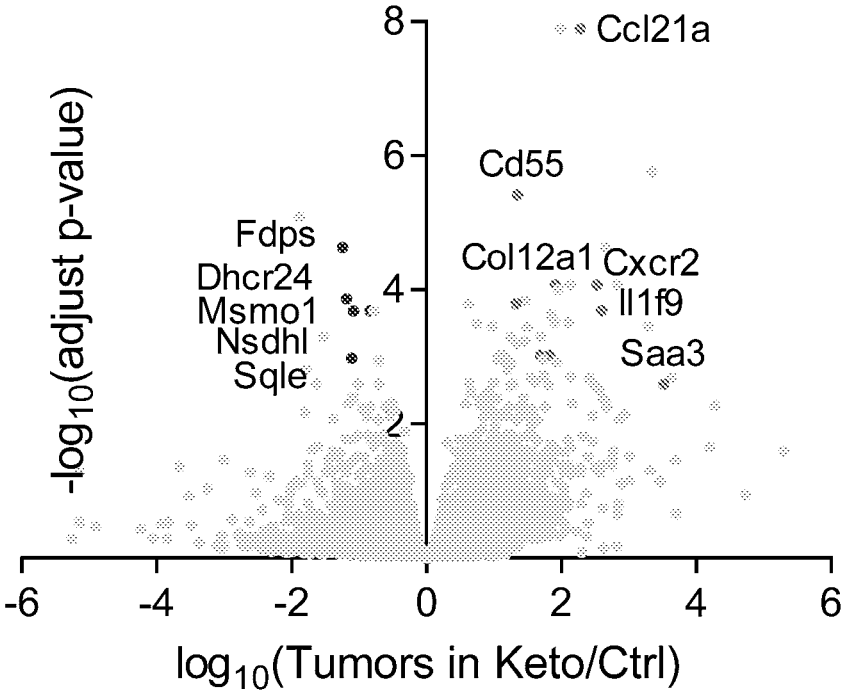
FIG. 4A shows gene expression in allograft KPC tumors of mice fed control or ketogenic diet. Ketogenic diet increases expression of genes related to the immune response and reduces expression of genes related to cholesterol synthesis.
Figure 4B:
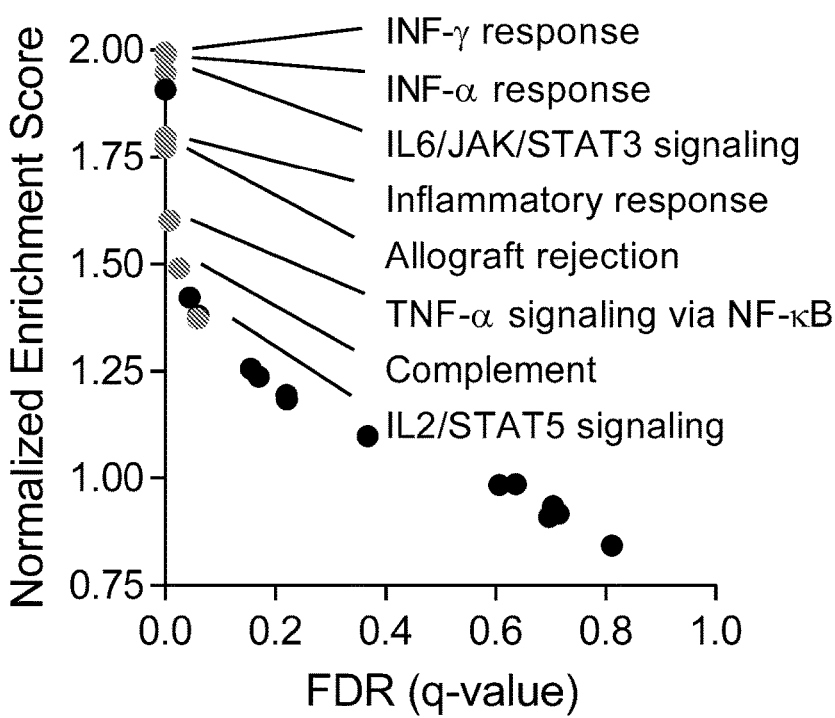
FIG. 4B shows gene set enrichment analysis (GSEA) highlights increased intratumoral immune response in mice fed with ketogenic diet.
Figure 4C:
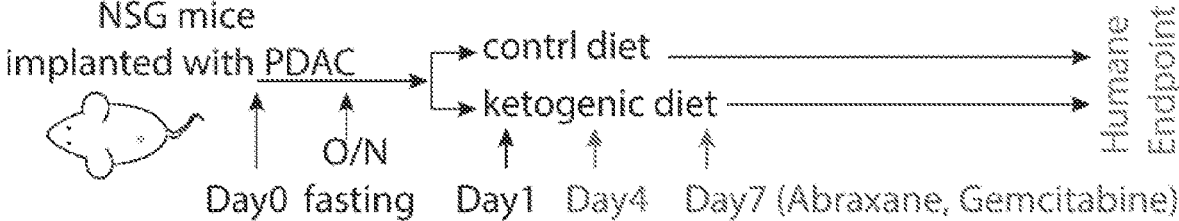
FIG. 4C shows chemotherapy regimen (nab-paclitaxel, gemcitabine) for immunocompromised NSG mice with KPC tumor allografts.
Figure 4D:
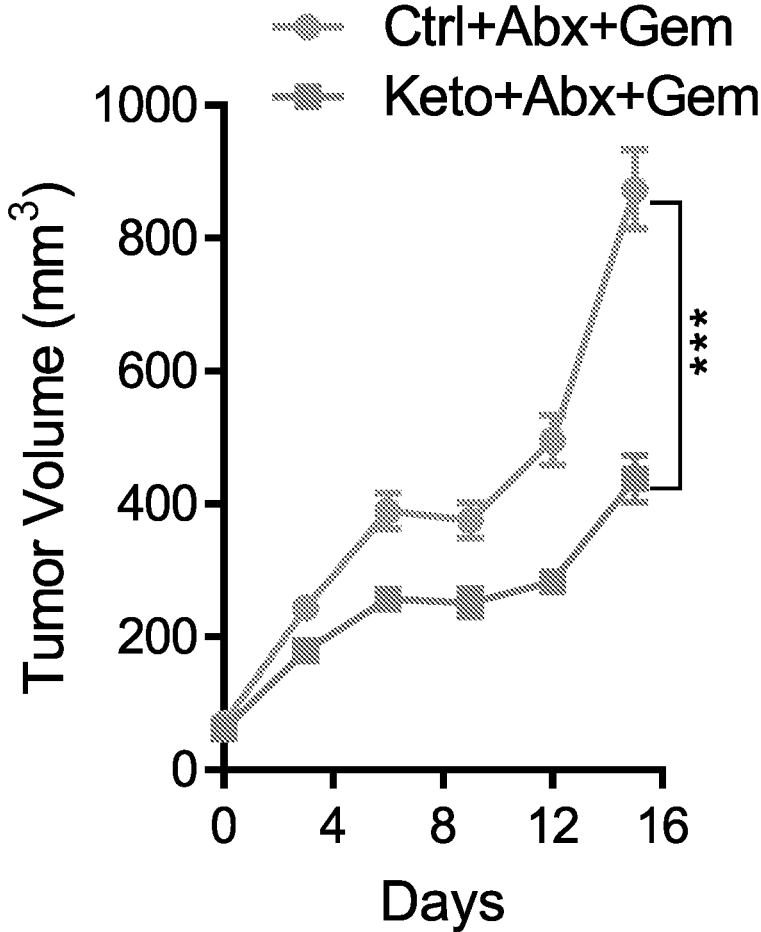
FIG. 4D shows tumor volumes in NSG mice (mean±sem, n=12 for control diet, n=11 for ketogenic diet).
Figure 4E:
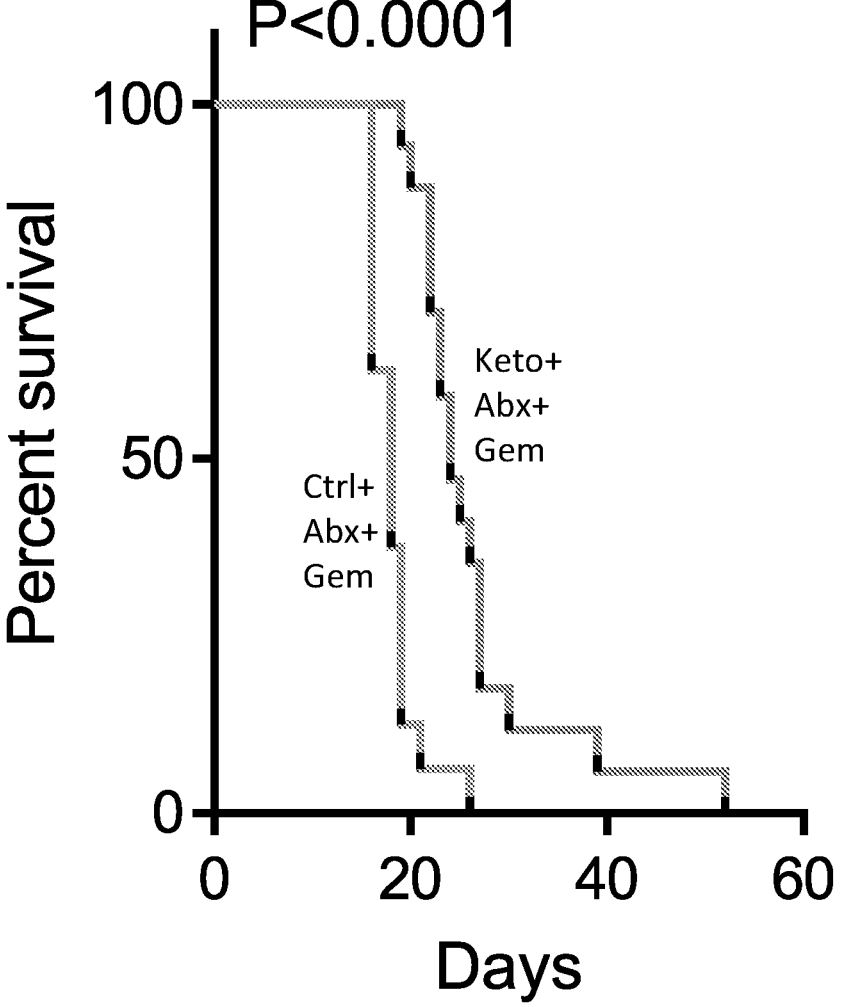
FIG. 4E shows a Kaplan-Meier curve (n=17 mice per group).
Figure 4F:
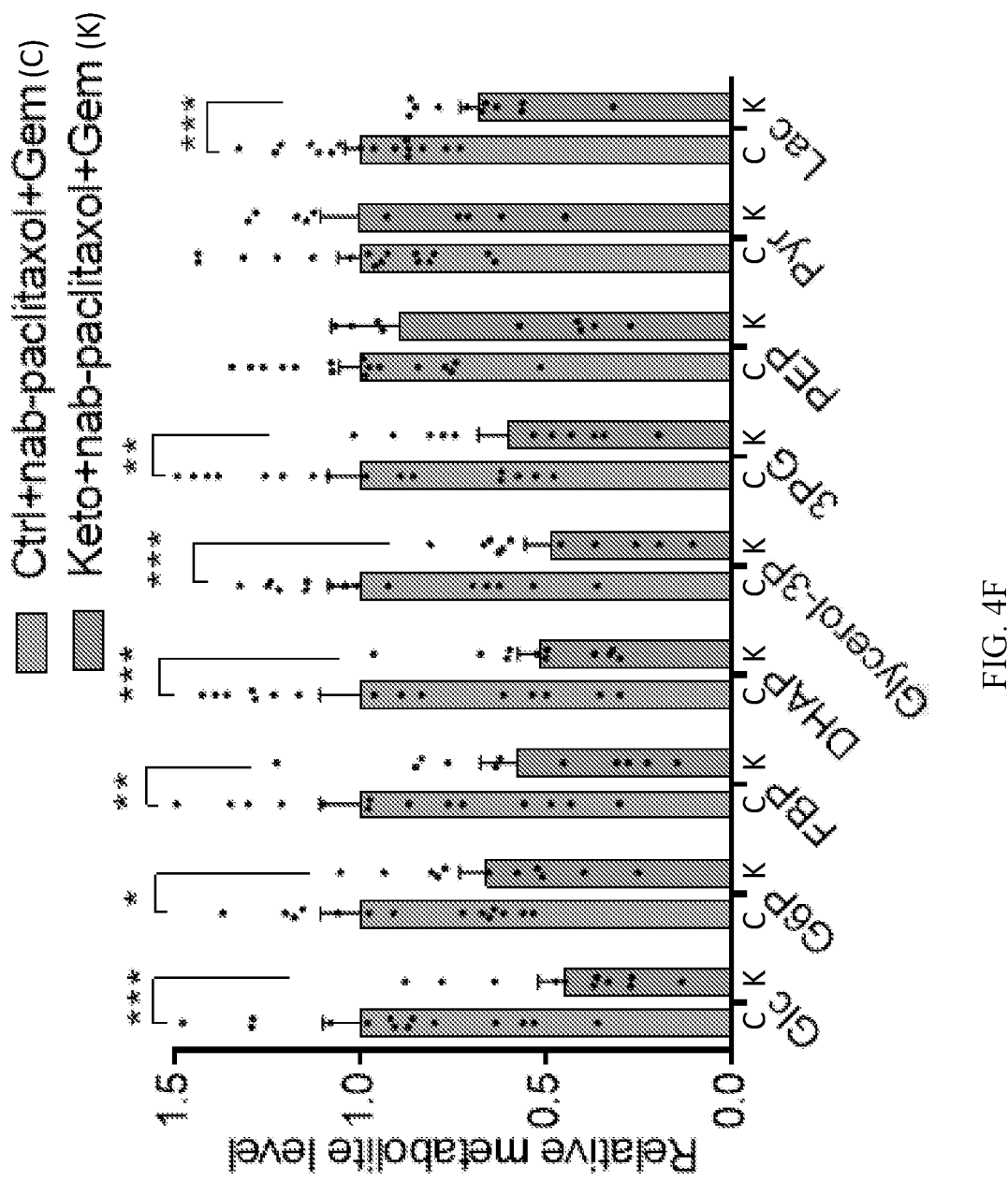
FIG. 4F shows intratumoral glycolytic metabolite levels (n=16 for control diet, n=11 for ketogenic diet).
Figure 4G:
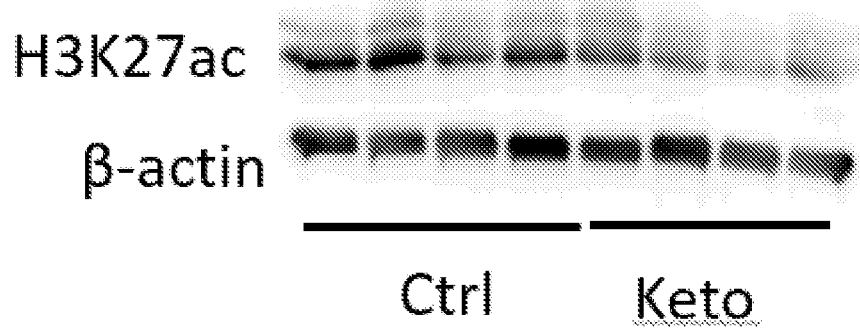
FIG. 4G shows H3K27ac histone acetylation blot for KPC tumors in control or ketogenic diet.
Figure 4H:
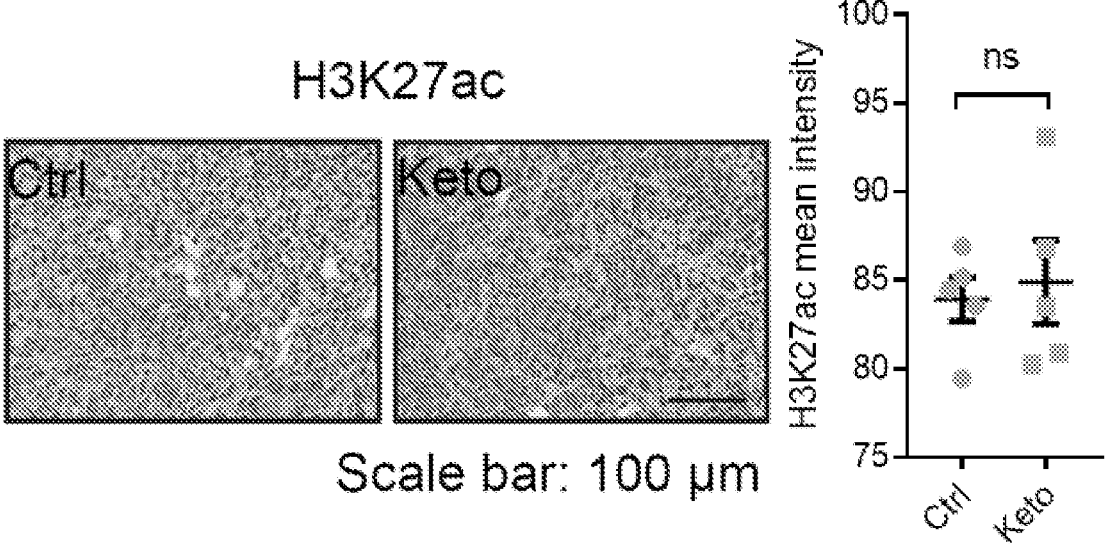
FIG. 4H shows IHC staining for H3K27ac for KPC tumors (representative image) and associated quantification across five images. Scale represents 100 μm. Mean±sem, n=5.
Figure 4I:
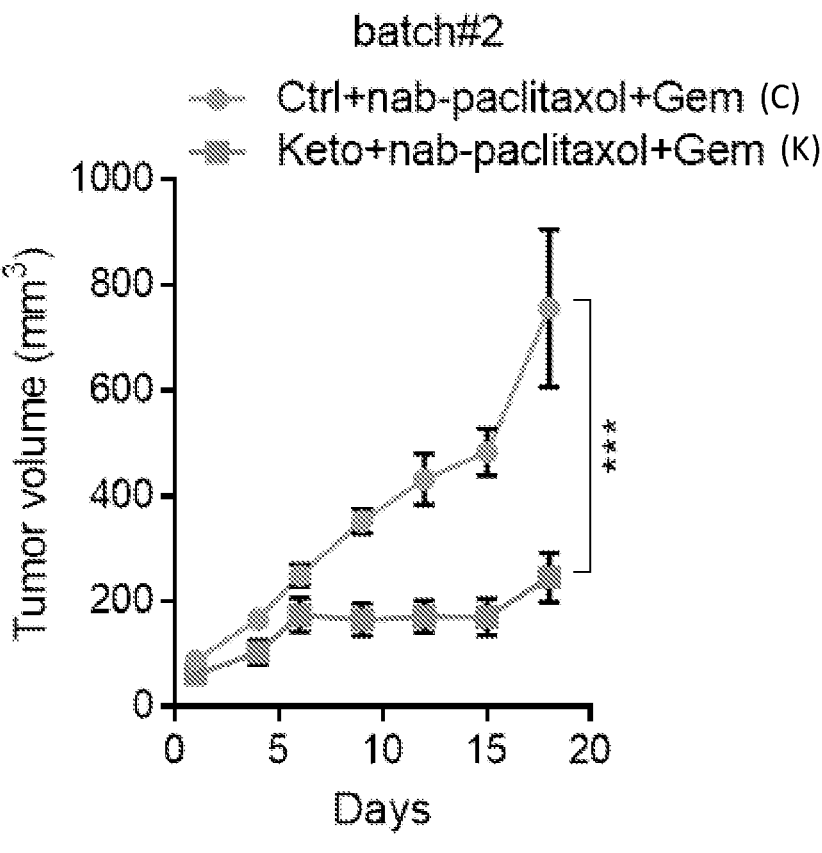
FIG. 4I shows tumor volumes in NSG mice. Mean±sem, n=5 for control diet, n=6 for ketogenic diet.
Figure 4J:
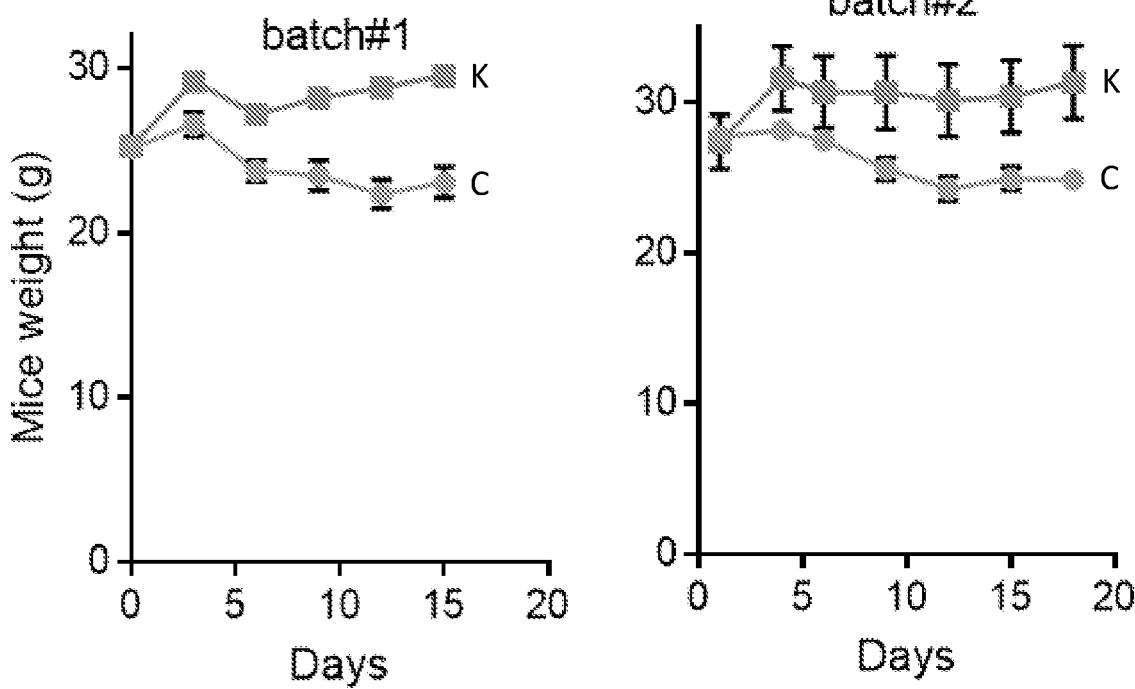
FIG. 4J shows body weight of NSG mice.

Ketogenic diet induces inflammatory gene expression in the tumor. To further explore potential mechanisms by which ketogenic diet may sensitize tumors to chemotherapy, RNA was extracted from tumors 7 days after mice were switched to either control or ketogenic diet. Overall, the tumor gene expression signature was only modestly altered. Analysis of histone acetylation showed no trend towards increased acetylation in the ketogenic diet tumors, arguing against histone deacetylation inhibition as the key ketogenic diet mechanism (FIGS. 4G and 4H). Instead, the few significantly altered gene sets revolved around inflammation: the most upregulated gene sets were the IFN response, IL6/JAK/STAT3 signaling and inflammatory response (FIGS. 4A and 4B).

Figure 4K:
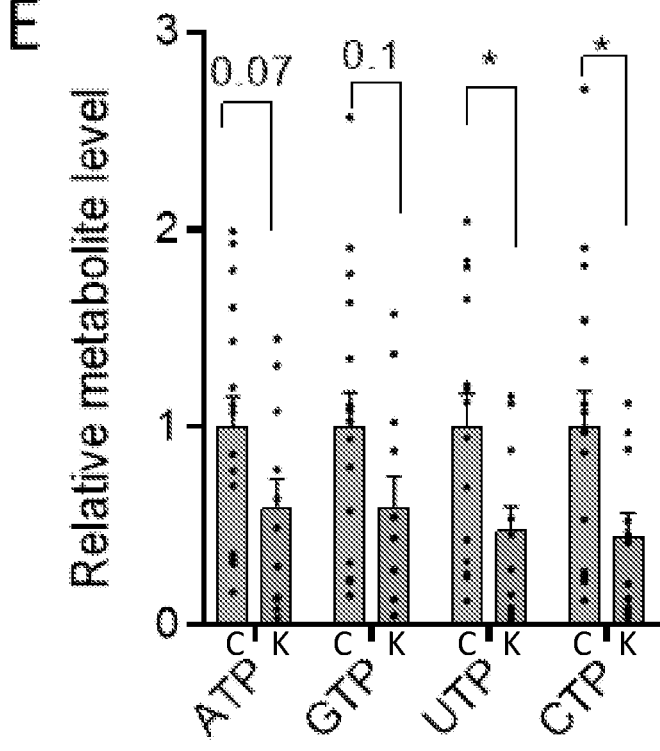
FIG. 4K shows relative intratumor nucleotide levels. Mean±sem, n=16 for control diet, n=11 for ketogenic diet.

Motivated by these findings, studies combining ketogenic diet and triple chemotherapy were attempted in immunodeficient NSG mice, but NSG mice did not tolerate the triple chemotherapy. Accordingly, the standard of care therapy of gemcitabine and nab-paclitaxel without cisplatin was administered. Despite the lack of an adaptive immune system, in combination with chemotherapy, ketogenic diet suppressed tumor growth and augmented lifespan, indicating direct antitumor activity (FIGS. 4C-4E, 4I, 4J). Among chemotherapy-treated tumors, in the NSG mice, depletion of glycolytic intermediates and nucleotide triphosphates was again observed in the ketogenic diet condition (FIGS. 4F and 4K). The improvement in overall survival due to ketogenic diet was, however, less than in the immunocompetent mice, with no durable tumor control, suggesting that the durable therapeutic benefits in immunocompetent mice on the ketogenic diet involve a component of immune surveillance.

Discussion

Aerobic glycolysis was the first molecular phenotype assigned to cancer and underlies tumor diagnosis by fluorodeoxyglucose PET imaging. But, efforts to pharmacologically target tumor glycolysis, or other central metabolic pathways, have yet to succeed clinically. An alternative way to target tumor metabolism is via diet. Ketogenic diet—mainly fat and very low carbohydrate—suppresses the normal feeding-induced insulin spike and produces persistently elevated circulating ketone bodies, mimicking a chronic fasted state. Here, it is shown that, in KPC tumors, ketogenic diet synergizes with the clinically active cytotoxic chemotherapy regimen, gemcitabine, nab-paclitaxel, and cisplatin. Strikingly, while having no effect on tumor growth on its own, ketogenic diet triples the survival benefits of the triple chemotherapy. If this were to translate directly to the clinic, the roughly one-year survival benefit of gemcitabine, nab-paclitaxel, cisplatin would elongate to around 3 years, approaching 5-year survival for metastatic pancreatic cancer.

What is the metabolic effect of ketogenic diet in tumors? It is been suggested that tumors do not burn ketone bodies, and indeed on control diet this is the case for pancreatic cancer. But on ketogenic diet, KPC pancreatic cancer tumors avidly burn ketones, to more than double the extent of regular pancreas. This was visualized by imaging mass spectrometry of primary KPC tumors, which revealed the strongest contribution of 3HB in regions of peritumoral fibrosis.

One likely driver of the avid tumor ketone body uptake is high MCT expression. Commonly thought of as lactate exporters, in regular diet, MCTs can enhance tumor growth by promoting glycolysis and redox homeostasis. But MCTs are not specific lactate exporters. Depending on intracellular and environmental levels and pH, MCTs can catalyze uptake or excretion of lactate, pyruvate, 3HB. In ketogenic diet, high 3HB hijacks tumor MCTs, driving tumor ketone catabolism.

Rapid ketone catabolism generates mitochondrial NADH, which, in the context of a poorly perfused tumor like pancreatic cancer, can lead to accumulation of reduced respiratory chain complexes resulting in oxygen radical generation. Unexpectedly, in addition to ketogenic diet increasing tumor NADH, so did triple chemotherapy. The rise in NADH/NAD ratio induced by therapy correlated, across different allograft tumors on control or ketogenic diet, with therapeutic response, with high NADH associated with tumor regression.

In addition to modulating tumor NADH, ketosis may augment sensitivity to chemotherapy by suppressing histone deacetylation, insulin signaling, or tumor glycolysis. It was observed here that ketogenic diet suppressed tumor glucose levels and associated TCA intermediate labeling. In the standard diet, triple chemotherapy elevated glycolytic intermediate levels. This response was blocked by ketogenic diet, and tumor glucose levels were lowest in the combined chemotherapy-ketogenic diet condition. Thus, glycolysis may be particularly critical for tumor cells to survive chemotherapy, and, by limiting glucose availability, ketogenic diet may promote chemotherapy efficacy.

Moreover, ketogenic diet may impact antitumor immunity. In immunocompetent mice, ketogenic diet induces pro-inflammatory tumor gene expression. This is not essential for the chemotherapy-ketogenic diet synergy, as the therapeutic benefits occur also in mice lacking an adaptive immune system. But, the immune system likely contributes to long-term tumor control.

Methods

Mouse husbandry and PDAC tumor models. All mouse work was approved by the Institute Animal Care and Use Committees (IACUCs) at Princeton University or the University of Arizona. Wild type C57BL/6 mice were obtained at 8-weeks of age from Charles River Laboratories and NSG (NOD.Cg-Prkdc$^{scid}$Il2rg$^{tm1\,Wjl}$/SzJ) mice were obtained at 8-weeks of age from Jackson Laboratory. The KPC (Kras$^{LSL-G12D/+}$Trp53$^{R172H/+}$Pdx-1-Cre) mice were generated from three mouse parental strains (LSL-Kras$^{G12D/+}$; LSL-Trp53$^{R172H/+}$; and Pdx-1-Cre) obtained from National Cancer Institute (NCI) mouse repository and following established procedures described by Hingorani and colleagues (Hingorani et al., 2005). All mice were housed under normal light cycle (7:00-19:00) and fed a standard chow diet ad lib (PicoLab Rodent 5053 laboratory Diet St. Louis, MO). NSG mice were provided with acidic drinking water (pH 3.0), which was refreshed weekly. Syngeneic PDAC allograft tumors were established by harvesting tumors from KPC mice, mincing the tissue with surgical scissors into small particles able to pass through a 16 G needle, suspending in DMEM medium, mixing with Matrigel (Corning Cat #354234) at a 1:1 ratio (v/v), and then injecting 200 microliters of the mixture subcutaneously into the mouse flank. Allograft tumors were passaged up to two times in syngeneic recipient mice before implantation for use in experiments. Further passaging diminished ketogenic diet responsiveness. Tumor growth was monitored by measuring the tumor dimensions (length, width and height) twice per week using a caliper. Tumor volume was calculated as 0.5× (Length×Width×Height).

Tumor monitoring and chemotherapy. KPC tumor tissue was implanted into flanks of C57BL/6 or NSG mice. Once the tumors were palpable, mice were fasted overnight (16 h) and randomly assigned to standard chow or ketogenic (Bioserv, S3666) diet groups. The ketogenic diet was served in a petri dish and replaced every other day. For studies with PDAC GEMM, KPC mice were monitored biweekly for tumor development using high resolution ultrasound imaging (Visualsonics Vevo 770 system, Fujifilm VisualSonics, Ontario, Canada) and upon tumor sizes reaching 150 mm$^3$, mice were randomly assigned to treatment groups.

The triple chemotherapy regimen included nab-paclitaxel (NDC code: 68817-134-50) dosed at 50 mg/kg via retro-orbital injection, gemcitabine (NDC code: 0409-0181-01) at 70 mg/kg via intraperitoneal injection and cisplatin (sigma PHR1624) at 4 mg/kg via intraperitoneal injection. This triple chemotherapy regimen was administrated three days and six days (day 4 and 7) post-dietary group assignment, with cisplatin omitted for the NSG mice due to poor tolerability. Mouse weight and tumor sizes were monitored until humane endpoint was reached (20% weight loss or tumor size of 1,000 mm$^3$ or tumor length of 20 mm).

Isotope tracer infusion. For lactate circulatory turnover flux measurements, 10-14 weeks old C57BL/6 mice were catheterized via both left carotid artery and right jugular vein, as non-perturbative arterial blood sampling is required for precise measurement of circulating lactate labeling. Mice were allowed to recover for 5 days. Mice were fasted from ZT2 to ZT6.5. Sodium [2-$^2$H] or [U-$^{13}$C]lactate solution was diluted to 5% w/w in water, and infused into the double catheterized mice from ZT6.5 to ZT9 to pseudo steady state. Arterial blood was sampled to calculate the turnover rate for $^2$H or $^{13}$C lactate.

For other tracing experiments, 10-14 weeks old C57BL6/J mice or mice bearing tumors (KPC flank allografts or Kras$^{LSL-G12D/+}$Trp53$^{-/-}$Pdx-1-Cre GEMM, tumor sizes ~150 mm$^3$) were catheterized via right jugular vein. Mice were allowed to recover from surgery for 3-5 days. For 3HB circulatory turnover flux experiments, mice were fasted from ZT2 to ZT6.5, and [3,4,4,4-$^2$H] or [U-$^{13}$C]3HB were infused to catheterized mice from ZT6.5 to ZT9. Tail blood was sampled to calculate the turnover rate for $^2$H or $^{13}$C 3HB.

To compare the turnover rates of nutrients for mice in different diets, catheterized mice were fasted overnight (16 hours) and then fed a standard chow or ketogenic diet for 1 week. Isotope tracers were infused into the jugular vein catheter at a steady rate for 2.5 hours (ZT14-ZT16.5) followed by tail blood collection, euthanasia by cervical dislocation and tissue (tumor, pancreas) harvesting.

For metabolomics studies, tail blood and tissues were collected from ad lib fed mice at ZT16 on day 7 post-dietary group assignment (one day after second dosage of chemotherapy in those treatment groups).

Blood samples were cooled on ice to coagulate and then serum was collected following centrifugation at 16,000×g for 10 minutes at 4° C. Tissues samples were collected by clamping in aluminum foil with a pre-cooled Wollenberger like clamp and immediately transferred into liquid nitrogen. All serum and tissues samples were stored at −80° C. until further analysis.

LC-MS sample preparation. Tissue samples were dissected into small pieces, transferred into 2 ml Eppendorf tubes, and pulverized using a Cryomill (Retsch). 10-20 mg of the resulting tissue powder was weighed into a pre-cooled Eppendorf tube for metabolite extraction. Water soluble metabolites were extracted with 40:40:20 methanol:acetonitrile:water with 0.5% formic acid pre-cooled to −20° C. Extraction solvent was added at 40× the sample quantity (400 μl of extraction buffer per 10 mg of tissue powder and 120 μl of extraction buffer per 3 μl serum). After vortexing for 10 s and keeping samples in ice for 10 min, samples were neutralized by adding 15% ammonium bicarbonate (NH$_4$HCO$_3$) aqueous solution (8.75% v/v of extraction buffer). Samples were then again mixed by vortexing for 10 s, centrifuged at 16,000×g for 30 min at 4° C., and then supernatant was transferred to LC-MS vials for analysis. In FIG. 2A, internal standards of glucose, lactate, and 3-HB were spiked into solution. 1 mg of tissue sample was consider to equal 1 ml.

LC-MS method. Water soluble metabolite measurements were obtained by running samples on the Q Exactive PLUS hybrid quadrupole-orbitrap mass spectrometer (Thermo Scientific) coupled with hydrophilic interaction chromatography (HILIC). An XBridge BEH Amide column (150 mm×2.1 mm, 2.5 μM particle size, Waters, Milford, MA) was used. The gradient was solvent A (95%:5% H$_2$O: acetonitrile with 20 mM ammonium acetate, 20 mM ammonium hydroxide, pH 9.4) and solvent B (100% acetonitrile) 0 min, 90% B; 2 min, 90% B; 3 min, 75%; 7 min, 75% B; 8 min, 70%, 9 min, 70% B; 10 min, 50% B; 12 min, 50% B; 13 min, 25% B; 14 min, 25% B; 16 min, 0% B, 20.5 min, 0% B; 21 min, 90% B; 25 min, 90% B. The flow rate was 150 μL/min with an injection volume of 5 μL and a column temperature of 25° C. The MS scans were in negative ion mode with a resolution of 140,000 at m/z 200. The automatic gain control (AGC) target was 1×10$^6$ and the scan range was m/z 75-1000. All data from isotope labeling experiments were analyzed by El-MAVEN with natural abundance correction.

Acetate measurements. 5 μL serum was added to 100 μL of 12 mM 1-ethyl-3-(3-dimethylaminopropyl) carbodiimide (EDC), 15 mM 3-Nitrophenylhydrazine and pyridine (2% v/v) mixture in methanol, incubated at 4° C. for 1 h, centrifuged for 10 min at 16,000×g, and then the supernatant quenched with 0.5 mM beta-mercaptothion and 0.1% formic acid in water. The resulting samples were used for LC-MS analysis with negative mode electrospray ionization scanning m/z from 100 to 300 at 1 Hz with 140,000 resolution on Q Exactive. LC separation was reversed phase C18 on an Acquity UPLC BEH C18 column (2.1 mm×100 mm, 1.7 5 µm particle size, 130 Å pore size; Waters, Milford, MA) using a gradient of solvent A (water), solvent B (methanol): 0 min, 10% B; 1 min, 10% B; 5 min, 30% B; 7 min, 100% B; 11 min, 100% B; 11.5 min, 10% B; 14 min, 10% B. Flow rate was 200 µL/min and column temperature was 60° C. with an injection volume of 10 µL.

RNA preparation and RNA-seq analysis. Total RNA was extracted using TRIzol (Invitrogen, 15596026) from snap-frozen tumor samples. RNA quality was confirmed using the Agilent 2100 Bioanalyzer. Libraries were prepared from 100-500 ng of total RNA with barcoded multiplexing. Single-end sequencing was carried out on an Illumina HiSeq 2500 with a 100-bp read length. For image analysis and base calling, Illumina CASAVA-1.8.2 were utilized. After the read quality was assessed with fastqc, reads were mapped against the reference genome and transcript annotation (GRCm38.p6) using STAR (Dobin et al., 2013) with the default setting plus the "--quantMode TranscriptomeSAM" and "--outSAMtype BAM" options. Gene expression was quantified from the BAM files by RSEM (Li and Dewey, 2011) using the "rsem-calculate-expression" function with the "--estimate-rspd" and "--append-names" options. Differential expression gene analysis was performed with DESeq2 (Love et al., 2014). Briefly, the results of RSEM were imported by the "DESeqDataSetFromTximport" function in the tximport package with the following options: "type='rsem', txIn=FALSE, txOut=FASLE". After the establishment of DESeq data set "estimateSizeFactors", counts were normalized with the "counts" function. Differential expression analysis between Keto-Diet and Chow-Diet was performed with the "DESeq" command, and the results exported by the "results" command.

MALDI imaging mass spectrometry. At time of harvesting, tumor samples were snap-frozen on dry ice for 30 min and stored at −80° C. until sectioning. 10 µm-thick tumor sections were collected on a cryomicrotome (Leica CM3050S, Wetzlar, Germany). Then the tissues were thaw-mounted on indium tin oxide (ITO)-coated glass (Bruker Daltonics, Bremen, Germany) and kept in desiccator under vacuum for 20 mins. Serial sections were collected on standard glass slides for H&E staining.

Tissue sections after desiccation were coated with matrix by spraying 10 mg/ml N-(1-naphthyl) ethylenediamine dihydrochloride (NEDC) in 70% MeOH using an HTX TM-Sprayer (HTX Technologies, LLC). The sprayer temperature was set to 80° C. with a flow rate of 0.1 ml/min, a velocity of 1000 mm/min, track spacing of 2 mm and pressure of 10 psi. Ten passes of matrix were applied to each slide with 30 s of drying time between each pass. The MALDI-FTICR measurements were obtained using a solarix XR FTICR mass spectrometer equipped with 9.4 T magnet and parcel (Bruker Daltonics, Bremen, Germany). The resolving power of the parcel was R=120,000 at m/z 500. The x-y raster width was set to 50 µm using Smartbeam-II laser optics. A spectrum was accumulated from 300 laser shots at 1200 Hz. All images and isotope data was examined and analyzed using the open-source in-house software IsoScope.

Kinetic isotope effect (KIE) measurements. In vitro enzyme assays were carried out to assess the KIE for lactate dehydrogenase and 3HB dehydrogenase. 20 mM [U-$^{13}$C] sodium lactate, [2-$^2$H]sodium lactate, [U-$^{13}$C]sodium 3HB, and [3,4,4,4-$^2$H]sodium 3HB substrate solutions were prepared in advance. 200 mM Tris pH 8.0 and 25 mM NAD (Sigma N0632) solutions were prepared on day of experiment. Lactate dehydrogenase (Sigma 59747), and hydroxybutyrate dehydrogenase (Sigma 10127833001) enzymes were diluted to 0.5 U/ml. Solution A, consisting of 12.5 µl of Tris buffer, 1 µl of NAD solution, 24.5 µl of water, and 2 µl of enzyme solution, was prepared as a mixture and added directly in half-area 96 well plates (Corning 3881). 10 µl of each substrate solution was added into solution A and NADH absorbance was measured at 340 nm. For each enzyme and substrate combination, the NADH absorbance was plotted over time to determine the slope and the kinetic isotope effect was calculated from the ratio of the $^{13}$C-substrate slope to the $^2$H-substrate slope.

Western blotting for histone acetylation. Pulverized tumor tissue was weighed (10 mg) and proteins were extracted with RIPA buffer (Millipore: 20-188) containing proteinase inhibitor (Roche: 4693159001) for 1 hour, followed by centrifuging at 16,000 g for 10 mins to get supernatant. Protein concentrations were determined using Pierce BCA protein assay kit (ThermoFisher #23225). Around 20 µg of protein was loaded (mixed with loading buffer) into 4-20% gel (Bio-Rad: 4568095), transferred onto membrane, incubated with primary antibodies against 3-actin (Cell Signaling #4970) or H3K27ac (Abcam, ab4729), washed with TBST, incubated with secondary antibody and visualized using the Bio-Rad ChemiDoc MP system.

Immunohistochemical staining. Tumor specimens from the mouse models were fixed by immersing in 10% buffered formalin overnight at 4° C. and maintained in 70% ethanol for paraffin embedding. Immunohistochemical staining was performed with an antibody against H3K27ac (1:1000; Abcam, ab4729) and Immunohistochemistry Application Solutions Kit (Cell Signaling, 13079), following the manufacturer's protocols. Antigen retrieval was performed in a pressure cooker for 15 min with citric acid-based buffer, pH 6.0 (Vector Labs, H-3300). Slides were scanned using a VS-100 scanning microscope (Olympus), and quantifications was performed with ImageJ.

Metabolic flux quantitation. Circulatory turnover flux, $F_{circ}$ was calculated as previously described (Hui et al., 2017), using arterial serum for lactate due to its substantial arterial-venous labeling gradient and tail vein serum for other nutrients:

$$F_{circ} = R \cdot \frac{1-L}{L}$$

R is the infusion rate of the labeled tracer and L is the fractional enrichment of infused labeled form of the metabolite tracer. $F_{circ}$ values of $^2$H-labeled metabolites were corrected for kinetic isotope effect (KIE, determined from the enzymatic assays) by multiplying the observed $F_{circ}$ by KIE value of $^2$H tracer.

To calculate the average carbon atom labeling of metabolites, the following formula was used:

$$L_{avg} = \frac{\sum_{i=0}^{N} \frac{i}{N} \cdot M_i}{\sum_{i=0}^{n} M_i}$$

N is the number of carbon atoms (including both 12C and 13C) in the metabolite, i is the number of $^{13}$C atoms in the metabolite, and M is the measured abundance of the given isotopic form (when M is reported in fractional abundance, as is common, then the denominator is 1 and can be omitted). The normalized carbon labeling of downstream metabolite (Y) from a tracer (X) is then calculated by dividing the average carbon labeling of the metabolite of interest (either in serum or tissues) to the average carbon labeling of the tracer in serum.

$$L_{Y \leftarrow X} = \frac{L_{Y,avg}}{L_{X,avg}}$$

The direct contribution of circulating nutrients to the metabolites of interest is calculated using the logic described previously (Hui et al., 2017, 2020). Basically, every $^{13}$C-labeled carbon in each metabolite of interest can derived from two ways: directly from the tracer or indirectly from another circulating nutrient labeled by the tracer. By performing independent infusions of each circulating nutrient that labels the metabolite of interest, the direct contribution of each circulating nutrient to a given metabolite pool can be solved for. For example, to calculate the direct contribution of glucose and lactate to the TCA metabolite malate within a KPC tumor, two equations can be written:

$$L_{tumor\ mal\leftarrow glc} = L_{serum\ glc\leftarrow glc} \cdot f_{mal\leftarrow glucose} + L_{serum\ lac\leftarrow glc} \cdot f_{mal\leftarrow lac}$$

$$L_{tumor\ mal\leftarrow glc} = L_{serum\ glc\leftarrow glc} \cdot f_{mal\leftarrow glucose} + L_{serum\ lac\leftarrow glc} \cdot f_{mal\leftarrow lac}$$

Where $L_{tumor\ mal\leftarrow glc}$ and $L_{serum\ lac\leftarrow glc}$ represent normalized carbon labeling of tumor malate or serum lactate from U-$^{13}$C glucose tracer, $L_{tumor\ mal\leftarrow lac}$ and $L_{serum\ glc\leftarrow lac}$ represent normalized labeling of tumor malate or serum glucose from U-$^{13}$C lactate tracer, and $f_{mal\leftarrow glucose}$ and $f_{mal\leftarrow lac}$ represent the direct contribution of malate from circulating glucose or lactate. As all the L values are empirically measured, the f values can be determined using linear algebra (2 equations with 2 unknowns). This logic can be expanded to multiple tracers (1 . . . n), and write the algebra matrix in the following format to solve for each f value (n equations with n unknowns):

$$\begin{pmatrix} L_{mal\leftarrow 1} \\ \vdots \\ L_{mal\leftarrow n} \end{pmatrix} = \begin{pmatrix} L_{1\leftarrow 1} & \cdots & L_{n\leftarrow 1} \\ \vdots & \ddots & \vdots \\ L_{1\leftarrow n} & \cdots & L_{n\leftarrow n} \end{pmatrix} \begin{pmatrix} f_{mal\leftarrow 1} \\ \vdots \\ f_{mal\leftarrow n} \end{pmatrix}$$

This same approach was used to calculate intratumoral pyruvate/lactate sources from [U-$^{13}$C]glucose and [U-$^{13}$C] lactate infusions. Optimization was performed in MATLAB function "fmincon". Errors of the output f were obtained by Monte Carlo simulations. Each measured element L (in both the matrix and the vector) were randomly sampled multiple times (50), assuming a normal distribution with the experimentally measured standard deviation (TeSlaa et al., 2021).

REFERENCES

Aminzadeh-Gohari, S., Feichtinger, R. G., Vidali, S., Locker, F., Rutherford, T., O'Donnel, M., Stöger-Kleiber, A., Mayr, J. A., Sperl, W., Kofler, B., et al. (2017). A ketogenic diet supplemented with medium-chain triglycerides enhances the anti-tumor and anti-angiogenic efficacy of chemotherapy on neuroblastoma xenografts in a CD1-nu mouse model. Oncotarget 8, 64728-64744.

Antoch, G., Saoudi, N., Kuehl, H., Dahmen, G., Mueller, S. P., Beyer, T., Bockisch, A., Debatin, J. F., and Freudenberg, L. S. (2004). Accuracy of whole-body dual-modality fluorine-18-2-fluoro-2-deoxy-D-glucose positron emission tomography and computed tomography (FDG-PET/CT) for tumor staging in solid tumors: comparison with CT and PET. J. Clin. Oncol. Off. J. Am. Soc. Clin. Oncol. 22, 4357-4368.

Barborka, C. J. (1928). KETOGENIC DIET TREATMENT OF EPILEPSY IN ADULTS. J. Am. Med. Assoc. 91, 73.

Bates, M. (1971). Kinetics of ketone body metabolism in fasted and diabetic rats. Am. J. Physiol.-Leg. Content 221, 984-991.

Birsoy, K., Wang, T., Chen, W. W., Freinkman, E., Abu-Remaileh, M., and Sabatini, D. M. (2015). An Essential Role of the Mitochondrial Electron Transport Chain in Cell Proliferation Is to Enable Aspartate Synthesis. Cell 162, 540-551.

Blodgett, T. M., Meltzer, C. C., and Townsend, D. W. (2007). PET/CT: form and function. Radiology 242, 360-385.

Brooks, G. A. (2018). The Science and Translation of Lactate Shuttle Theory. Cell Metab. 27, 757-785.

Caffa, I., Spagnolo, V., Vernieri, C., Valdemarin, F., Becherini, P., Wei, M., Brandhorst, S., Zucal, C., Driehuis, E., Ferrando, L., et al. (2020). Fasting-mimicking diet and hormone therapy induce breast cancer regression. Nature 583, 620-624.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Draoui, N., and Feron, O. (2011). Lactate shuttles at a glance: from physiological paradigms to anti-cancer treatments. Dis. Model. Mech. 4, 727-732.

Erkan, M., Hausmann, S., Michalski, C. W., Fingerle, A. A., Dobritz, M., Kleeff, J., and Friess, H. (2012). The role of stroma in pancreatic cancer: diagnostic and therapeutic implications. Nat. Rev. Gastroenterol. Hepatol. 9, 454-467.

Faubert, B., Li, K. Y., Cai, L., Hensley, C. T., Kim, J., Zacharias, L. G., Yang, C., Do, Q. N., Doucette, S., Burguete, D., et al. (2017). Lactate Metabolism in Human Lung Tumors. Cell 171, 358-371.e9.

Favaro, E., Bensaad, K., Chong, M. G., Tennant, D. A., Ferguson, D. J. P., Snell, C., Steers, G., Turley, H., Li, J.-L., Günther, UL., et al. (2012). Glucose Utilization via Glycogen Phosphorylase Sustains Proliferation and Prevents Premature Senescence in Cancer Cells. Cell Metab. 16, 751-764.

Gao, X., Sanderson, S. M., Dai, Z., Reid, M. A., Cooper, D. E., Lu, M., Richie, J. P., Ciccarella, A., Calcagnotto, A., Mikhael, P. G., et al. (2019). Dietary methionine influences therapy in mouse cancer models and alters human metabolism. Nature.

Garcia-Cañaveras, J. C., Chen, L., and Rabinowitz, J. D. (2019). The Tumor Metabolic Microenvironment: Lessons from Lactate. Cancer Res. 79, 3155-3162.

Goodman, R. P., Markhard, A. L., Shah, H., Sharma, R., Skinner, O. S., Clish, C. B., Deik, A., Patgiri, A., Hsu, Y.-H. H., Masia, R., et al. (2020). Hepatic NADH reductive stress underlies common variation in metabolic traits. Nature 1-5.

de Groot, S., Lugtenberg, R. T., Cohen, D., Welters, M. J. P., Ehsan, I., Vreeswijk, M. P. G., Smit, V. T. H. B. M., de Graaf, H., Heijns, J. B., Portielje, J. E. A., et al. (2020). Fasting mimicking diet as an adjunct to neoadjuvant chemotherapy for breast cancer in the multicentre randomized phase 2 DIRECT trial. Nat. Commun. 11, 3083.

Hingorani, S. R., Wang, L., Multani, A. S., Combs, C., Deramaudt, T. B., Hruban, R. H., Rustgi, A. K., Chang, S., and Tuveson, D. A. (2005). Trp53R172H and KrasG12D cooperate to promote chromosomal instability and widely metastatic pancreatic ductal adenocarcinoma in mice. Cancer Cell 7, 469-483.

Hompland, T., Hole, K. H., Ragnum, H. B., Aarnes, E.-K., Vlatkovic, L., Lie, A. K., Patzke, S., Brennhovd, B., Seierstad, T., and Lyng, H. (2018). Combined MR Imaging of Oxygen Consumption and Supply Reveals Tumor Hypoxia and Aggressiveness in Prostate Cancer Patients. Cancer Res. 78, 4774-4785.

Hopkins, B. D., Pauli, C., Du, X., Wang, D. G., Li, X., Wu, D., Amadiume, S. C., Goncalves, M. D., Hodakoski, C., Lundquist, M. R., et al. (2018). Suppression of insulin feedback enhances the efficacy of PI3K inhibitors. Nature 560, 499-503.

Hui, S., Ghergurovich, J. M., Morscher, R. J., Jang, C., Teng, X., Lu, W., Esparza, L. A., Reya, T., Le Zhan, Yanxiang Guo, J., et al. (2017). Glucose feeds the TCA cycle via circulating lactate. Nature 551, 115-118.

Hui, S., Cowan, A. J., Zeng, X., Yang, L., TeSlaa, T., Li, X., Bartman, C., Zhang, Z., Jang, C., Wang, L., et al. (2020). Quantitative Fluxomics of Circulating Metabolites. Cell Metab.

Jameson, G. S., Borazanci, E. H., Babiker, H. M., Poplin, E., Niewiarowska, A. A., Gordon, M. S., Barrett, M. T., Ansaldo, K., Lebron, L., Stoll, A. C., et al. (2017). A phase Ib/II pilot trial with nab-paclitaxel plus gemcitabine plus cisplatin in patients (pts) with stage IV pancreatic cancer. J. Clin. Oncol. 35, 341-341.

Jameson, G. S., Borazanci, E., Babiker, H. M., Poplin, E., Niewiarowska, A. A., Gordon, M. S., Barrett, M. T., Rosenthal, A., Stoll-D'Astice, A., Crowley, J., et al. (2020). Response Rate Following Albumin-Bound Paclitaxel Plus Gemcitabine Plus Cisplatin Treatment Among Patients With Advanced Pancreatic Cancer: A Phase 1b/2 Pilot Clinical Trial. JAMA Oncol. 6, 125.

Juweid, M. E., and Cheson, B. D. (2009). Positron-Emission Tomography and Assessment of Cancer Therapy (Massachusetts Medical Society).

Kamphorst, J. J., Cross, J. R., Fan, J., Stanchina, E. de, Mathew, R., White, E. P., Thompson, C. B., and Rabinowitz, J. D. (2013). Hypoxic and Ras-transformed cells support growth by scavenging unsaturated fatty acids from lysophospholipids. Proc. Natl. Acad. Sci. 110, 8882-8887.

Kanarek, N., Petrova, B., and Sabatini, D. M. (2020). Dietary modifications for enhanced cancer therapy. Nature 579, 507-517.

Koong, A. C., Mehta, V. K., Le, Q. T., Fisher, G. A., Terris, D. J., Brown, J. M., Bastidas, A. J., and Vierra, M. (2000). Pancreatic tumors show high levels of hypoxia. Int. J. Radiat. Oncol. 48, 919-922.

Korge, P., Calmettes, G., and Weiss, J. N. (2015). Increased reactive oxygen species production during reductive stress: The roles of mitochondrial glutathione and thioredoxin reductases. Biochim. Biophys. Acta BBA—Bioenerg. 1847, 514-525.

Lardinois, D., Weder, W., Hany, T. F., Kamel, E. M., Korom, S., Seifert, B., von Schulthess, G. K., and Steinert, H. C. (2003). Staging of non-small-cell lung cancer with integrated positron-emission tomography and computed tomography. N. Engl. J. Med. 348, 2500-2507.

Li, B., and Dewey, C. N. (2011). RSEM: accurate transcript quantification from RNA-Seq data with or without a reference genome. BMC Bioinformatics 12, 323.

Love, M. I., Huber, W., and Anders, S. (2014). Moderated estimation of fold change and dispersion for RNA-seq data with DESeq2. Genome Biol. 15, 550.

Lunt, S. Y., and Vander Heiden, M. G. (2011). Aerobic Glycolysis: Meeting the Metabolic Requirements of Cell Proliferation. Annu. Rev. Cell Dev. Biol. Vol 27 27, 441-464.

Maddocks, O. D. K., Athineos, D., Cheung, E. C., Lee, P., Zhang, T., van den Broek, N. J. F., Mackay, G. M., Labuschagne, C. F., Gay, D., Kruiswijk, F., et al. (2017). Modulating the therapeutic response of tumours to dietary serine and glycine starvation. Nature 544, 372-376.

McGarry, J. D., Guest, M. J., and Foster, D. W. (1970). Ketone Body Metabolism in the Ketosis of Starvation and Alloxan Diabetes. J. Biol. Chem. 245, 4382-4390.

Morscher, R. J., Aminzadeh-Gohari, S., Feichtinger, R. G., Mayr, J. A., Lang, R., Neureiter, D., Sperl, W., and Kofler, B. (2015). Inhibition of Neuroblastoma Tumor Growth by Ketogenic Diet and/or Calorie Restriction in a CD1-Nu Mouse Model. PLOS ONE 10, e0129802.

Olive, K. P., Jacobetz, M. A., Davidson, C. J., Gopinathan, A., McIntyre, D., Honess, D., Madhu, B., Goldgraben, M. A., Caldwell, M. E., Allard, D., et al. (2009). Inhibition of Hedgehog signaling enhances delivery of chemotherapy in a mouse model of pancreatic cancer. Science 324, 1457-1461.

Patgiri, A., Skinner, O. S., Miyazaki, Y., Schleifer, G., Marutani, E., Shah, H., Sharma, R., Goodman, R. P., To, T.-L., Robert Bao, X., et al. (2020). An engineered enzyme that targets circulating lactate to alleviate intracellular NADH:NAD+ imbalance. Nat. Biotechnol. 38, 309-313.

Pérez-Escuredo, J., Van Hée, V. F., Sboarina, M., Falces, J., Payen, V. L., Pellerin, L., and Sonveaux, P. (2016). Monocarboxylate transporters in the brain and in cancer. Biochim. Biophys. Acta BBA—Mol. Cell Res. 1863, 2481-2497.

Poff, A., Ari, C., Arnold, P., Seyfried, T., and D'Agostino, D. (2014). Ketone supplementation decreases tumor cell viability and prolongs survival of mice with metastatic cancer. Int. J. Cancer J. Int. Cancer 135, 1711-1720.

Puchalska, P., and Crawford, P. A. (2017). Multi-dimensional Roles of Ketone Bodies in Fuel Metabolism, Signaling, and Therapeutics. Cell Metab. 25, 262-284.

Rabinowitz, J. D., and Enerbäck, S. (2020). Lactate: the ugly duckling of energy metabolism. Nat. Metab. 2, 566-571.

Roberts, M. N., Wallace, M. A., Tomilov, A. A., Zhou, Z., Marcotte, G. R., Tran, D., Perez, G., Gutierrez-Casado, E., Koike, S., Knotts, T. A., et al. (2017). A Ketogenic Diet Extends Longevity and Healthspan in Adult Mice. Cell Metab. 26, 539-546.e5.

Shimazu, T., Hirschey, M. D., Newman, J., He, W., Shirakawa, K., Le Moan, N., Grueter, C. A., Lim, H., Saunders, L. R., Stevens, R. D., et al. (2013). Suppression of oxidative stress by β-hydroxybutyrate, an endogenous histone deacetylase inhibitor. Science 339, 211-214.

Shukla, S. K., Gebregiworgis, T., Purohit, V., Chaika, N. V., Gunda, V., Radhakrishnan, P., Mehla, K., Pipinos, I. I., Powers, R., Yu, F., et al. (2014). Metabolic reprogramming induced by ketone bodies diminishes pancreatic cancer cachexia. Cancer Metab. 2, 18.

Sullivan, L. B., Gui, D. Y., Hosios, A. M., Bush, L. N., Freinkman, E., and Vander Heiden, M. G. (2015). Supporting Aspartate Biosynthesis Is an Essential Function of Respiration in Proliferating Cells. Cell 162, 552-563.

Sullivan, M. R., Danai, L. V., Lewis, C. A., Chan, S. H., Gui, D. Y., Kunchok, T., Dennstedt, E. A., Vander Heiden, M. G., and Muir, A. (2019). Quantification of microenvironmental metabolites in murine cancers reveals determinants of tumor nutrient availability. ELife 8, e44235.

Tanner, L. B., Goglia, A. G., Wei, M. H., Sehgal, T., Parsons, L. R., Park, J. O., White, E., Toettcher, J. E., and Rabinowitz, J. D. (2018). Four Key Steps Control Glycolytic Flux in Mammalian Cells. Cell Syst. 7, 49-62.e8.

TeSlaa, T., Bartman, C. R., Jankowski, C. S. R., Zhang, Z., Xu, X., Xing, X., Wang, L., Lu, W., Hui, S., and Rabinowitz, J. D. (2021). The Source of Glycolytic Intermediates in Mammalian Tissues. Cell Metab. S1550413120307282.

Titov, D. V., Cracan, V., Goodman, R. P., Peng, J., Grabarek, Z., and Mootha, V. K. (2016). Complementation of mitochondrial electron transport chain by manipulation of the NAD+/NADH ratio. Science 352, 231-235.

Von Hoff, D. D., Ervin, T., Arena, F. P., Chiorean, E. G., Infante, J., Moore, M., Seay, T., Tjulandin, S. A., Ma, W. W., Saleh, M. N., et al. (2013). Increased Survival in Pancreatic Cancer with nab-Paclitaxel plus Gemcitabine. N. Engl. J. Med. 369, 1691-1703.

Weber, D. D., Aminazdeh-Gohari, S., and Kofler, B. (2018). Ketogenic diet in cancer therapy. Aging 10, 164-165.

Weber, D. D., Aminzadeh-Gohari, S., Tulipan, J., Catalano, L., Feichtinger, R. G., and Kofler, B. (2020). Ketogenic diet in the treatment of cancer—Where do we stand? Mol. Metab. 33, 102-121.

Wu, G. Y., and Thompson, J. R. (1988). The effect of ketone bodies on alanine and glutamine metabolism in isolated skeletal muscle from the fasted chick. Biochem. J. 255, 139-144.

Yang, L., Garcia Canaveras, J. C., Chen, Z., Wang, L., Liang, L., Jang, C., Mayr, J. A., Zhang, Z., Ghergurovich, J. M., Zhan, L., et al. (2020). Serine Catabolism Feeds NADH when Respiration Is Impaired. Cell Metab. 31, 809-821.e6.

Zahra, A., Fath, M. A., Opat, E., Mapuskar, K. A., Bhatia, S. K., Ma, D. C., Iii, S. N. R., Snyders, T. P., Chenard, C. A., Eichenberger-Gilmore, J. M., et al. (2017). Consuming a Ketogenic Diet while Receiving Radiation and Chemotherapy for Locally Advanced Lung Cancer and Pancreatic Cancer: The University of Iowa Experience of Two Phase 1 Clinical Trials. Radiat. Res. 187, 743-754.

Figure 5A:
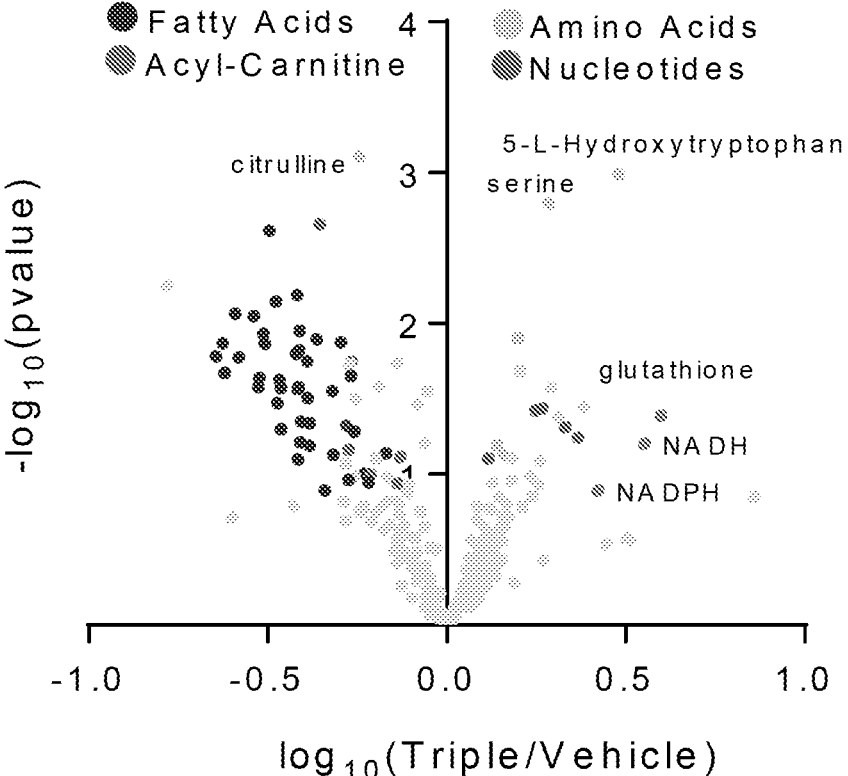
FIG. 5A is a volcano plot, and compares metabolite level in tumor tissues treated with triple chemotherapy or vehicle. Triple chemotherapy reduces free fatty acids and acyl-carnitine level in KPC tumors.

Example 2. Metabolomic Analysis and Fatty Acid Contribution to Synergy of Ketogenic Diet and Cytotoxic Chemotherapy To further explore the mechanism of synergy between cytotoxic chemotherapy and ketogenic diet, untargeted metabolomic analysis of allografted tumors treated with triple chemotherapy on standard diet or ketogenic diet was also carried out. Triple chemotherapy resulted in increased levels of NAD(H), NADP(H), glutathione, certain nucleotides and amino acids, and decreased levels of free fatty acids and fatty acyl-carnitines (FIG. 5A). Membrane lipids (phospholipids) and storage lipids (triglycerides) were largely unchanged. The decrease in both free fatty acids and carnitine-conjugated fatty acids, together, suggests a decrease in mitochondrial fatty acid oxidation, since longer fatty acids must be conjugated to carnitine to be imported into the organelle. Decreased fatty acid oxidation in mitochondria is consistent with chemotherapy selecting for less oxidative cells.

Figure 5B:
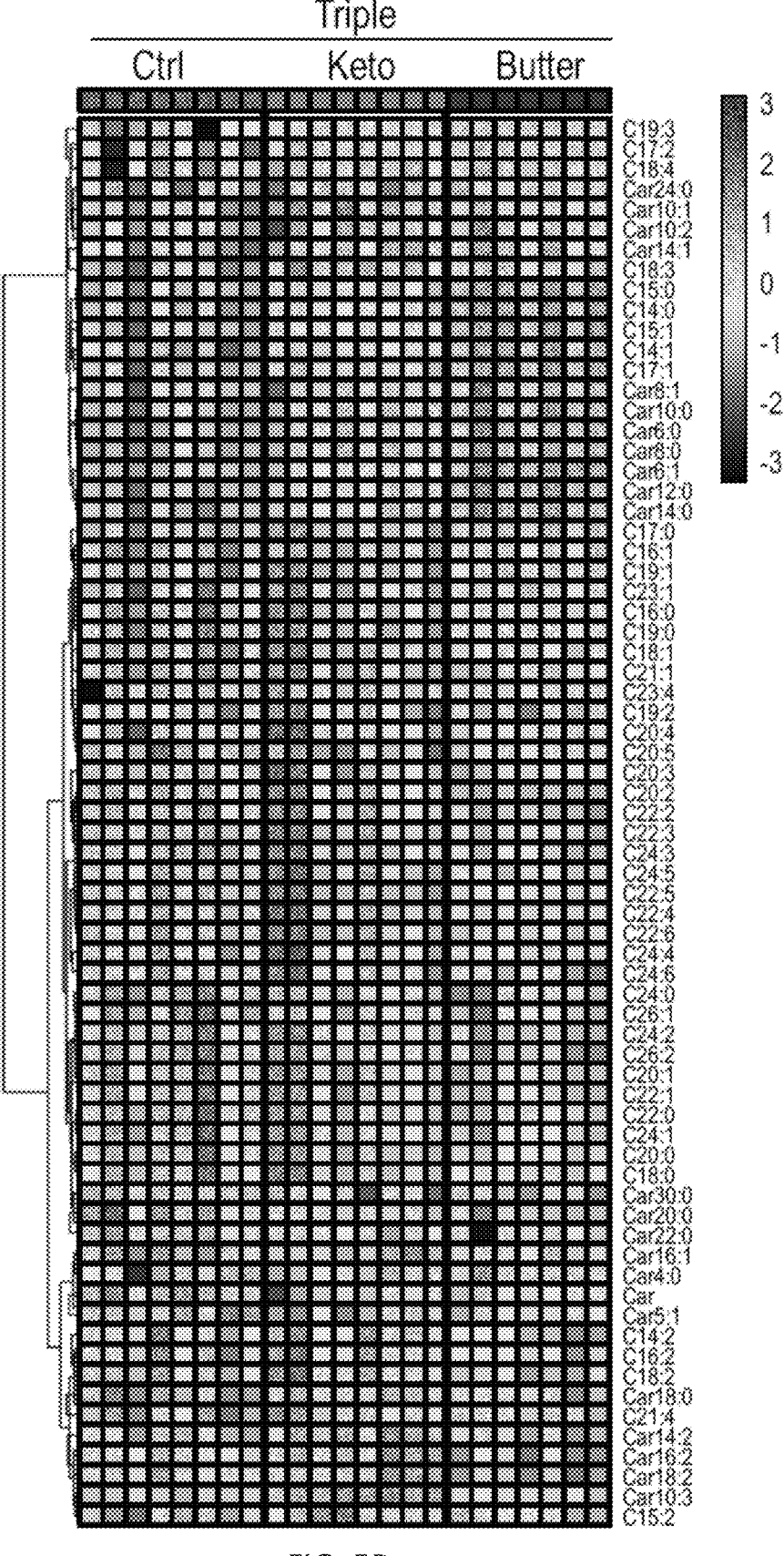
FIG. 5B is a heatmap of free fatty acids and acyl carnitine level in tumors treated with triple chemotherapy (abraxane, gemcitabine, cisplatin) in control diet, normal ketogenic diet and butter ketogenic diet.

Comparing triple chemotherapy-treated tumors in mice on the different diets, it was observed that tumors in mice on the ketogenic diet had much higher levels of both 3HB and acetoacetate, confirming that ketone body metabolism is much more active in these tumors. Ketogenic diet tumors exhibited higher levels of free fatty acids and fatty acyl-carnitines as well (FIG. 5B), suggesting that the ketogenic diet context forces the tumors into oxidative metabolism of both fatty acids and ketone bodies.

Figure 5C:
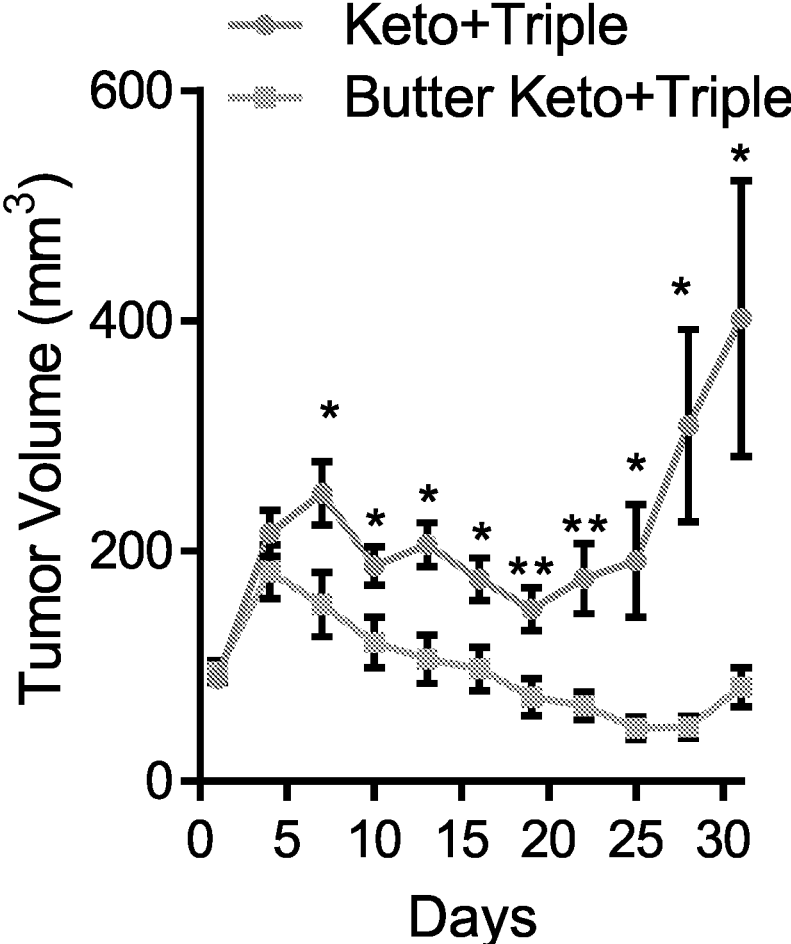
FIG. 5C shows tumor volumes of KPC tumor allografted in C57BL6 mice treated with chemotherapy, fed with ketogenic diets (normal, and butter).
Figure 5D:
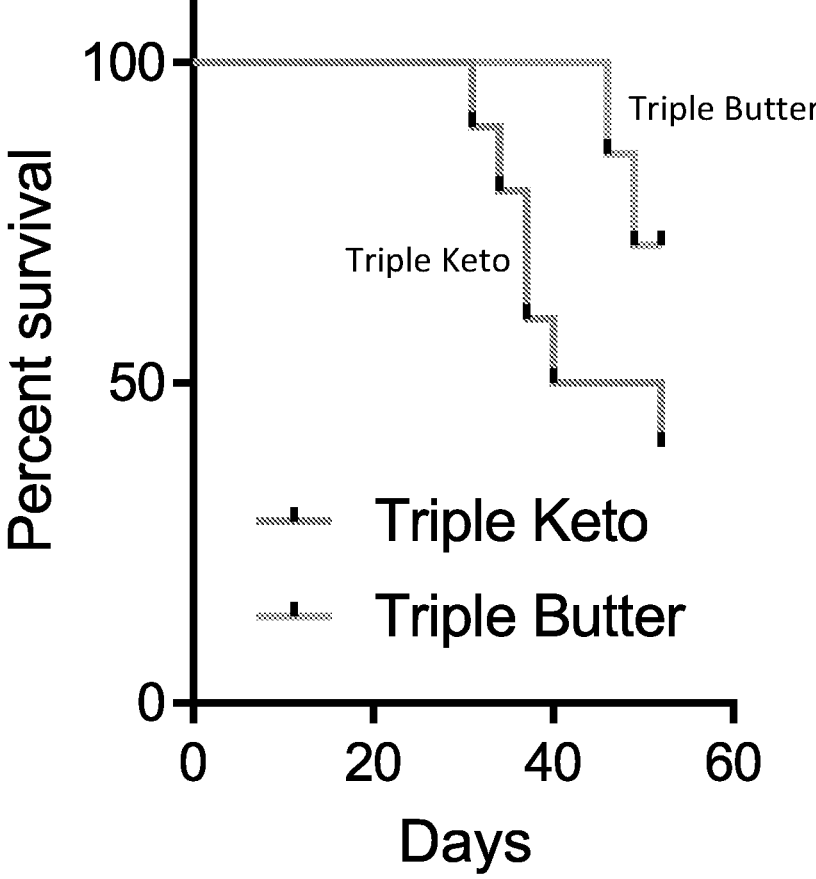
FIG. 5D shows percent survival of C57BL6 mice bearing KPC tumors treated with triple chemotherapy, fed with ketogenic diet (normal, butter).
Figure 5E:
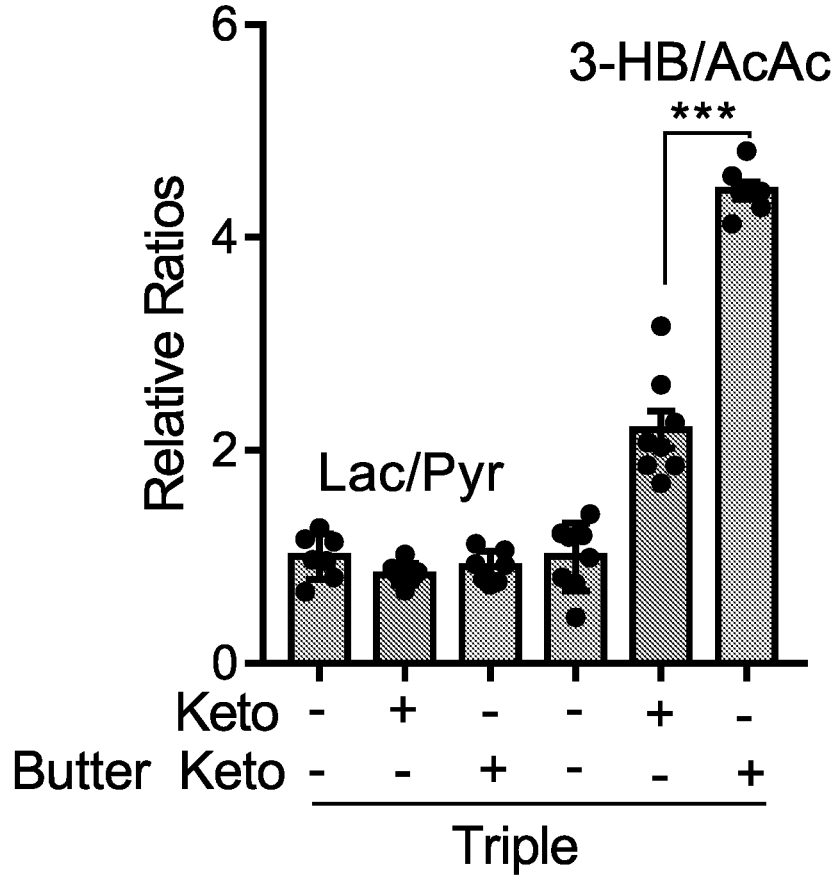
FIG. 5E shows ratio of lactate/pyruvate and 3-HB/AcAc in tumor tissues from FIG. 5B.

Most calories in the standard ketogenic diet come from a mixture of saturated fat and unsaturated fat. Whether a ketogenic diet heavy in saturated fatty acids—a "butter diet"—has a different effect was tested. Mice were fed with a ketogenic diet having a ratio of saturated fat: monounsaturated fat: polyunsaturated fat equal to 0.43:0.4:0.17 (based on weight), or a "butter diet" having a ratio of saturated fat: monounsaturated fat: polyunsaturated fat equal to 0.51:0.21:0.03 (based on weight) for three days before being dosed with the initial dosage of triple chemotherapy. Butter diet sensitized tumors to chemotherapy even more than the standard ketogenic diet (FIGS. 5C and 5D). Notably, the 3HB-to-acetoacetate ratio was yet further increased in butter diet relative to ketogenic diet, which is consistent with the idea that enhanced anti-tumor response observed in the butter diet-treated mice is due to stronger reductive stress (FIG. 5E).

Example 3. Ketogenic and Ketone Supplemented Diets Suppress HCT116 Growth In Vivo To test the impact of ketogenic diet on the growth rate of colorectal cancer, HCT116 cells were implanted in immune-deficient, NSG mice. Briefly, HCT116 colorectal cancer cells were cultured in DMEM with 10% FBS in an atmosphere of 5% $CO_2$. After cells were around 80% confluency, cells were trypsinized and detached from the petri dish. Cell number was counted, and the cell suspension was concentrated to 30 million cells/ml. Cell suspension was mixed 1:1 with Matrigel (BD 3564), and 200 µl of the resulting solution were implanted into NSG mice flanks. After tumors were palpable (around 50 mm³), mice were randomly assigned to PicoLab diet 5053 (standard diet) or ketogenic diet (Bioserv, S3666) group, and tumor size was measured every three days with calipers using the following equation: volume=½*length*width*height. LC-MS sample preparation and methods were as described in Example 1. Western blot method was as described in Example 1.

Figure 6A:
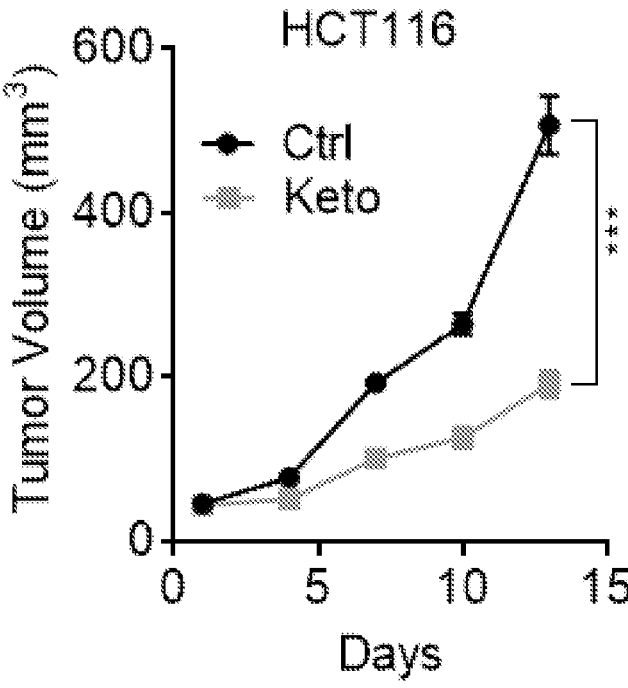
FIG. 6A shows tumor volumes of colorectal cancer HCT116 xenografts on xenografted NSG mice on control diet or ketogenic diet. Mean±SEM, n=11.
Figure 6B:
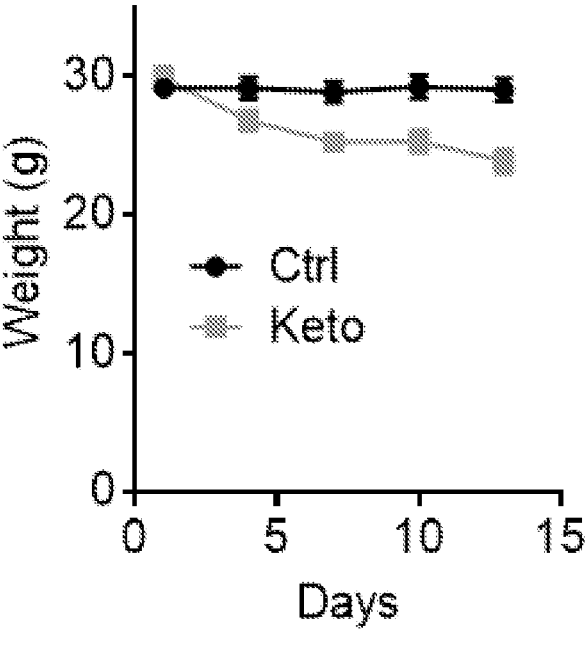
FIG. 6B shows body weight of xenografted NSG mice on control diet or ketogenic diet. Mean±SEM, n=14.
Figure 6C:
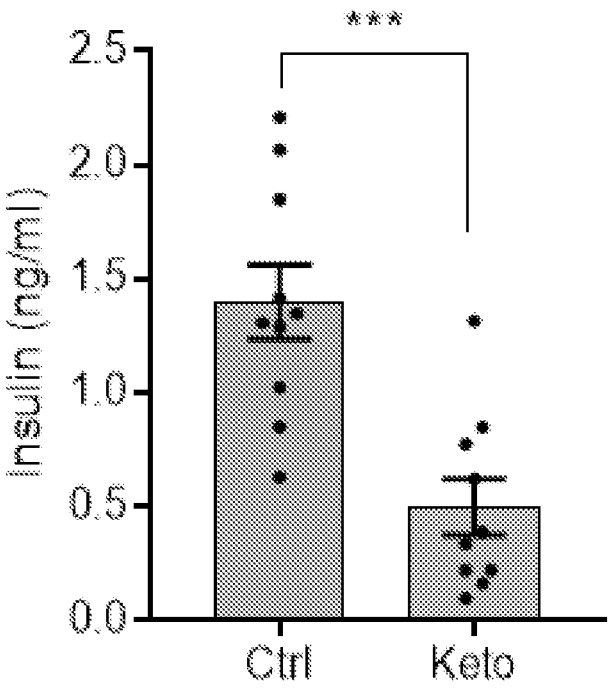
FIG. 6C shows insulin levels of mice fed ad lib with control diet or ketogenic diet. Mean±SEM, n=10.
Figure 6D:
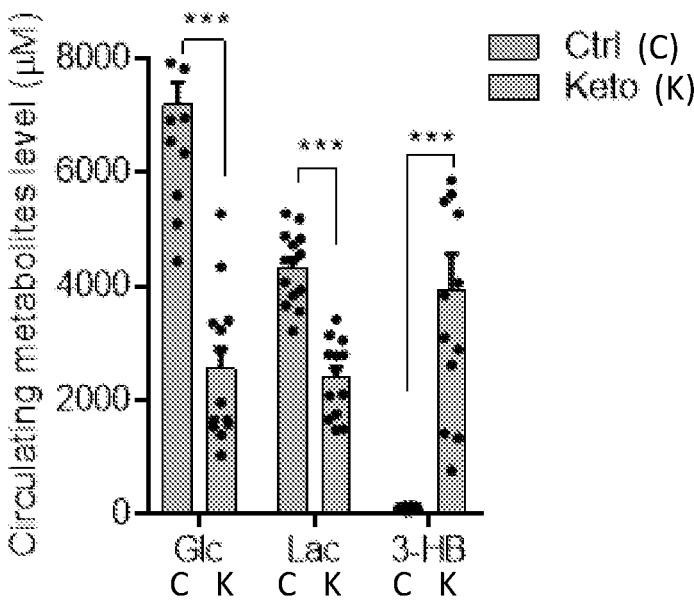
FIG. 6D shows circulatory glucose, lactate and 3-HB levels in mice fed ad lib with control diet or ketogenic diet. Mean±SEM, n=14 for control diet group, n=13 for ketogenic diet group.
Figure 6E:
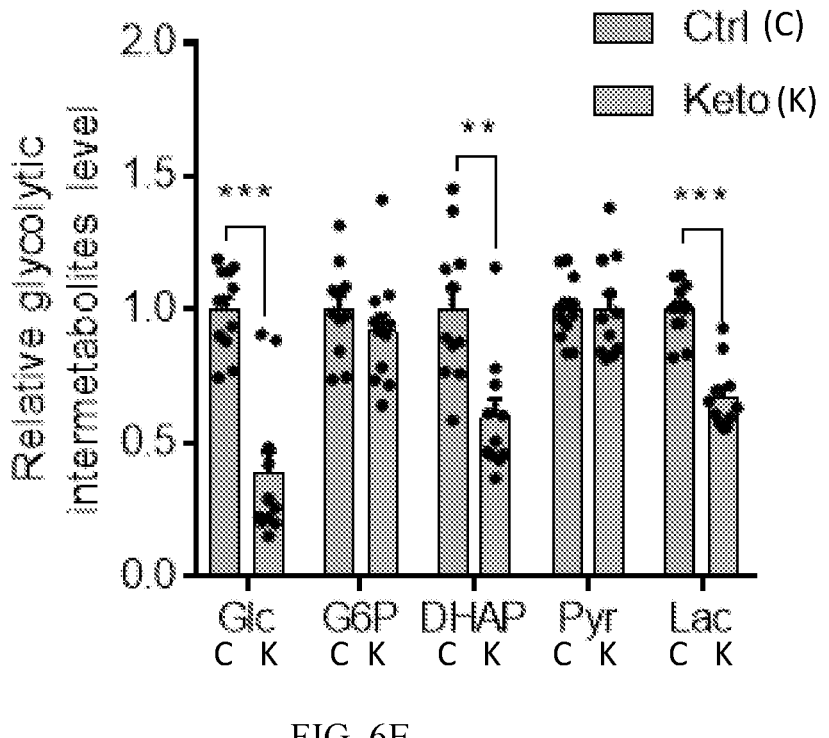
FIG. 6E shows relative levels of intratumor glycolytic metabolites for mice fed with control diet or ketogenic diet. Mean±SEM, n=11.
Figure 6F:
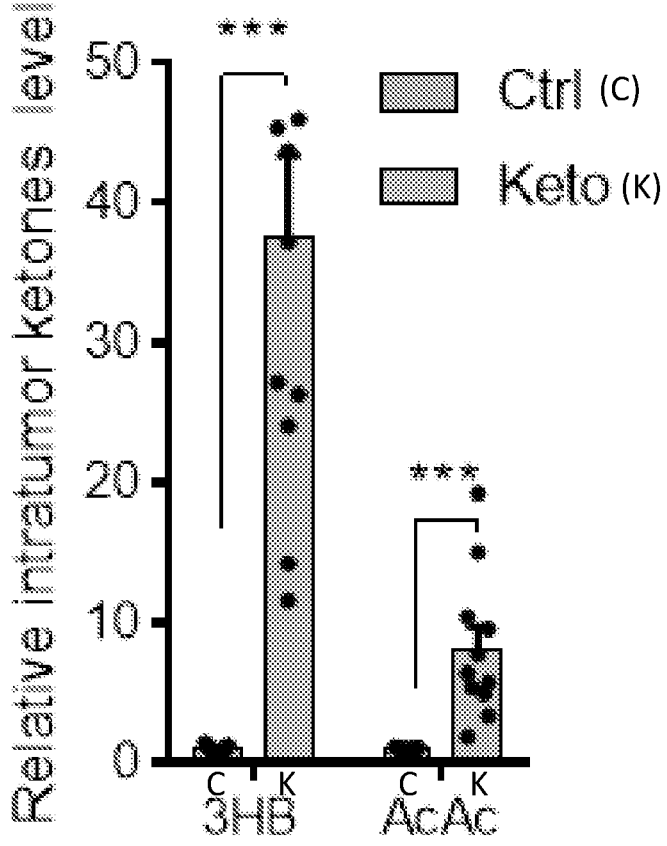
FIG. 6F shows relative levels of intratumor 3-1113 and acetoacetate for mice fed with control diet or ketogenic diet. Mean±SEM, n=11.

FIGS. 6A and 6B show that a ketogenic diet can slow the growth rate of HCT116 xenografts, without strongly affecting body weight of the mice. In further examining the metabolic consequences caused by ketogenic diet in NSG mice tumor xenograft model, it was found that ketogenic diet strongly suppressed insulin levels, reduced circulating glucose and lactate, and boosted circulatory ketones levels (FIGS. 6C and 6D). Reduced levels of glycolytic metabolites, and increased levels of 3-hydroxybutyrate (3-HB) and acetoacetate (AcAc) were also found in tumors for mice fed with ketogenic diet (FIGS. 6E and 6F). These results suggest an impaired glycolytic flux and enhanced ketone oxidation in HCT116 xenografted mice fed a ketogenic diet.

To uncover the key metabolic factor which determines tumor growth, mice were fed with ketone diet, which switches 17% calories from carbohydrate in AIN-93 standard diet to R(3)-hydroxybutyryl-R(3)-hydroxybutyrate.

R(3)-hydroxybutyryl-R(3)-hydroxybutyrate can be decomposed into two molecules of 3-hydroxybutyrate via the functions of gut esterase and a series of dehydrogenases in liver (e.g., ethanol dehydrogenase, aldehyde dehydrogenase and 3-hydroxybutyrate dehydrogenase). Veech, R. L. Ketone effects on metabolism and transcription. *J. Lipid Res.* 55, 2004-2006 (2014). For ketone diet experiments, mice were acclimated to their corresponding control diets for one week to maintain body weight. Afterward, HCT116 cells were implanted into NSG mice flanks. After tumor sizes were palpable, mice were randomly assigned to ketone diet or its control diet (diets were kindly supplied by Todd King, NIH/NIAAA). Tumor sizes were monitored every three days with calipers using the following equation: volume=½*length*width*height. LC-MS sample preparation and methods were as described in Example 1. Western blot method was as described in Example 1.

Figure 7A:
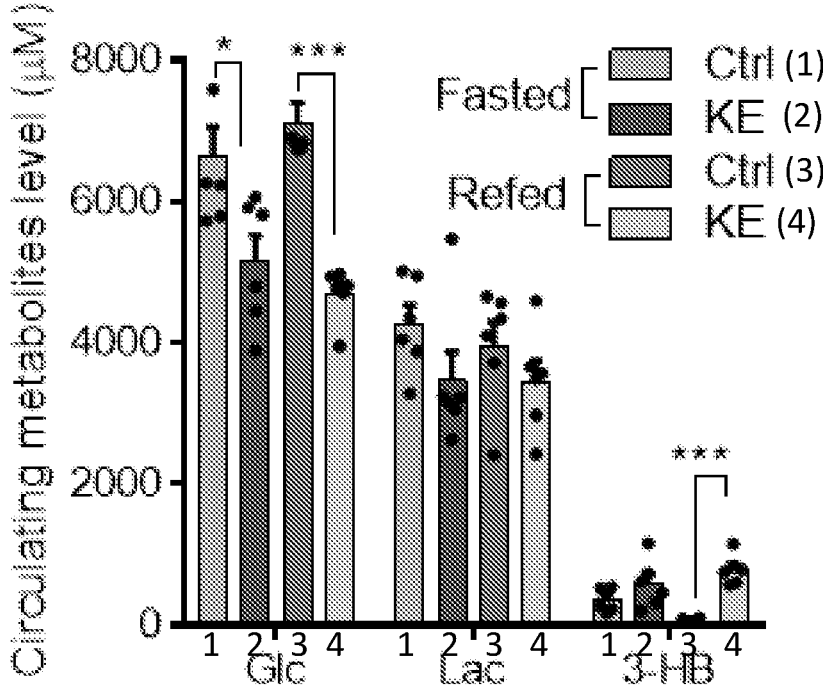
FIG. 7A shows circulatory glucose, lactate and 3-1113 levels in mice fasted for 7 hours and refed with control diet or ketone diet. Mean±SEM, n=6.
Figure 7B:
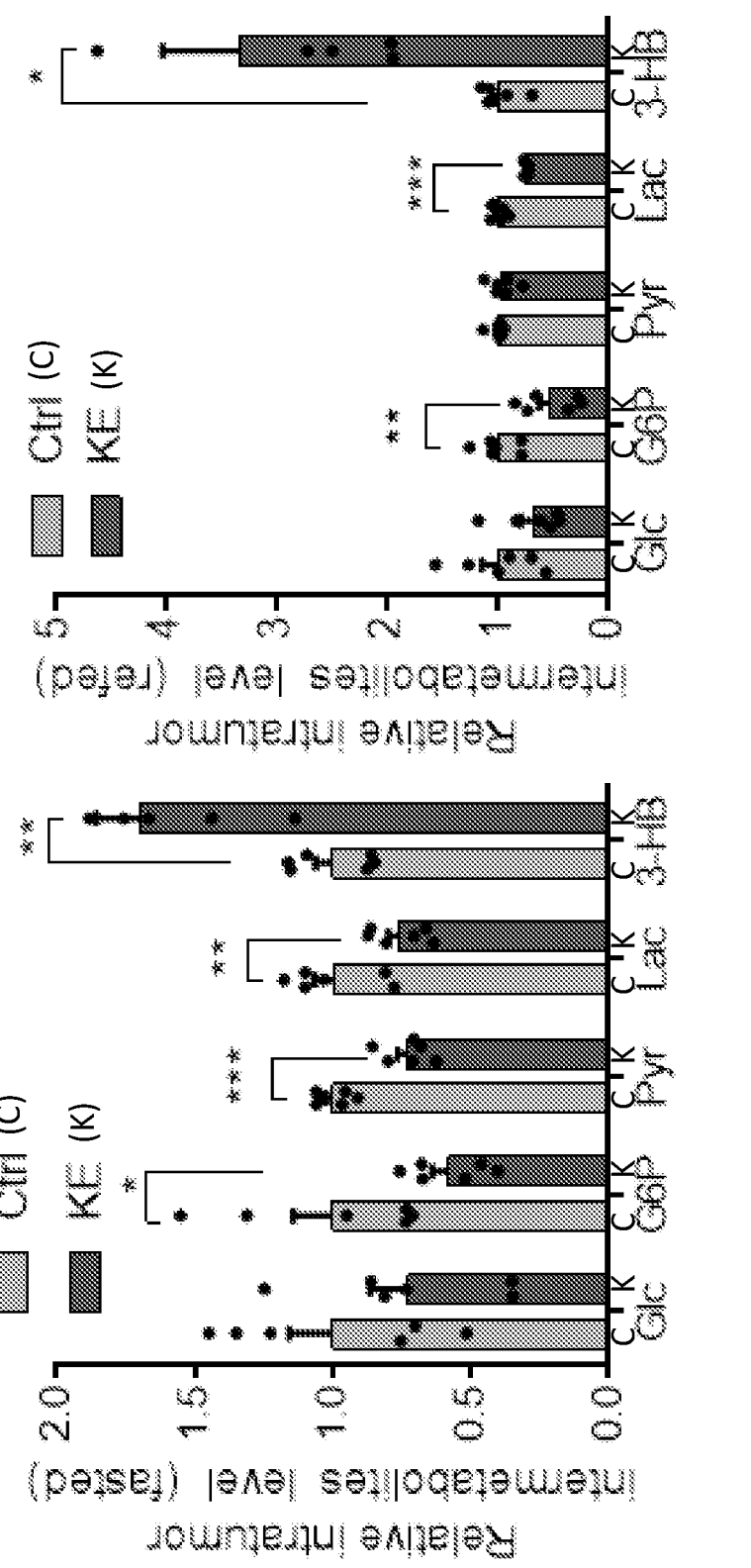
FIG. 7B shows relative levels of intratumor glycolytic metabolites and 3-1113 in mice fasted for 7 hours and refed with control diet or ketone diet. Mean±SEM, n=6.
Figure 7C:
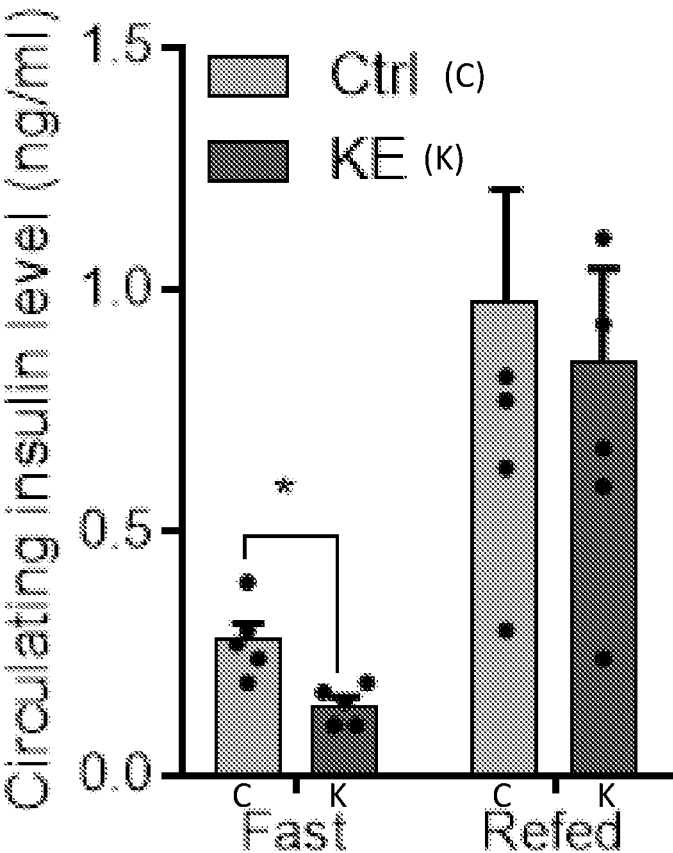
FIG. 7C shows insulin levels of mice fasted for 7 hours and refed with control diet or ketogenic diet. Mean±SEM, n=6.
Figure 7D:
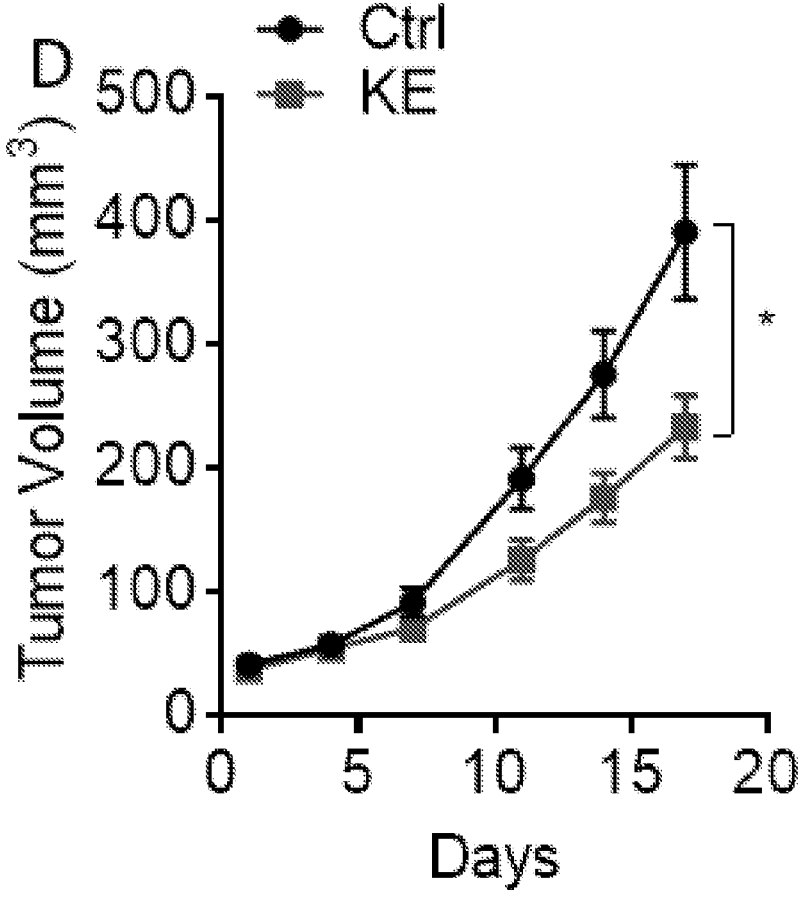
FIG. 7D shows tumor volumes of colorectal cancer HCT116 xenografts on xenografted NSG mice fed control diet or ketogenic diet. Mean±SEM, n=12.
Figure 7E:
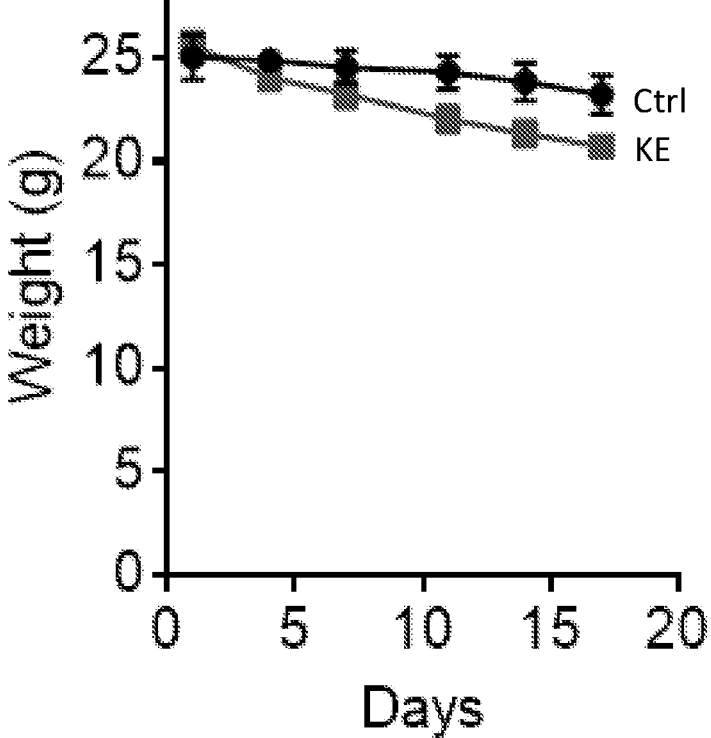
FIG. 7E shows body weight of xenografted NSG mice fed control diet or ketogenic diet. Mean±SEM, n=6.

FIGS. 7A-7C show an increased level of 3-hydroxybutyrate in circulation and in tumors when mice were refed with corresponding diets. Reduced levels of circulatory glucose and glycolytic intermetabolites in tumors were also observed. However, although the insulin level was relatively lower in a fasted state, it was largely maintained when mice were refed (FIG. 7C). Nonetheless, the ketone diet suppressed tumor growth rate, while maintaining mice body weight (FIGS. 7D and 7E). These results indicate that ketone diet could help slow the growth rate of colorectal cancer.

Example 4. Study Evaluating the Ketogenic Diet in Patients with Metastatic Pancreatic Cancer To explore the possibility for tumor control such as that described in Example 1 to translate to the clinic, clinical trial NCT04631445 was initiated. NCT04631445 is a randomized, phase II trial designed to evaluate the progression free survival in patients with metastatic pancreatic cancer on triplet therapy (nab-paclitaxel+gemcitabine+cisplatin) while on ketogenic diet or non-ketogenic diet. This study also aims to compare the changes in serum metabolites and quality of life between the two arms.

The experimental arm (Ketogenic (KD)+Triplet) consists of ketogenic diet plus nab-paclitaxel 125 mg/m², cisplatin 25 mg/m², and gemcitabine 1000 mg/m², all administered intravenously (IV) on Days 1 and 8 every 21 days. Ketogenic diet (KD) includes the following macronutrients: dietary carbohydrates restricted to <30 g/day; and daily protein intake targeted to 1.5 g/kg/day (targeted to ideal body weight). The no intervention arm (Non-ketogenic+Triplet) consists of non-ketogenic diet plus nab-paclitaxel 125 mg/m², cisplatin 25 mg/m², and gemcitabine 1000 mg/m², all administered intravenously (IV) on Days 1 and 8 every 21 days.

The primary outcome measure is progression-free survival per RECIST 1.1 [Time Frame: 36 months], wherein progression-free survival (PFS) is defined as the time from randomization to first documentation of objective tumor progression or to death due to any cause. Secondary outcome measures include:

1. To compare the number of responses by RECIST 1.1 [Time Frame: 36 months]. To compare the number of complete responses/partial responses as defined by CT scan using the Response Evaluation Criteria In Solid Tumors 1.1 (RECIST 1.1) and CA 19-9 (or CA 125, or CEA if not expressers of CA 19-9) down to normal limits (from at least >2×ULN);
2. To compare the disease control rate using the Response Evaluation Criteria In Solid Tumors 1.1 (RECIST 1.1)

[Time Frame: 36 months], where disease control rate= (Partial Response+Complete Response+Stable Disease for at least 9 weeks);
3. Cancer Biomarkers [Time Frame: 36 months]: Change in CA 19-9 (or CA 125, or CEA if not expressers of CA 19-9);
4. Cancer Biomarkers returning to normal [Time Frame: 36 months]: Rates of normalization of CA 19-9 (or CA 125, or CEA if not expressers of CA 19-9);
5. Change in BMI [Time Frame: 36 months]: To compare the average weight (kg), using BMI calculation (BMI=weight (kg)/height (m²));
6. To compare average insulin levels [Time Frame: 36 months];
7. To compare the average HbgA1c level [Time Frame: 36 months];
8. To compare changes in serum metabolites [Time Frame: 36 months]; and
9. To compare quality of life between arms via the European Organization for Research and Treatment of Cancer Quality of Life Questionnaire QLC-C30 (EORTC QLQ-C30) assessment [Time Frame: 36 months].

Inclusion Criteria include:
1. Age ≥18 years of age; male or female.
2. Histologically or cytologically confirmed metastatic pancreatic ductal adenocarcinoma, not previously treated for their metastatic disease.
3. Capable of providing informed consent and complying with trial procedures.
4. Karnofsky Performance Status (KPS) of ≥70%.
5. Life expectancy ≥12 weeks.
6. Measurable tumor lesions according to RECIST 1.1 criteria.
7. <Grade 2 pre-existing peripheral neuropathy per NCI CTCAE, Version 5.0.
8. Patient has acceptable coagulation status as indicated by an INR ≤1.5 times institutional upper limit of normal (ULN). Patients on anticoagulation can be included at the discretion of the investigator.
9. Patients must have normal organ and marrow function as defined below:
   Absolute neutrophil count ≥1,500/mm3
   Platelet concentration ≥100,000/mm3 with no platelet transfusions within 7 days prior to laboratory sample
   Hemoglobin ≥9.0 g/dL (PRBCs may be given to meet this criteria)
   Hematocrit level ≥27%
   Total bilirubin within 1.25×ULN
   AST (SGOT), ALT (SGPT) and Alkaline phosphatase ≤2.5 times upper limit of normal (if liver metastases are present, then ≤5×ULN is allowed)
   Serum creatinine <1.5 mg/dL.
10. Patient must have a Smartphone or computer in order to work with Virta.
11. Females of child-bearing potential (defined as a sexually mature woman who (1) has not undergone hysterectomy [the surgical removal of the uterus] or bilateral oophorectomy [the surgical removal of both ovaries] or (2) has not been naturally postmenopausal for at least 24 consecutive months [i.e., has had menses at any time during the preceding 24 consecutive months]) must:
    1. Either commit to true abstinence* from heterosexual contact (which must be reviewed on a monthly basis), or agree to use, and be able to comply with, effective contraception without interruption, 28 days prior to starting IP therapy (including dose interruptions), and while on study medication or for a longer period if required by local regulations following the last dose of TP; and 2. Have a negative serum pregnancy test (β-hCG) result at screening and agree to ongoing pregnancy testing during the course of the study, and after the end of study therapy. This applies even if the subject practices true abstinence* from heterosexual contact.

12. Male subjects must practice true abstinence* or agree to use a condom during sexual contact with a pregnant female or a female of childbearing potential while participating in the study, during dose interruptions and for 6 months following discontinuation from study treatment, even if he has undergone a successful vasectomy.

True abstinence is acceptable when this is in line with the preferred and usual lifestyle of the subject. [Periodic abstinence (e.g., calendar, ovulation, symptothermal, post-ovulation methods) and withdrawal are not acceptable methods of contraception].

Exclusion criteria include:

1. Patients must have received no previous radiotherapy, surgery, chemotherapy or investigational therapy for the treatment of their metastatic pancreatic disease.

2. Evidence of central nervous system (CNS) metastasis (negative imaging study, if clinically indicated, within 4 weeks of Screening Visit).

3. History of other malignancies (except cured basal cell carcinoma, superficial bladder cancer or carcinoma in situ of the cervix) unless documented free of cancer for ≥2 years.

4. Uncontrolled intercurrent illness, including but not limited to New York Heart Association Class III or IV, myocardial infarction within the past 6 months, or unstable arrhythmia.

5. Known infection with HIV, hepatitis B, or hepatitis C.

6. Active, uncontrolled bacterial, viral, or fungal infections, requiring systematic therapy.

7. Major surgery within 4 weeks prior to study entry. (Port-a-cath may be inserted during this time period).

8. Any condition in the opinion of the principal investigator that might interfere with the patient's participation in the study or in the evaluation of the study results.

9. Any condition in the opinion of the principal investigator that is unstable and could jeopardize the patient's participation in the study.

10. Unwillingness or inability to comply with procedures required in this protocol, including unwillingness to follow a ketogenic diet.

11. Severe malnutrition or body mass index (BMI)<18.

12. Albumin <3.5 g/dL.

13. History of Type 1 diabetes.

14. History of diabetic ketoacidosis (DKA).

Patient dietary choices are supported by continuous remote medical care delivered over the Internet. Initial compliance is encouraging and further patient recruitment ongoing.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method for treating a pancreatic cancer in a subject in need thereof, comprising administering to the subject an effective amount of a chemotherapeutic regimen comprising:

gemcitabine, or a pharmaceutically acceptable salt thereof;

paclitaxel, or a pharmaceutically acceptable salt thereof, wherein the paclitaxel, or pharmaceutically acceptable salt thereof, is administered in albumin-bound form; and cisplatin, wherein the subject is on a ketogenic diet or a ketone supplement or both.

2. The method of claim 1, wherein the pancreatic cancer is metastatic.

3. The method of claim 1, wherein the subject is on a ketogenic diet but not a ketone supplement.

4. The method of claim 1, wherein the subject is on a ketone supplement but not a ketogenic diet.

5. The method of claim 1, wherein the subject is on a ketogenic diet and a ketone supplement.

6. The method of claim 1, wherein the chemotherapeutic regimen is administered once weekly for two consecutive weeks on a 21-day cycle, and is not administered during the third week of the 21-day cycle.

7. The method of claim 6, wherein the chemotherapeutic regimen is administered on days 1 and 8 of the 21-day cycle.

8. The method of claim 1, wherein:

about 1,000 mg/m$^2$ gemcitabine, or a pharmaceutically acceptable salt thereof, is administered to the subject per day;

about 125 mg/m$^2$ paclitaxel, or a pharmaceutically acceptable salt thereof, is administered to the subject per day; and about 25 mg/m$^2$ cisplatin, or a pharmaceutically acceptable salt thereof, is administered to the subject per day.

9. The method of claim 1, wherein the ketogenic diet has a weight ratio of saturated fatty acids to unsaturated fatty acids of greater than 1.

10. The method of claim 1, wherein the ketogenic diet comprises fat, protein and, optionally, carbohydrate, and the weight ratio of fat to the sum of protein and carbohydrate is at least or about: 2, 3, 4, 5, 6, 7, 8, 9 or 10.

11. The method of claim 1, wherein the ketogenic diet contains less than 5% by weight carbohydrate.

12. The method of claim 1, further comprising maintaining the subject on the ketogenic diet, the ketone supplement or both.

13. The method of claim 1, further comprising instructing the subject to consume the ketogenic diet, the ketone supplement or both.

* * * * *